US012162856B2

(12) United States Patent
Ji

(10) Patent No.: US 12,162,856 B2
(45) Date of Patent: *Dec. 10, 2024

(54) β-CATENIN AND B-CELL LYMPHOMA 9 (BCL9) INHIBITORS

(71) Applicant: H. LEE MOFFITT CANCER CENTER AND RESEARCH INSTITUTE, INC., Tampa, FL (US)

(72) Inventor: Haitao Ji, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 657 days.

This patent is subject to a terminal disclaimer.

(21) Appl. No.: 17/286,693

(22) PCT Filed: Oct. 18, 2019

(86) PCT No.: PCT/US2019/056908
§ 371 (c)(1),
(2) Date: Apr. 19, 2021

(87) PCT Pub. No.: WO2020/081918
PCT Pub. Date: Apr. 23, 2020

(65) Prior Publication Data
US 2021/0340123 A1    Nov. 4, 2021

(51) Int. Cl.
*C07D 401/12* (2006.01)
*C07D 207/12* (2006.01)

(52) U.S. Cl.
CPC ......... *C07D 401/12* (2013.01); *C07D 207/12* (2013.01)

(58) Field of Classification Search
CPC ............................. C07D 401/12; C07D 207/12
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,960,648 B2 | 11/2005 | Bonny |
| 11,542,254 B2 * | 1/2023 | Ji .................. C07D 207/12 |
| 2002/0035243 A1 | 3/2002 | Imfeld et al. |
| 2002/0120100 A1 | 8/2002 | Bonny |
| 2003/0032594 A1 | 2/2003 | Bonny |
| 2009/0325964 A1 | 12/2009 | Bursavich et al. |
| 2013/0158042 A1 | 6/2013 | Heimann et al. |
| 2018/0092866 A1 | 4/2018 | Ji et al. |

FOREIGN PATENT DOCUMENTS

WO    WO-2017165839 A1 *   9/2017   ........... C07D 207/12

OTHER PUBLICATIONS

International Search Report and Written Opinion in PCT/US2019/056908. Mailed Jan. 27, 2020. 9 pages.
Baell, Jonathan B., and Georgina A. Holloway. "New substructure filters for removal of pan assay interference compounds (PAINS) from screening libraries and for their exclusion in bioassays." Journal of medicinal chemistry 53.7 (2010): 2719-2740.
Baell, Jonathan, and Michael A. Walters. "Chemistry: Chemical con artists foil drug discovery." Nature News 513.7519 (2014): 481-483.
de La Roche, Marc, et al. "An intrinsically labile α-helix abutting the BCL9-binding site of β-catenin is required for its inhibition by carnosic acid." Nature communications 3.1 (2012), 680.
Kawamoto, Steven A., et al. "Design of triazole-stapled BCL9 α-helical peptides to target the β-catenin/B-cell CLL/lymphoma 9 (BCL9) protein-protein interaction." Journal of medicinal chemistry 55.3 (2012): 1137-1146.
Nikolovska-Coleska, Zaneta, et al. "Development and optimization of a binding assay for the XIAP BIR3 domain using fluorescence polarization." Analytical biochemistry 332.2 (2004): 261-273.
Takada, Kohichi, et al. "Targeted disruption of the BCL9/β-catenin complex inhibits oncogenic Wnt signaling." Science translational medicine 4.148 (2012): 148ra117-148ra117.
Toyoizumi, Takane, et al. "Combined therapy with chemotherapeutic agents and herpes simplex virus type 1 ICP34. 5 mutant (HSV-1716) in human non-small cell lung cancer." Human gene therapy 10.18 (1999): 3013-3029.
International Preliminary Report on Patentability issued for Application No. PCT/US2019/056908, dated Apr. 29, 2021.

* cited by examiner

*Primary Examiner* — Matthew P Coughlin
*Assistant Examiner* — Meghan C Heasley
(74) *Attorney, Agent, or Firm* — Meunier Carlin & Curfman LLC

(57) ABSTRACT

Disclosed are inhibitors for the β-catenin/BCL9 interaction. The inhibitors are selective for β-catenin/BCL9 over β-catenin/cadherin interactions. Methods of using the disclosed compounds to treat cancer are also disclosed.

18 Claims, 1 Drawing Sheet
Specification includes a Sequence Listing.

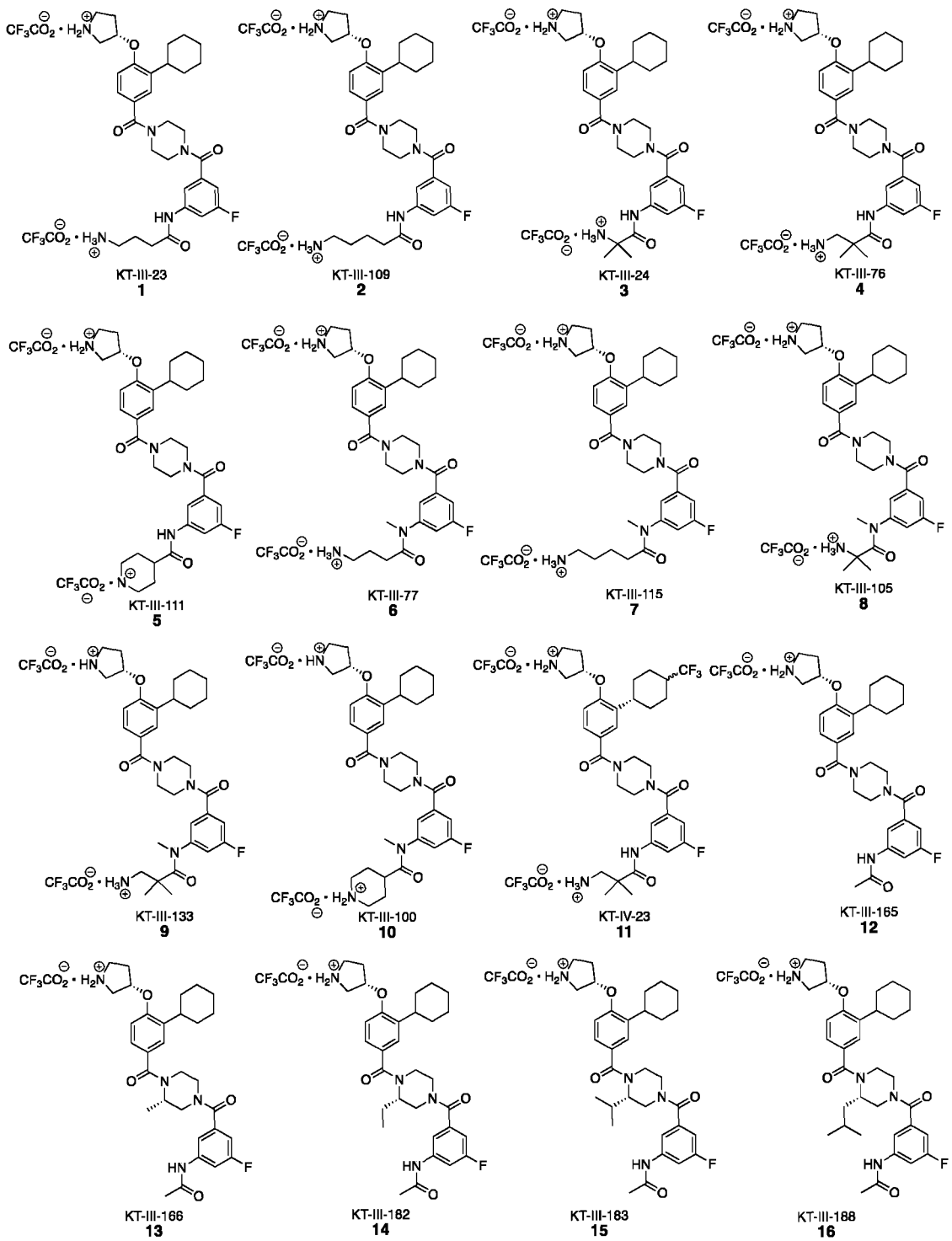

β-CATENIN AND B-CELL LYMPHOMA 9 (BCL9) INHIBITORS

CROSS REFERENCE TO RELATED APPLICATIONS

This application is a United States National Phase Patent Application of International Patent Application Number PCT/US2019/056908, filed on Oct. 18, 2019, which claims the benefit of and priority to U.S. Provisional Application Ser. No. 62/747,235 filed on Oct. 18, 2018, the disclosure of which is expressly incorporated herein by reference in its entirety.

BACKGROUND

Hyperactivation of the canonical Wnt signaling pathway has been associated with the initiation and progression of triple negative breast cancers (TNBCs). This hyperactivation is mainly caused by the autocrine/paracrine activation of Wnt ligands and the epigenetic silencing of Wnt antagonist genes, which results in accumulation of β-catenin in the cell nucleus and activates transcription of Wnt target genes. Wnt target genes initiate proliferation and metastasis of TNBC cells and self-renewal of TNBC stem cells. The formation of the β-catenin/B-cell lymphoma 9 (BCL9) complex in the cell nucleus is the penultimate step of canonical Wnt signaling. The aberrant formation of this protein-protein complex is a major driving force for TNBC tumorigenesis. The inhibition of the β-catenin/BCL9 interaction by small-molecule inhibitors represents an appealing therapeutic strategy. On the other hand, the surface area of β-catenin for binding with BCL9 is also used to bind cadherin. The β-catenin/cadherin interaction is essential for the integrity of epithelial junctions in normal cells. Therefore, the selectivity of small-molecule inhibitors for β-catenin/BCL9 over β-catenin/cadherin is important.

Stapled BCL9 L351-F374 α-helical peptides were designed to inhibit the β-catenin/BCL9 interaction (Kawamoto, et al. *J. Med Chem.* 2012, 55, 1137-1146; and Takada, et al. *Sci. Transl. Med* 2012, 4, 148ra117). The stapled peptides described in Kawamoto, et al. *J. Med Chem.* 2012, 55, 1137-1146 did not exhibit cell-based activity. SAH-BCL9 described in Takada, et al. *Sci. Transl. Med* 2012, 4, 148ra117 was able to pass the cell membrane, bind with β-catenin, disrupt the β-catenin/BCL9 interaction, and selectively suppress transcription of Wnt target genes. This stapled peptide also inhibited tumor cell growth, angiogenesis, and metastasis without overt damage to normal tissues in the mouse xenograft models for colorectal carcinoma and multiple myeloma. However, the aqueous solubility, the immunogenic effects, and the in vivo stability of SAH-BCL9 were not reported.

Compound screening identified a small organic molecule, camosic acid, that can disrupt the β-catenin/BCL9 interaction, inhibit β-catenin-dependent transcription, and destabilize activated β-catenin (de la Roche, et al. *Nature Commm.* 2012, 3, 680). Carnosic acid is a natural antioxidant and associated with many biological activities. Its catechol substructure readily reacts with protein nucleophiles after oxidation and has been recognized as a substructure for pan assay interference compounds (PAINS) (Baell and Holloway *J. Med Chem.* 2010, 53, 2719-2740; Beall and Walters *Nature* 2014, 513, 481-483). To date, no class-specific small-molecule inhibitors for the β-catenin/BCL9 interaction has been reported. Thus, what are needed are new, potent and selective inhibitors for the β-catenin/BCL9 interaction and methods for their use. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. The compounds can have a structure represented by Formula I.

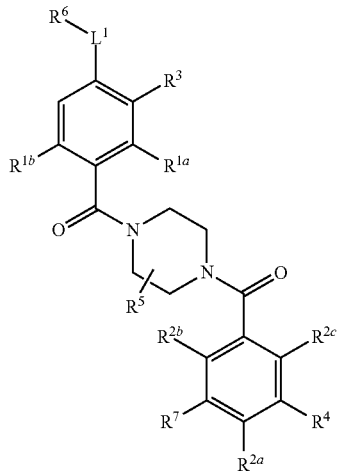

Formula I wherein $L^1$ is O, S, or NH;

wherein each of $R^{1a}$ and $R^{1b}$ is independently hydrogen, halogen, $C_1$-$C_3$ alkyl, $C_1$-$C_3$ monohaloalkyl, or $C_1$-$C_3$ polyhaloalkyl;

wherein each of $R^{2a}$, $R^{2b}$, and $R^{2c}$ is independently hydrogen, halogen, $C_1$-$C_3$ alkyl, $C_1$-$C_3$ haloalkyl, or $C_1$-$C_3$ polyhaloalkyl;

wherein $R^3$ is $Cy^3$ or $Ar^1$; wherein $Cy^3$ is a $C_3$-$C_8$ cycloalkyl or a $C_2$-$C_7$ heterocycloalkyl and Ar is selected from aryl and heteroaryl, wherein $Cy^3$ and $Ar^1$, when present, are substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$;

wherein $R^4$ is hydrogen, halogen, $C_1$-$C_3$ alkyl, $C_1$-$C_3$ haloalkyl, or $C_1$-$C_3$ polyhaloalkyl;

wherein each occurrence of $R^5$ is independently selected from hydrogen, $C_1$-$C_3$ alkyl;

wherein $R^6$ is $C_1$-$C_6$ aminoalkyl, $C_1$-$C_6$ hydroxyalkyl, or $Cy^1$; and wherein $Cy^1$ is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;

wherein $R^7$ is $C_1$-$C_6$ alkyl-(C=O)—$NR^{12}$—; amino-$C_1$-$C_6$ alkyl-(C=O)—$NR^{12}$—, or $C_3$-$C_6$ heterocycloalkyl-(C=O)—$NR^{12}$— comprising at least one nitrogen atom; wherein $R^{12}$ is selected from hydrogen or $C_1$-$C_3$ alkyl;

or a pharmaceutically acceptable salt, ester, or prodrug thereof.

Pharmaceutical composition comprising a therapeutically effective amount of a compound described herein or a pharmaceutically acceptable salt, ester, or prodrug thereof, and a pharmaceutically acceptable carrier are also disclosed.

In specific aspects, the disclosed subject matter relates to cancer therapy and to anti-cancer compounds. More specifically, the subject matter disclosed herein relates to inhibitors for the β-catenin/BCL9 interaction. Further, the subject matter disclosed herein relates to inhibitors that are selective for β-catenin/BCL9 over β-catenin/cadherin interactions. Also disclosed are methods of inhibiting the β-catenin/BCL9 interaction, as well as methods of treating certain cancers. In further aspects, the disclosed subject matter relates to a new benzaldehyde mediated photoredox reaction for the direct α-heteroarylation of amides and ethers. Still further, the disclosed subject matter relates to a HPLC/MS method for the determination of inhibitor cellular bioavailability.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

FIG. 1 shows representative structures of compounds described herein.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represented by the formula —N$_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modem methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

In certain aspects, disclosed herein are compounds having Formula I.

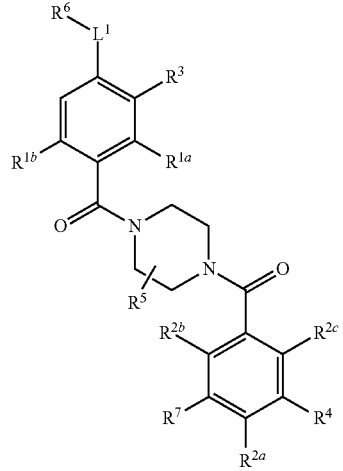

Formula I wherein $L^1$ is O, S, or NH;
wherein each of $R^{1a}$ and $R^{1b}$ is independently hydrogen, halogen, $C_1$-$C_3$ alkyl, $C_1$-$C_3$ monohaloalkyl, or $C_1$-$C_3$ polyhaloalkyl;
wherein each of $R^{2a}$, $R^{2b}$, and $R^{2c}$ is independently hydrogen, halogen, $C_1$-$C_3$ alkyl, $C_1$-$C_3$ haloalkyl, or $C_1$-$C_3$ polyhaloalkyl;
wherein $R^3$ is $Cy^3$ or $Ar^1$; wherein $Cy^3$ is a $C_3$-$C_8$ cycloalkyl or a $C_2$-$C_7$ heterocycloalkyl and Ar is selected from aryl and heteroaryl, wherein $Cy^3$ and $Ar^1$, when present, are substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —CO$_2$H;
wherein $R^4$ is hydrogen, halogen, $C_1$-$C_3$ alkyl, $C_1$-$C_3$ haloalkyl, or $C_1$-$C_3$ polyhaloalkyl;
wherein each occurrence of $R^5$ is independently selected from hydrogen, $C_1$-$C_6$ alkyl;
wherein $R^6$ is $C_1$-$C_6$ aminoalkyl, $C_1$-$C_6$ hydroxyalkyl, or $Cy^1$; and wherein $Cy^1$ is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;
wherein $R^7$ is $C_1$-$C_6$ alkyl-(C=O)—NR$^{12}$—; amino-$C_1$-$C_6$ alkyl-(C=O)—NR$^{12}$—, or $C_3$-$C_6$ heterocycloalkyl-(C=O)—NR$^{12}$— comprising at least one nitrogen atom; wherein $R^{12}$ is selected from hydrogen or $C_1$-$C_3$ alkyl;
or a pharmaceutically acceptable salt, ester, or prodrug thereof.

In some aspects of Formula I, the compound can have a structure according to Formula I-A.

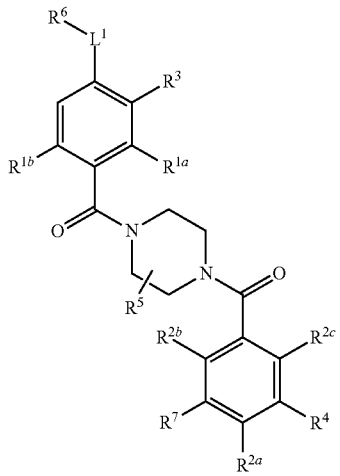

Formula I-A wherein $L^1$ is O, S, or NH;
wherein each of $R^{1a}$ and $R^{1b}$ is independently hydrogen, halogen, $C_1$-$C_3$ alkyl, $C_1$-$C_3$ monohaloalkyl, or $C_1$-$C_3$ polyhaloalkyl;
wherein each of $R^{2a}$, $R^{2b}$, and $R^{2c}$ is independently hydrogen, halogen, $C_1$-$C_3$ alkyl, $C_1$-$C_3$ haloalkyl, or $C_1$-$C_3$ polyhaloalkyl;
wherein $R^3$ is $Cy^3$ or $Ar^1$; wherein $Cy^3$ is a $C_3$-$C_8$ cycloalkyl or a $C_2$-$C_7$ heterocycloalkyl and Ar is selected from aryl and heteroaryl, wherein $Cy^3$ and $Ar^1$, when present, are substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$;
wherein $R^4$ is hydrogen, halogen, $C_1$-$C_3$ alkyl, $C_1$-$C_3$ haloalkyl, or $C_1$-$C_3$ polyhaloalkyl;
wherein each occurrence of $R^5$ is independently selected from hydrogen, $C_1$-$C_3$ alkyl;
wherein $R^6$ is $C_1$-$C_6$ aminoalkyl, $C_1$-$C_6$ hydroxyalkyl, or $Cy^1$; and wherein $Cy^1$ is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;
wherein $R^7$ is $C_1$-$C_6$ alkyl-(C=O)—$NR^{12}$—; wherein $R^{12}$ is selected from hydrogen or $C_1$-$C_3$ alkyl;
or a pharmaceutically acceptable salt, ester, or prodrug thereof.

Also disclosed are pharmaceutical compositions comprising a therapeutically effective amount of a disclosed compound, or a pharmaceutically acceptable salt, ester, or prodrug thereof, and a pharmaceutically acceptable carrier.

In one aspect of the compounds disclosed herein (including Formula I and I-A), $L^1$ is optionally present, and when present, is O, S, or NH. In a further aspect, $L^1$ is not present. In a further aspect, $L^1$ is optionally present, and when present, is O or S. In a still further aspect, $L^1$ is optionally present, and when present, is O or NH. In a yet further aspect, $L^1$ is optionally present, and when present, is S or NH. In an even further aspect, $L^1$ is optionally present, and when present, is O. In a still further aspect, $L^1$ is optionally present, and when present, is S. In a yet further aspect, $L^1$ is optionally present, and when present, is NH. In a further aspect, $L^1$ is O, S, or NH. In a still further aspect, $L^1$ is O or S. In a yet further aspect, $L^1$ is O or NH. In an even further aspect, $L^1$ is S or NH. In a still further aspect, $L^1$ is O. In a yet further aspect, $L^1$ is S. In an even further aspect, $L^1$ is NH.

In one aspect of the compounds disclosed herein (including Formula I and I-A), each of $R^{1a}$ and $R^{1b}$, when present, is independently selected from hydrogen, halogen, $C_1$-$C_3$ alkyl, $C_1$-$C_3$ monohaloalkyl, and $C_1$-$C_3$ polyhaloalkyl. In a further aspect, each of $R^{1a}$ and $R^{1b}$, when present, is hydrogen. In a further aspect, each of $R^{1a}$ and $R^{1b}$, when present, is independently selected from hydrogen and $C_1$-$C_3$ alkyl. In a still further aspect, each of $R^{1a}$ and $R^{1b}$, when present, is independently selected from hydrogen and $C_1$-$C_3$ monohaloalkyl.

In yet a further aspect, each of $R^{1a}$ and $R^{1b}$, when present, is independently selected from hydrogen and $C_1$-$C_3$ polyhaloalkyl. In a further aspect, each of $R^{1a}$ and $R^{1b}$, when present, is independently selected from hydrogen, halogen, and $C_1$-$C_3$ alkyl. In a still further aspect, each of $R^{1a}$ and $R^{1b}$, when present, is independently selected from hydrogen, halogen, and $C_1$-$C_3$ monohaloalkyl. In yet a further aspect, each of $R^{1a}$ and $R^{1b}$, when present, is independently selected from hydrogen, halogen, and $C_1$-$C_3$ polyhaloalkyl.

In a further aspect, $R^{1a}$ when present, is selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $R^{1a}$ when present, is selected from hydrogen, —F, —Cl, methyl, —$CH_2F$, —$CHF_2$, —$CF_3$, —$CHCl_2$, and —$CCl_3$. In yet a further aspect, $R^{1a}$ when present, is selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, $R^{1a}$ when present, is selected from hydrogen, methyl, —F, —$CH_2F$, —$CHF_2$, and —$CF_3$.

In a further aspect, $R^{1b}$ when present, is selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $R^{1b}$ when present, is selected from hydrogen, —F, —Cl, methyl, —$CH_2F$, —$CHF_2$, —$CF_3$, —$CHCl_2$, and —$CCl_3$. In yet a further aspect, $R^{1b}$ when present, is selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, $R^{1b}$ when present, is selected from hydrogen, methyl, —F, —$CH_2F$, —$CHF_2$, and —$CF_3$.

In a further aspect, each of $R^{1a}$ and $R^{1b}$, when present, is independently selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, each of $R^{1a}$ and $R^{1b}$, when present, is independently selected from hydrogen, —F, —Cl, methyl, —$CH_2F$, —$CHF_2$, —$CF_3$, —$CHCl_2$, and —$CCl_3$. In yet a further aspect, each of $R^{1a}$ and $R^{1b}$, when present, is independently selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, each of $R^{1a}$ and $R^{1b}$, when present, is independently selected from hydrogen, methyl, —F, —$CH_2F$, —$CHF_2$, and —$CF_3$.

In one aspect of the compounds disclosed herein (including Formula I and I-A), each of $R^{2a}$, $R^{2b}$ and $R^{2c}$, when present, is independently selected from hydrogen, halogen, $C_1$-$C_3$ alkyl, $C_1$-$C_3$ monohaloalkyl, and $C_1$-$C_3$ polyhaloalkyl. In a further aspect, each of $R^{2a}$, $R^{2b}$ and $R^{2c}$, when present, is hydrogen.

In a further aspect, each of $R^{2a}$, $R^{2b}$ and $R^{2c}$, when present, is independently selected from hydrogen and $C_1$-$C_3$ alkyl. In a still further aspect, each of $R^{2a}$, $R^{2b}$ and $R^{2c}$, when present, is independently selected from hydrogen and $C_1$-$C_3$ monohaloalkyl. In yet a further aspect, each of $R^{2a}$, $R^{2b}$ and $R^{2c}$, when present, is independently selected from hydrogen and $C_1$-$C_3$ polyhaloalkyl.

In a further aspect, each of $R^{2a}$, $R^{2b}$ and $R^{2c}$, when present, is independently selected from hydrogen, halogen, and $C_1$-$C_3$ alkyl. In a still further aspect, each of $R^{2a}$, $R^{2b}$ and $R^{2c}$, when present, is independently selected from hydrogen, halogen, and $C_1$-$C_3$ monohaloalkyl. In yet a further aspect, each of $R^{2a}$, $R^{2b}$ and $R^{2c}$, when present, is independently selected from hydrogen, halogen, and $C_1$-$C_3$ polyhaloalkyl.

In a further aspect, $R^{2a}$ when present, is selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^{2a}$ when present, is selected from hydrogen, —F, —Cl, methyl, —CH$_2$F, —CHF$_2$, —CF$_3$, —CHCl$_2$, and —CCl$_3$. In yet a further aspect, $R^{2a}$ when present, is selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, $R^{2a}$ when present, is selected from hydrogen, methyl, —F, —CH$_2$F, —CHF$_2$, and —CF$_3$.

In a further aspect, $R^{2b}$ when present, is selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^{2b}$ when present, is selected from hydrogen, —F, —Cl, methyl, —CH$_2$F, —CHF$_2$, —CF$_3$, —CHCl$_2$, and —CCl$_3$. In yet a further aspect, $R^{2b}$ when present, is selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, $R^{2b}$ when present, is selected from hydrogen, methyl, —F, —CH$_2$F, —CHF$_2$, and —CF$_3$.

In a further aspect, $R^{2c}$ when present, is selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^{2c}$ when present, is selected from hydrogen, —F, —Cl, methyl, —CH$_2$F, —CHF$_2$, —CF$_3$, —CHCl$_2$, and —CCl$_3$. In yet a further aspect, $R^{2c}$ when present, is selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, $R^{2c}$ when present, is selected from hydrogen, methyl, —F, —CH$_2$F, —CHF$_2$, and —CF$_3$.

In a further aspect, each of $R^{2a}$, $R^{2b}$ and $R^{2c}$, when present, is independently selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, each of $R^{2a}$, $R^{2b}$ and $R^{2c}$, when present, is independently selected from hydrogen, —F, —Cl, methyl, —CH$_2$F, —CHF$_2$, —CF$_3$, —CHCl$_2$, and —CCl$_3$. In yet a further aspect, each of $R^{2a}$, $R^{2b}$ and $R^{2c}$, when present, is independently selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, each of $R^{2a}$, $R^{2b}$ and $R^{2c}$, when present, is independently selected from hydrogen, methyl, —F, —CH$_2$F, —CHF$_2$, and —CF$_3$.

In one aspect of the compounds disclosed herein (including Formula I and I-A), $R^3$ is $Cy^3$ or $Ar^1$; wherein $Cy^3$ is a $C_3$-$C_8$ cycloalkyl or a $C_2$-$C_7$ heterocycloalkyl and Ar is selected from aryl and heteroaryl. In further aspect, $R^3$ is selected from $C_5$-$C_7$ cycloalkyl, or $C_5$-$C_7$ cycloalkenyl, and wherein $R^3$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, or $R^{10a}$NHCO— (substituted carbamoyl group), —NHCOR$^{10a}$, —NHSO$_2$R$^{10a}$, —CONR$^{12a}$R$^{12b}$, —SO$_2$NR$^{12a}$R$^{12b}$, —CO$_2$H, and tetrazole. In further examples, $R^3$ is selected from cyclopentyl, cyclohexyl, or cycloheptyl. In a specific example, $R^3$ is cyclohexyl. In other examples, $R^3$ is selected from cyclopentenyl, cyclohexenyl, cycloheptenyl. In a specific example, $R^3$ is cyclohexenyl. In a still further aspect, $R^3$ is substituted with 0 or 1 group selected from halogen, —CN, $C_1$-$C_3$ alkyl, $C_1$-$C_3$ monohaloalkyl, $C_1$-$C_3$ polyhaloalkyl. In yet a further aspect, $R^3$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and $R^{10}$NHCO—. In an even further aspect, $R^3$ is unsubstituted.

In a further aspect, $R^3$ is cyclohexyl, and wherein $R^3$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and $R^{10}$NHCO— ($R^{10}$ substituted carbamoyl group). In a still further aspect, $R^3$ is cyclohexenyl, and wherein $R^3$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and $R^{10a}$NHCO—. In yet a further aspect, $R^3$ is cyclohexyl, and wherein $R^3$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and —CO$_2$H. In an even further aspect, $R^3$ is cyclohexyl, and wherein $R^3$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —CO$_2$H. In a still further aspect, $R^3$ is cyclohexyl, and wherein $R^3$ is unsubstituted.

In a further aspect, $R^3$ is cyclohexenyl, and wherein $R^3$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and $R^{10a}$NHCO—. In a still further aspect, $R^3$ is cyclohexenyl, and wherein $R^3$ is substituted with 0, 1, or 2 groups independently selected from halogen, —CN, $C_1$-$C_3$ alkyl, $C_1$-$C_3$ monohaloalkyl, $C_1$-$C_3$ polyhaloalkyl, cyclopropyl, and $R^{10a}$NHCO—. In yet a further aspect, $R^3$ is cyclohexenyl, and wherein $R^3$ is substituted with 0 or 1 group selected from halogen, —CN, $C_1$-$C_3$ alkyl, $C_1$-$C_3$ monohaloalkyl, $C_1$-$C_3$ polyhaloalkyl, cyclopropyl, and $R^{10a}$NHCO—. In an even further aspect, $R^3$ is cyclohexenyl, and wherein $R^3$ is monosubstituted with a group selected from halogen, —CN, $C_1$-$C_3$ alkyl, $C_1$-$C_3$ monohaloalkyl, $C_1$-$C_3$ polyhaloalkyl, cyclopropyl, and —CO$_2$H. In a still further aspect, $R^3$ is cyclohexenyl, and wherein $R^3$ is unsubstituted.

In one aspect of the compounds disclosed herein (including Formula I and I-A), $R^4$ is hydrogen, halogen, $C_1$-$C_3$ alkyl, $C_1$-$C_3$ monohaloalkyl, $C_1$-$C_3$ polyhaloalkyl, or $R^{15}$CONH—. In a further aspect, $R^4$ is hydrogen. In a further aspect, $R^4$ is selected from hydrogen and $C_1$-$C_3$ alkyl. In a still further aspect, $R^4$ is selected from hydrogen and $C_1$-$C_3$ monohaloalkyl. In yet a further aspect, $R^4$ is selected from hydrogen and $C_1$-$C_3$ polyhaloalkyl.

In a further aspect, $R^4$ is selected from hydrogen, halogen, and $C_1$-$C_3$ alkyl. In a still further aspect, $R^4$ is selected from hydrogen, halogen, and $C_1$-$C_3$ monohaloalkyl. In yet a further aspect, $R^4$ is selected from hydrogen, halogen, and $C_1$-$C_3$ polyhaloalkyl.

In a further aspect, $R^4$ is selected from hydrogen, methyl, ethyl, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $R^4$ is selected from hydrogen, —F, —Cl, methyl, —$CH_2F$, —$CHF_2$, —$CF_3$, —$CHCl_2$, and —$CCl_3$. In yet a further aspect, $R^4$ is selected from hydrogen, methyl, ethyl, —F, —$CH_2F$, —$CH_2CH_2F$, —$CHF_2$, —$CF_3$, —$CH_2CHF_2$, and —$CH_2CF_3$. In an even further aspect, $R^4$ is selected from hydrogen, methyl, —F, —$CH_2F$, —$CHF_2$, and —$CF_3$.

In a further aspect, $R^4$ is —F, —Cl —Br, methyl, ethyl, —$CFH_2$, —$CF_2H$, or —$CF_3$. In a further aspect, $R^4$ is —F, —Cl, —Br, methyl, or —$CF_3$.

In one aspect of the compounds disclosed herein (including Formula I and I-A), $R^5$ is selected from hydrogen, $C_1$-$C_6$ alkyl. In further aspects, $R^5$ is hydrogen, methyl, ethyl, propyl, isopropyl, butyl, or isobutyl. In a further aspect, $R^5$ is hydrogen.

In one aspect, $R^5$ is hydrogen, halogen, $C_1$-$C_8$ alkyl, $C_1$-$C_8$ monohaloalkyl, $C_1$-$C_8$ polyhaloalkyl, or $R^{14}CONH$—. In one aspect, $R^5$ is hydrogen, halogen, $C_1$-$C_3$ alkyl, $C_1$-$C_3$ monohaloalkyl, $C_1$-$C_3$ polyhaloalkyl, or $R^{14}CONH$—. In a further aspect, $R^5$ is hydrogen. In a further aspect, $R^5$ is selected from hydrogen and $C_1$-$C_3$ alkyl. In a still further aspect, $R^5$ is selected from hydrogen and $C_1$-$C_3$ monohaloalkyl. In yet a further aspect, $R^5$ is selected from hydrogen and $C_1$-$C_3$ polyhaloalkyl.

In a further aspect, $R^5$ is selected from hydrogen, halogen, and $C_1$-$C_3$ alkyl. In a still further aspect, $R^5$ is selected from hydrogen, halogen, and $C_1$-$C_3$ monohaloalkyl. In yet a further aspect, $R^5$ is selected from hydrogen, halogen, and $C_1$-$C_3$ polyhaloalkyl.

In one aspect of the compounds disclosed herein (including Formula I and I-A), $R^6$ is selected from $C_1$-$C_6$ aminoalkyl, $C_1$-$C_6$ hydroxyalkyl, or $Cy^1$; and wherein $Cy^1$ is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, —CN, $C_1$-$C_3$ alkyl, $C_1$-$C_3$ monohaloalkyl, and $C_1$-$C_3$ polyhaloalkyl. In further aspect, $R^6$ is selected from —($C_2$-$C_6$ alkyl)-OH, —($C_2$-$C_6$ alkyl)-$NH_2$, —NH—($C_2$-$C_8$ alkyl)-OH, —NH—($C_2$-$C_8$ alkyl)-$NH_2$, —NH-$Cy^1$, and —$NHCH_2$—$Cy^1$.

In one aspect of the compounds disclosed herein (including Formula I and I-A), $R^7$ is $C_1$-$C_6$ alkyl-(C=O)—$NR^{12}$—; amino-$C_1$-$C_6$ alkyl-(C=O)—$NR^{12}$—, or $C_3$-$C_6$ heterocycloalkyl-(C=O)—$NR^{12}$— comprising at least one nitrogen atom; wherein $R^{12}$ is selected from hydrogen or $C_1$-$C_3$ alkyl. In further aspect, $R^7$ is $C_3$-$C_6$ heterocycloalkyl-(C=O)—$NR^{12}$-$Cy^5$, wherein the heterocycloalkyl is piperidinyl substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, the heterocycloalkyl is piperidinyl substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, the heterocycloalkyl is piperidinyl substituted with 0 or 1 group selected from halogen, $C_1$-$C_4$ alkyl, $C_1$-$C_4$ monohaloalkyl, and $C_1$-$C_4$ polyhaloalkyl. In an even further aspect, the heterocycloalkyl is piperidinyl monosubstituted with a group selected from halogen, $C_1$-$C_4$ alkyl, $C_1$-$C_4$ monohaloalkyl, and $C_1$-$C_4$ polyhaloalkyl. In a still further aspect, the heterocycloalkyl is unsubstituted piperidinyl.

In further aspects, $R^7$ is $CH_3$—(C=O)—$NR^{12}$—; $CH_3CH_2$—(C=O)—$NR^{12}$—; $CH_3CH_2CH_2$—(C=O)—$NR^{12}$—; or $CH_3CH_2CH_2CH_2$—(C=O)—$NR^{12}$—.

In further aspects, $R^7$ is $NH_2$—$(CH_2)_n$—(C=O)—$NR^{12}$—, wherein n is from 1 to 6 or from 1 to 4. For example, $R^7$ is $NH_2$—$CH_2$—(C=O)—$NR^{12}$—, $NH_2$—$CH_2CH_2$—(C=O)—$NR^{12}$—, $NH_2$—$CH_2CH_2CH_2$—(C=O)—$NR^{12}$—, $NH_2$—$CH_2CH_2CH_2CH_2$—(C=O)—$NR^{12}$—, $NH_2$—$CH(CH_3)CH_2CH_2CH_2$—(C=O)—$NR^{12}$—, $NH_2$—$CH(CH_3)CH_2CH_2$—(C=O)—$NR^{12}$—, $NH_2$—$CH(CH_3)CH_2$—(C=O)—$NR^{12}$—, $NH_2$—$CH_2CH(CH_3)CH_2CH_2$—(C=O)—$NR^{12}$—, $NH_2$—$CH_2CH(CH_3)CH_2$—(C=O)—$NR^{12}$—, $NH_2$—$CH_2CH(CH_3)$—(C=O)—$NR^{12}$—, $NH_2$—$CH_2CH_2CH(CH_3)CH_2$—(C=O)—$NR^{12}$—, or $NH_2$—$CH_2CH_2CH(CH_3)$—(C=O)—$NR^{12}$—.

In one aspect of the compounds disclosed herein (including Formula I and I-A), each of $R^{10a}$ and $R^{10b}$ is independently hydrogen, methyl, ethyl, propyl, or isopropyl. In a further aspect, each of $R^{10a}$ and $R^{10b}$ is independently hydrogen. In a further aspect, each of $R^{10a}$ and $R^{10b}$ is independently hydrogen, methyl, or ethyl. In a still further aspect, each of $R^{10a}$ and $R^{10b}$ is independently hydrogen or methyl. In a yet further aspect, each of $R^{10a}$ and $R^{10b}$ is independently hydrogen, ethyl, propyl, or isopropyl. In an even further aspect, each of $R^{10a}$ and $R^{10b}$ is independently hydrogen or ethyl. In a still further aspect, each of $R^{10a}$ and $R^{10b}$ is independently hydrogen, propyl, or isopropyl. Each of $R^{10a}$ and $R^{10b}$ is independently hydrogen or propyl. In a yet further aspect, each of $R^{10a}$ and $R^{10b}$ is independently hydrogen or isopropyl. In a further aspect, each of $R^{10a}$ and $R^{10b}$ is independently is methyl or ethyl. In a still further aspect, each of $R^{10a}$ and $R^{10b}$ is independently methyl. In a yet further aspect, each of $R^{10a}$ and $R^{10b}$ is independently ethyl, propyl, or isopropyl. In an even further aspect, each of $R^{10a}$ and $R^{10b}$ is independently s ethyl. In a still further aspect, each of $R^{10a}$ and $R^{10b}$ is independently is propyl or isopropyl. In a yet further aspect, each of $R^{10a}$ and $R^{10b}$ is independently hydrogen.

In one aspect, $R^{10a}$ is selected from hydrogen, methyl, ethyl, propyl, or isopropyl. In a further aspect, $R^{10a}$ is selected from hydrogen. In a further aspect, $R^{10a}$ is selected from hydrogen, methyl, or ethyl. In a still further aspect, $R^{10a}$ is selected from hydrogen or methyl. In a yet further aspect, $R^{10a}$ is selected from hydrogen, ethyl, propyl, or isopropyl. In an even further aspect, $R^{10a}$ is selected from hydrogen or ethyl. In a still further aspect, $R^{10a}$ is selected from hydrogen, propyl, or isopropyl. $R^{10a}$ can be selected from hydrogen or propyl. In a yet further aspect, $R^{10a}$ is selected from hydrogen or isopropyl. In a further aspect, $R^{10a}$ is selected from is methyl or ethyl. In a still further aspect, $R^{10a}$ is selected from methyl. In a yet further aspect, $R^{10a}$ is selected from ethyl, propyl, or isopropyl. In an even further aspect, $R^{10a}$ is selected from ethyl. In a still further aspect, $R^{10a}$ is selected from is propyl or isopropyl. In a yet further aspect, $R^{10a}$ is selected from hydrogen.

In one aspect, $R^{10b}$ is selected from hydrogen, methyl, ethyl, propyl, or isopropyl. In a further aspect, $R^{10b}$ is selected from hydrogen. In a further aspect, $R^{10b}$ is selected from hydrogen, methyl, or ethyl. In a still further aspect, $R^{10b}$ is selected from hydrogen or methyl. In a yet further aspect, $R^{10b}$ is selected from hydrogen, ethyl, propyl, or isopropyl. In an even further aspect, $R^{10b}$ is selected from hydrogen or ethyl. In a still further aspect, $R^{10b}$ is selected from hydrogen, propyl, or isopropyl. $R^{10b}$ can be selected from hydrogen or propyl. In a yet further aspect, $R^{10b}$ is selected from hydrogen or isopropyl. In a further aspect, $R^{10b}$ is selected from is methyl or ethyl. In a still further aspect, $R^{10b}$ is selected from methyl. In a yet further aspect, $R^{10b}$ is selected from ethyl, propyl, or isopropyl. In an even further aspect, $R^{10b}$ is selected from ethyl. In a still further aspect, $R^{10b}$ is selected from is propyl or isopropyl. In a yet further aspect, $R^{10b}$ is selected from hydrogen.

In one aspect of the compounds disclosed herein (including Formula I and I-A), $R^{12}$ is hydrogen, methyl, ethyl, propyl, or isopropyl. For example, $R^{12}$ can be hydrogen or methyl. In other examples, $R^{12}$ can be hydrogen.

In one aspect of the compounds disclosed herein (including Formula I and I-A), $R^{15}$ is hydrogen, $C_1$-$C_3$ alkyl, $C_1$-$C_3$ monohaloalkyl, or $C_1$-$C_3$ polyhaloalkyl. In further aspect, $R^{15}$ is hydrogen, methyl, ethyl, propyl, or isopropyl. In a further aspect, $R^{15}$ is selected from hydrogen, methyl, ethyl, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^{15}$ is selected from hydrogen, —F, —Cl, methyl, —CH$_2$F, —CHF$_2$, —CF$_3$, —CHCl$_2$, and —CCl$_3$. In yet a further aspect, $R^{15}$ is selected from hydrogen, methyl, ethyl, —F, —CH$_2$F, —CH$_2$CH$_2$F, —CHF$_2$, —CF$_3$, —CH$_2$CHF$_2$, and —CH$_2$CF$_3$. In an even further aspect, $R^{15}$ is selected from hydrogen, methyl, —F, —CH$_2$F, —CHF$_2$, and —CF$_3$. In a further aspect, $R^{15}$ is hydrogen.

In one aspect of the compounds disclosed herein (including Formula I and I-A), $R^{15}$ is $Ar^2$, wherein $Ar^2$ is selected from aryl, heteroaryl, and wherein $Ar^2$ is substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl.

In one aspect of the compounds disclosed herein (including Formula I and I-A), $Cy^1$, when present, is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, —CN, $C_1$-$C_3$ alkyl, $C_1$-$C_3$ monohaloalkyl, and $C_1$-$C_3$ polyhaloalkyl. In a further aspect, $Cy^1$, when present, is a $C_2$-$C_7$ heterocycloalkyl comprising at least one oxygen or nitrogen atom, and wherein $Cy^1$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is a $C_2$-$C_7$ heterocycloalkyl comprising at least one oxygen or nitrogen atom, and wherein $Cy^1$ is substituted with 0 or 1 group selected from halogen, $C_1$-$C_4$ alkyl, $C_1$-$C_4$ monohaloalkyl, and $C_1$-$C_4$ polyhaloalkyl. In yet a further aspect, $Cy^1$, when present, is a $C_2$-$C_7$ heterocycloalkyl comprising at least one oxygen or nitrogen atom, and wherein $Cy^1$ is monosubstituted with a group selected from halogen, $C_1$-$C_4$ alkyl, $C_1$-$C_4$ monohaloalkyl, and $C_1$-$C_4$ polyhaloalkyl. In an even further aspect, $Cy^1$, when present, is an unsubstituted $C_2$-$C_7$ heterocycloalkyl comprising at least one oxygen or nitrogen atom.

In a further aspect, $Cy^1$, when present, is a $C_2$-$C_6$ heterocycloalkyl comprising at least one oxygen or nitrogen atom, and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is a $C_2$-$C_6$ heterocycloalkyl comprising at least one oxygen or nitrogen atom, and wherein $Cy^1$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^1$, when present, is a $C_2$-$C_6$ heterocycloalkyl comprising at least one oxygen or nitrogen atom, and wherein $Cy^1$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^1$, when present, is a $C_2$-$C_6$ heterocycloalkyl comprising at least one oxygen or nitrogen atom, and wherein $Cy^1$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^1$, when present, is an unsubstituted $C_2$-$C_6$ heterocycloalkyl comprising at least one oxygen or nitrogen atom.

In a further aspect, $Cy^1$, when present, is a $C_2$-$C_5$ heterocycloalkyl comprising at least one oxygen or nitrogen atom, and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is a $C_2$-$C_5$ heterocycloalkyl comprising at least one oxygen or nitrogen atom, and wherein $Cy^1$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^1$, when present, is a $C_2$-$C_5$ heterocycloalkyl comprising at least one oxygen or nitrogen atom, and wherein $Cy^1$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^1$, when present, is a $C_2$-$C_5$ heterocycloalkyl comprising at least one oxygen or nitrogen atom, and wherein $Cy^1$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^1$, when present, is an unsubstituted $C_2$-$C_5$ heterocycloalkyl comprising at least one oxygen or nitrogen atom.

In a further aspect, $Cy^1$, when present, is a $C_2$-$C_4$ heterocycloalkyl comprising at least one oxygen or nitrogen atom, and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is a $C_2$-$C_4$ heterocycloalkyl comprising at least one oxygen or nitrogen atom, and wherein $Cy^1$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^1$, when present, is a $C_2$-$C_4$ heterocycloalkyl comprising at least one oxygen or nitrogen atom, and wherein $Cy^1$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^1$, when present, is a $C_2$-$C_4$ heterocycloalkyl comprising at least one oxygen or nitrogen atom, and wherein $Cy^1$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^1$, when present, is an unsubstituted $C_2$-$C_4$ heterocycloalkyl comprising at least one oxygen or nitrogen atom.

In a further aspect, $Cy^1$, when present, is a $C_4$ heterocycloalkyl comprising at least one oxygen or nitrogen atom, and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is a $C_4$ heterocycloalkyl comprising at least one oxygen or nitrogen atom, and wherein $Cy^1$ is substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^1$, when present, is a $C_4$ heterocycloalkyl comprising at least one oxygen or nitrogen atom, and wherein $Cy^1$ is substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^1$, when present, is a $C_4$ heterocycloalkyl comprising at least one oxygen or nitrogen atom, and wherein $Cy^1$ is monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^1$, when present, is an unsubstituted $C_4$ heterocycloalkyl comprising at least one oxygen or nitrogen atom.

In a further aspect, $Cy^1$, when present, is pyrrolidinyl substituted with 0, 1, 2, or 3 groups independently selected from halogen, $C_1$-$C_4$ alkyl, $C_1$-$C_4$ monohaloalkyl, and $C_1$-$C_4$ polyhaloalkyl. In a still further aspect, $Cy^1$, when present, is pyrrolidinyl substituted with 0, 1, or 2 groups independently selected from halogen, $C_1$-$C_4$ alkyl, $C_1$-$C_4$ monohaloalkyl, and $C_1$-$C_4$ polyhaloalkyl. In yet a further aspect, $Cy^1$, when present, is pyrrolidinyl substituted with 0 or 1 group selected from halogen, $C_1$-$C_4$ alkyl, $C_1$-$C_4$ monohaloalkyl, and $C_1$-$C_4$ polyhaloalkyl. In an even further aspect, $Cy^1$, when present, is pyrrolidinyl monosubstituted with a group selected from halogen, $C_1$-$C_4$ alkyl, $C_1$-$C_4$ monohaloalkyl, and $C_1$-$C_4$ polyhaloalkyl. In a still further aspect, $Cy^1$, when present, is an unsubstituted pyrrolidinyl.

In a further aspect, $Cy^1$, when present, is pyrrolidinyl substituted with 0, 1, 2, or 3 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a still further aspect, $Cy^1$, when present, is pyrrolidinyl substituted with 0, 1, or 2 groups independently selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $Cy^1$, when present, is pyrrolidinyl substituted with 0 or 1 group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In an even further aspect, $Cy^1$, when present, is pyrrolidinyl monosubstituted with a group selected from halogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$.

In a further aspect, $Cy^1$, when present, is pyrrolidinyl substituted with 0, 1, 2, or 3 groups independently selected from —F, —Cl, methyl, —$CH_2F$, —$CH_2Cl$, —$CHF_2$, —$CF_3$, —$CHCl_2$, and —$CCl_3$. In a still further aspect, $Cy^1$, when present, is pyrrolidinyl substituted with 0, 1, or 2 groups independently selected from —F, —Cl, methyl, —$CH_2F$, —$CH_2Cl$, —$CHF_2$, —$CF_3$, —$CHCl_2$, and —$CCl_3$. In yet a further aspect, $Cy^1$, when present, is pyrrolidinyl substituted with 0 or 1 group selected from —F, —Cl, methyl, —$CH_2F$, —$CH_2Cl$, —$CHF_2$, —$CF_3$, —$CHCl_2$, and —$CCl_3$. In an even further aspect, $Cy^1$, when present, is pyrrolidinyl monosubstituted with a group selected from —F, —Cl, methyl, —$CH_2F$, —$CH_2Cl$, —$CHF_2$, —$CF_3$, —$CHCl_2$, and —$CCl_3$.

In one aspect of the compounds disclosed herein (including Formula I and I-A), $Cy^3$, when present, is a $C_3$-$C_8$ cycloalkyl or hydroxy $C_3$-$C_8$ cycloalkyl, and wherein $Cy^3$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl.

In specific examples, disclosed herein are compounds having the following structure.

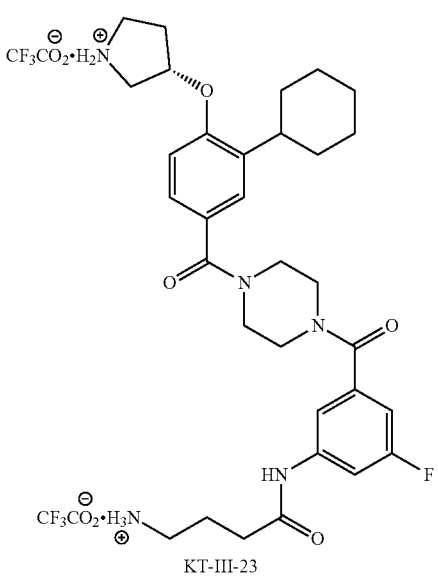

KT-III-23

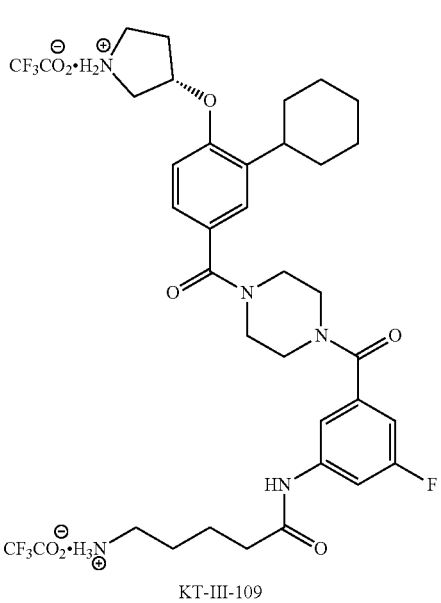

KT-III-109

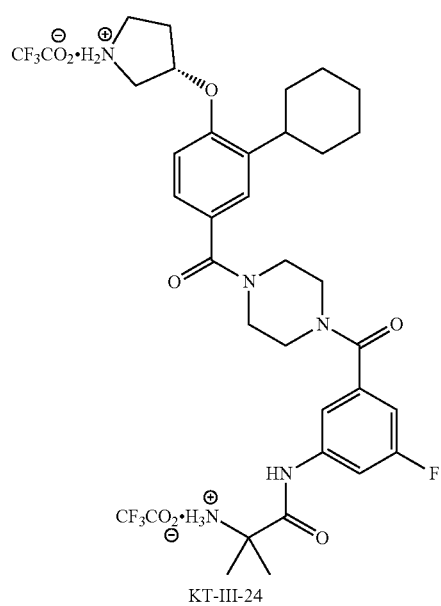
KT-III-24
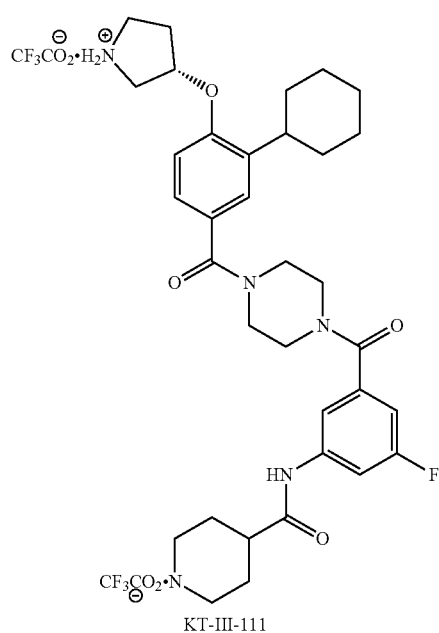
KT-III-111
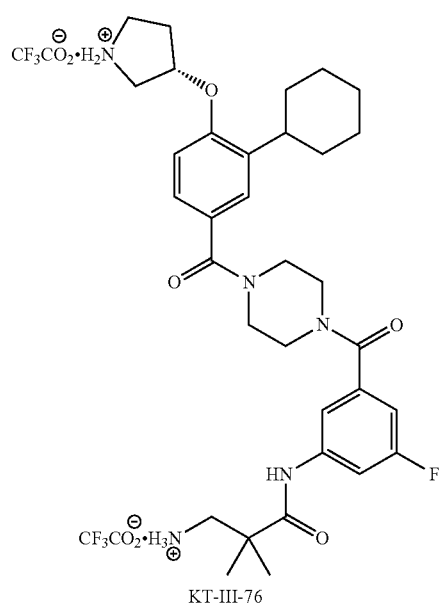
KT-III-76
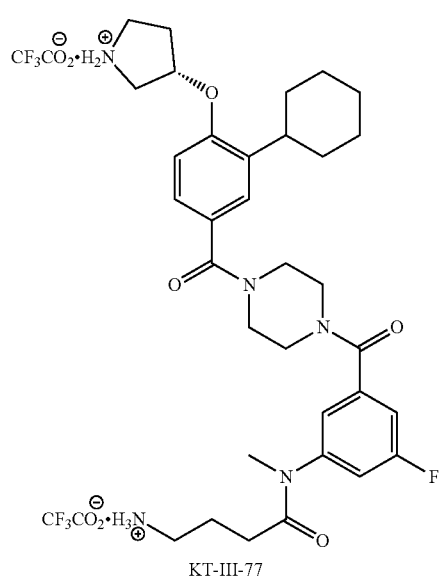
KT-III-77

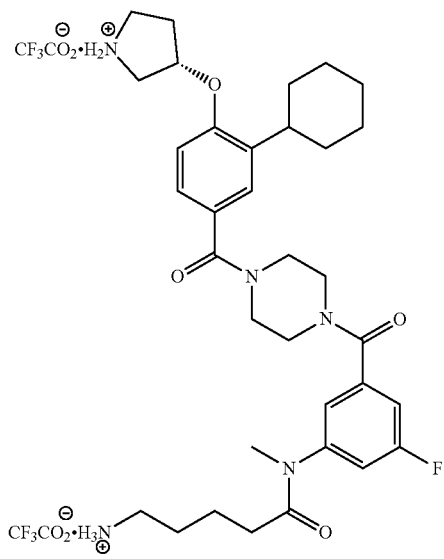
KT-III-115
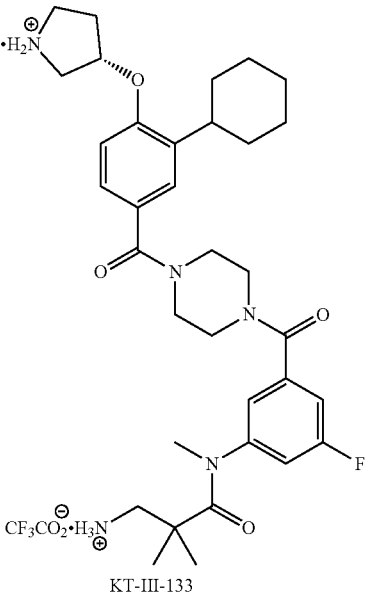
KT-III-133
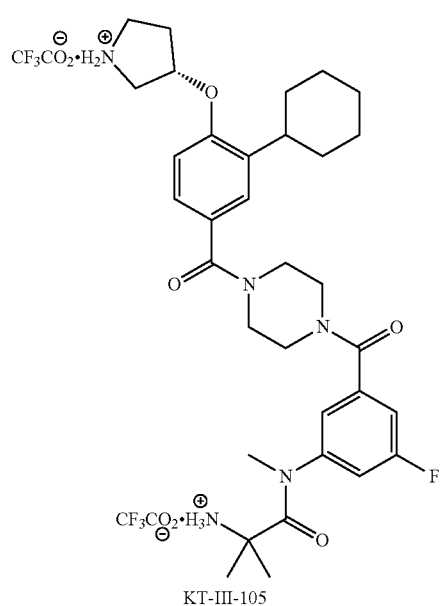
KT-III-105
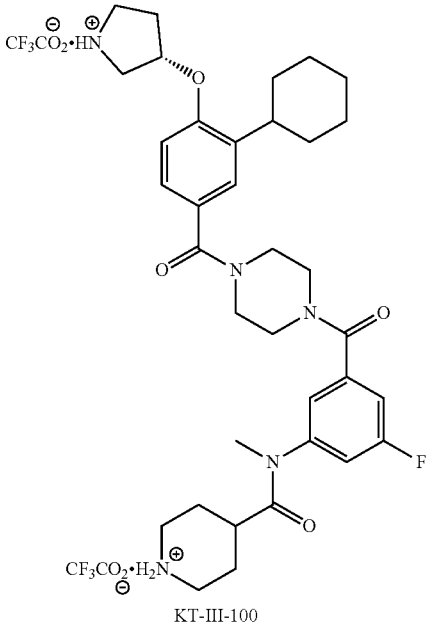
KT-III-100

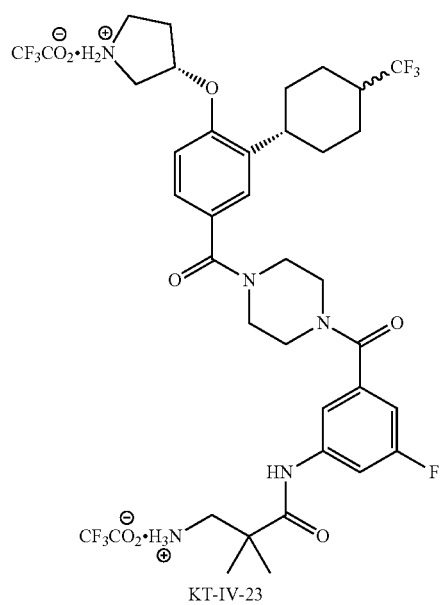
KT-IV-23
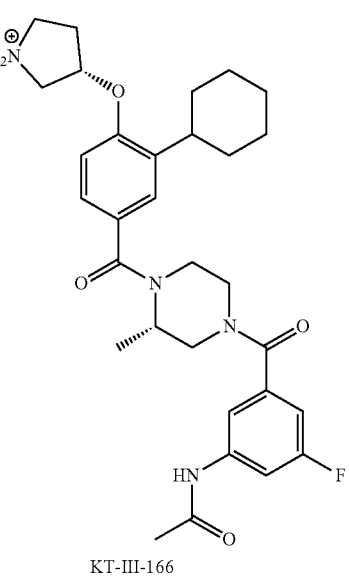
KT-III-166
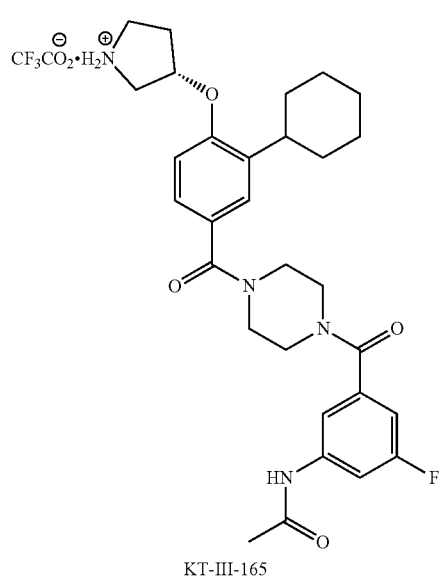
KT-III-165
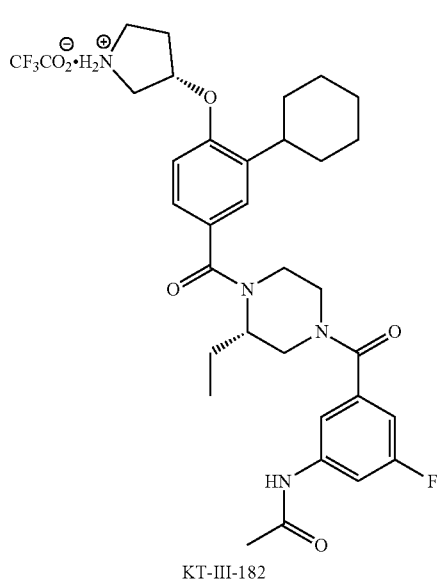
KT-III-182

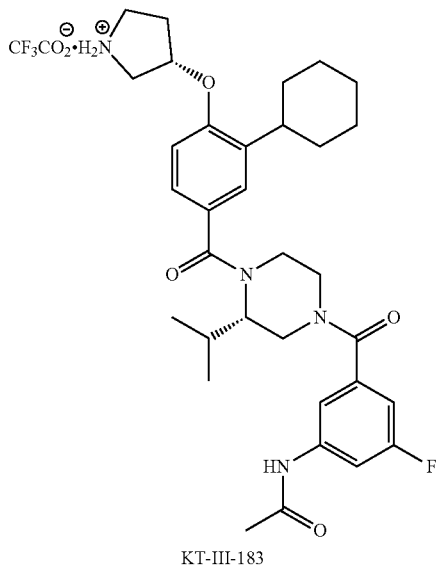

KT-III-183

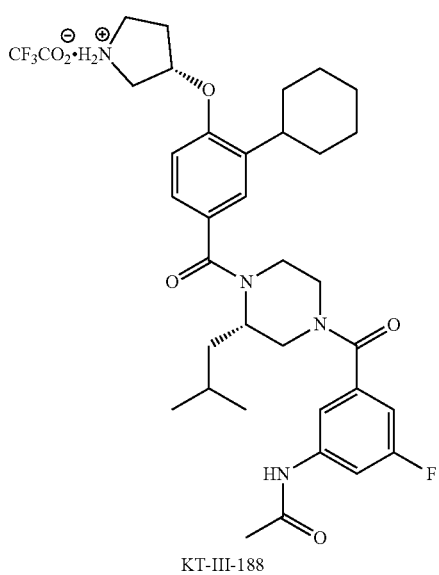

KT-III-188

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is TNBC.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Vims (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a vims that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex vims in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Chemistry: All experiments were conducted under anhydrous conditions in an atmosphere of argon, using flame-dried apparatus and employing standard techniques in handling air sensitive materials. Dichloromethane ($CH_2Cl_2$), acetonitrile ($CH_3CN$), tetrahydrofuran (THF), and dimethylformamide (DMF) were degassed with nitrogen and passed through JC Meyer solvent systems. All reagents were purchased from Sigma-Aldrich or Combi Blocks and used as received. Aqueous solutions of sodium bicarbonate ($NaHCO_3$), sodium chloride (brine), and ammonium chloride ($NH_4Cl$) were saturated. Analytical thin layer chromatography was visualized by ultraviolet light at 254 nm. Flash chromatography was performed on SilicaFlash® F60 silica gel (230-400 mesh). $^1H$ and $^{13}C$ NMR spectra were recorded using a Varian VXR 500 (500 MHz) or a Varian Unity Inova 400 (400 MHz) at the University of Utah NMR center, a Varian direct drive (VNMRS) 500 (500 MHz) at the University of South Florida Interdisciplinary NMR Facility, or a Bruker Ascend 500 (500 MHz) at the H. Lee Moffitt Cancer Center and Research Institute. The $^1H$ and $^{13}C$ NMR spectra were referenced to the residual solvent signals (7.26 ppm for $^1H$ and 77.16 ppm for $^{13}C$ in $CDCl_3$; 2.50 ppm for $^1H$ and 39.52 ppm for $^{13}C$ in DMSO-$d_6$; 2.05 ppm for $^1H$ and 29.83 ($CH_3$) 206.26 (C=O) for $^{13}C$ in $(CD_3)_2CO$). Low-resolution (LRMS) mass spectra were determined on a Waters Acquity TQD at the University of Utah, Department of Chemistry Mass Spectrometry Facility or an Agilent 1220 HPLC with an Agilent 6120 Quadrupole mass spectrometry (MS) detector at the H. Lee Moffitt Cancer Center and Research Institute. High-resolution mass spectra were determined on the Agilent G6230BA TOF LCMS Mass Spectrometer with a TOF mass detector.

The synthesis of 103a,b has been reported in the previous publication (Wisniewski, J. A.; Yin, J.; Teuscher, K. B.; Zhang, M.; Ji, H. Structure-based design of 1,4-dibenzoylpiperazines as β-catenin/B-cell lymphoma 9 protein-protein interaction inhibitors. *ACS Med. Chem. Lett.* 2016, 7, 508-513). The synthetic route for 1-5 is shown in Scheme 1. For this synthetic route the common reaction procedures for each derivative have been reported as general procedures A-C, E and F. After the methyl esterification of the starting material, 3-amino-5-fluorobenzoic acid, Compound 104 underwent amide bond coupling, general procedure A, with Boc protected amino acids a-c, and e to yield 105a-c, and e in moderate to good yield. For 3-((tert-butoxycarbony 1) amino)-2,2-dimethylpropanoic acid (105d), the formation of the acyl chloride with Ghosez reagent (1-chloro-V, V-2-trimethyl-1-propenylamine) followed by nucleophilic substitution of 104 produced 105d in moderate yield. The methyl ester of 105a-e was hydrolyzed, general procedure B, and then coupled with 1-Cbz-piperazine, general procedure C, to produce 107a-e in good yield. Compounds 107a-e underwent Cbz deprotection through hydrogenation followed by amide bond coupling, general procedure E, with 103a to produce 108a-e. The Boc deprotection of 108a-e with TFA, general procedure F, produced the final products 1-5.

Scheme 1: synthetic route for compounds 1-5.

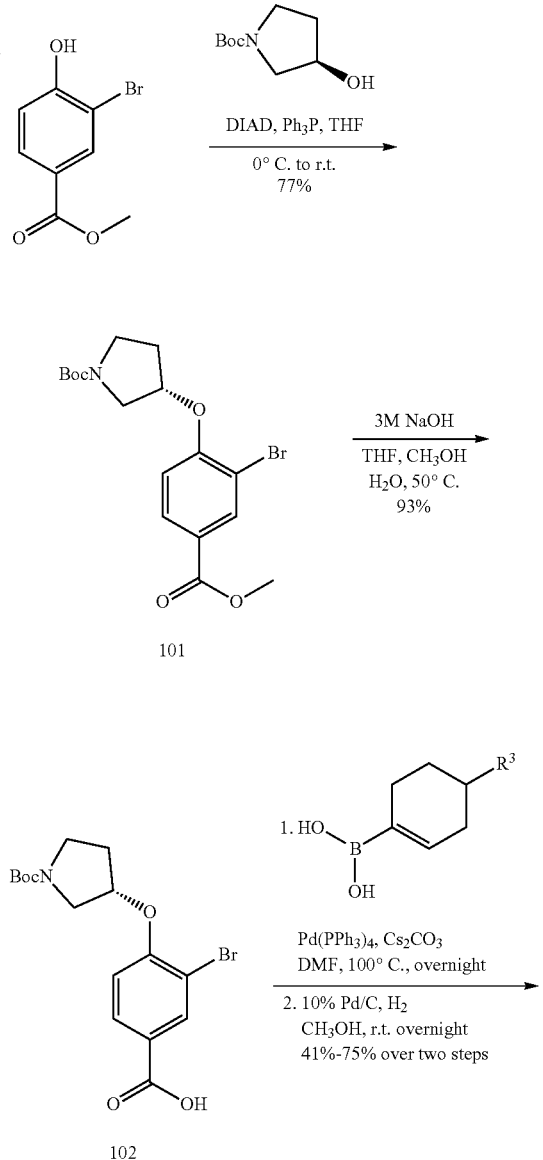

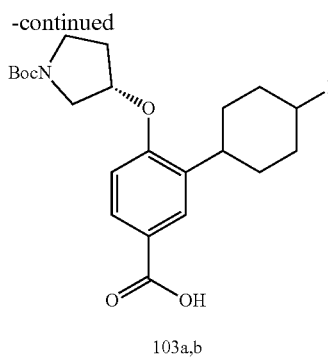

103a,b a. R³ = H
b. R³ = CF₃

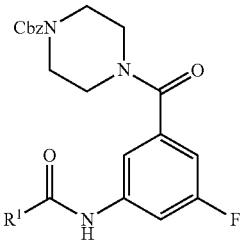

107a-e

1. H₂, 10% Pd/C
   MeOH
2. 103a
   HATU, iPr₂NEt
   CH₂Cl₂:DMF, 0° C. to r.t.
   47%-77%
   over two steps
   General Procedure D

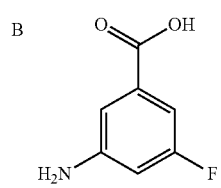

SOCl₂
MeOH, 70° C.
95%

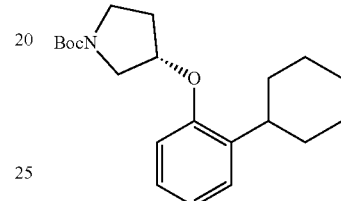

General Procedure A
HATU, iPr₂NEt
CH₂Cl₂:DMF, 0° C. to r.t.
45%-quant.
or
Ghosez reagent
CH₂Cl₂, 0° C.
Then 104, iPr₂NEt
THF, r.t. to 50° C.
38%

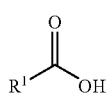

104

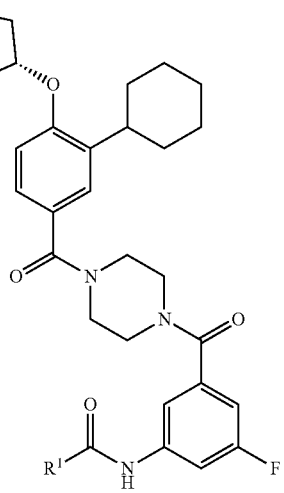

108a-e

TFA:CH₂Cl₂
0° C. to r.t.
83%-99%
General Procedure E

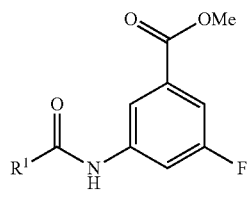

105a-e

1M NaOH
THF:MeOH
0° C. to r.t.
51%-96%
General Procedure B

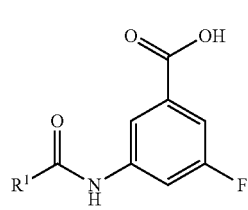

106a-e

HN⌐NCbz

HATU, iPr₂NEt
CH₂Cl₂:DMF, 0° C. to r.t.
60%-quant
General Procedure C

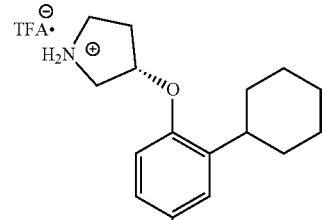

1-5

-continued

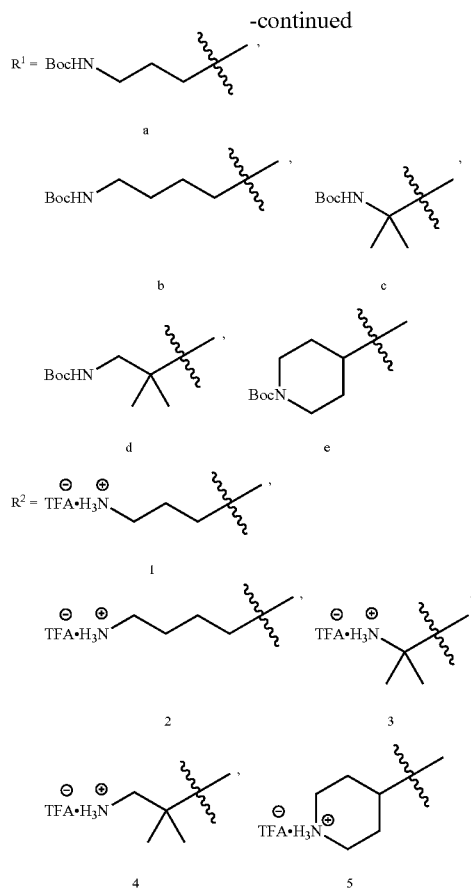

tert-Butyl (S)-3-(2-bromo-4-(methoxycarbonyl) phenoxy) pyrrolidine-1-carboxylate (101). To a solution of methyl 3-bromo-4-hydroxybenzoate (0.626 g, 2.70 mmol) in dry THF (35 mL) under anhydrous conditions was added (R)-tert-butyl 3-hydroxypyrrolidine-1-carboxylate (0.505 g, 2.70 mmol) and triphenyl phosphine (1.43 g, 5.39 mmol). The reaction mixture was then cooled in an ice bath, and DIAD (1.12 g, 5.56 mmol) dissolved in THF (10 mL) was added dropwise. The reaction mixture was stirred for 1 h at room temperature under argon. Upon completion the reaction was diluted with ethyl acetate (100 mL). The organic layer was washed with water (2×50 mL), brine (50 mL), dried over MgSO$_4$, solids filtered, and the solvent removed under reduced pressure. The residue was then purified by column chromatography (silica gel, hexanes:EtOAc=5:1) to yield 101 (0.837 g, 77% yield) as white solid. $^1$H NMR (500 MHz, CDCl$_3$): δ ppm 8.22 (s, 1H), 7.93 (d, J=8.0 Hz, 1H), 6.85 (d, J=8.0 Hz, 1H), 5.00-4.98 (m, 1H), 3.88 (s, 3H), 3.63-3.56 (m, 4H), 2.23-2.13 (m, 2H), 1.45 (s, 9H). $^{13}$C NMR (125 MHz, CDCl$_3$): δ ppm 165.67, 157.47, 143.72, 135.31, 130.41, 124.36, 113.33, 79.76, 79.74, 78.32, 52.29, 51.57, 51.22, 44.25, 43.84, 31.85, 31.02, 28.60. MS (ESI) m/z=400.6 [M+H]$^+$.

(S)-3-Bromo-4-((1-(tert-butoxycarbonyl) pyrrolidin-3-yl) oxy) benzoic acid (102). To a solution of 101 (1.08 g, 2.70 mmol) in MeOH (10 mL) was added 3 M NaOH (10 mL), and the reaction was allowed to stir at room temperature for 6 h. MeOH was then removed under reduced pressure. The remaining aqueous solution was acidified with 12 M HCl to pH=2. The product was extracted with CH$_2$Cl$_2$ (50 mL) and the organics washed with water (2×50 mL), brine (50 mL), dried over MgSO$_4$, solids filtered, and solvent removed under reduced pressure to yield 102 (0.94 g, 93% yield) as white solid. $^1$H NMR (300 MHz, CDCl$_3$): δ ppm 8.29 (d, 1H, J=4.7 Hz), 8.01 (t, 1H, J=8.9 Hz), 6.88 (d, 1H, J=8.6 Hz), 5.03-5.01 (m, 1H), 3.70-3.56 (m, 4H), 2.30-2.13 (m, 2H), 1.47 (s, 9H). $^{13}$C NMR (125 MHz, CDCl$_3$): <5 ppm 169.84, 157.90, 154.76, 154.49, 135.77, 130.93, 123.49, 113.12, 112.98, 79.94, 78.18, 51.45, 51.07, 44.15, 43.72, 31.67, 30.87, 28.45.

(S)-4-((1-(tert-Butoxycarbonyl) pyrrolidin-3-yl) oxy)-3-cyclohexylbenzoic acid (103a). To a solution of 7 (0.410 g, 1.87 mmol), in dry DMF (40 mL) under anhydrous conditions was added 1-cyclohexen-1-yl-boronic acid (0.358 g, 2.84 mmol), Pd(PPh$_3$)$_4$ (0.325 g, 0.281 mmol), and Cs$_2$CO$_3$ (1.85 g, 5.68 mmol). The mixture was heated to 100° C. under argon and stirred for 20 h. The solvent was then removed under reduced pressure, and the residue was taken into EtOAc (100 mL). The organic solution was washed with water (2×50 mL) and brine (50 mL), dried over MgSO$_4$, solids filtered, and solvent removed under reduced pressure. The residue was purified by column chromatography (silica gel, hexanes:acetone:AcOH=88:10:2) to yield white solid (0.419 g, 1.30 mmol). A portion of this solid (0.102 g, 0.262 mmol) was dissolved in MeOH (20 mL). The air was evacuated and exchanged with argon three times and 10% Pd on activated carbon (0.017 g) was added. The argon was evacuated and exchanged with the H$_2$ gas three times and the reaction was allowed to stir under H$_2$ for 12 h. The mixture was filtered through celite and the solvent removed under reduced pressure to yield 103a (0.0922 g, 75% overall yield) as off-white solid. $^1$H NMR (500 MHz, CD$_3$OD): δ ppm 7.87-7.84 (m, 2H), 6.96 (d, 1H, J=8.0 Hz), 5.10-5.08 (m, 1H), 3.61-3.45 (m, 4H), 2.85 (t, 1H, J=9.8 Hz), 2.20-2.16 (m, 2H), 1.82-1.73 (m, 6H), 1.45 (s, 4.5H), 1.42, (s, 4.5H), 1.38-1.25 (m, 4H). $^{13}$C NMR (125 MHz, CD$_3$OD): δ ppm 170.58, 159.11, 156.50, 156.39, 137.98, 137.89, 130.21, 129.73, 125.00, 124.90, 113.13, 113.10, 81.08, 81.04, 77.77, 76.94, 52.76, 52.28, 45.52, 45.12, 38.91, 38.85, 34.32, 34.29, 33.82, 33.72, 32.38, 31.69, 28.82, 28.29, 28.23, 28.19, 28.16, 27.43.

(S)-4-((1-(tert-Butoxycarbonyl) pyrrolidin-3-yl) oxy)-3-(4-(trifluoromethyl) cyclohexyl) benzoic acid (103b). The synthesis of compound 103b followed the same procedure as for compound 103a. Column chromatography (silica gel, hexanes:acetone:AcOH=88:10:2) afforded white solid (0.0983 g, 41% yield). $^1$H NMR (300 MHz, CD$_3$OD): δ ppm 7.89-7.86 (m, 2H), 7.01-6.97 (m, 1H), 5.13-5.10 (m, 1H), 3.59-3.42 (m, 4H), 2.98-2.81 (m, 1H), 2.44-2.36 (m, 1H), 2.22-2.18 (m, 2H), 2.05-1.98 (m, 4H), 1.81-1.66 (m, 4H), 1.46 (m, 4.5H), 1.43 (m, 4.5H). $^{13}$C NMR (75 MHz, CD$_3$OD): δ ppm 175.31, 169.94, 159.52, 159.35, 156.49, 156.44, 13662, 136.54, 136.51, 132.16, 130.69, 130.66, 130.12, 129.70, 129.63, 128.44, 124.50, 124.36, 124.30, 113.29, 113.15, 81.17, 81.13, 77.89, 77.82, 77.12, 52.76, 52.32, 45.52, 45.13, 38.37, 38.03, 37.43, 26.66, 25.08, 25.01, 20.88.

Methyl 3-amino-5-fluorobenzoate (104). In a 100 mL round bottom flask, 3-amino-5-fluorobenzoic acid (0.054 g, 0.16 mmol, 1 equiv.) was dissolved in methanol (26 mL) and cooled to 0° C. Thionyl chloride (SOCl$_2$) (0.045 g, 0.24 mmol, 1.5 equiv.) was added dropwise and the reaction was refluxed at 70° C. overnight. The reaction was allowed to cool to room temperature and concentrated under reduced pressure. The reaction was dissolved with ethyl acetate and sat. NaHCO$_3$ and washed with sat. NaHCO$_3$ and brine. The organic layers were dried over Na$_2$SO$_4$, and concentrated under reduced pressure. The light brown crystals were collected and dried. Compound 104 was used without further purification (2.065 g, 95% yield). Data: $^1$H NMR (400 MHz, CDCl$_3$) δ 7.12 (dd, J=2.2, 1.4 Hz, 1H), 7.06 (ddd, J=9.1, 2.4, 1.4 Hz, 1H), 6.53 (dt, J=10.2, 2.3 Hz, 1H), 3.91 (d, J=2.1 Hz, 2H), 3.87 (s, 3H); $^{13}$C NMR (101 MHz, CDCl$_3$) δ 166.4, 163.6 (d, J=244.3 Hz), 148.3 (d, J=10.8 Hz), 132.7 (d, J=9.7 Hz), 111.9, 106.2 (d, J=24.2 Hz), 106.1 (d, J=25.3 Hz), 52.4; LRMS-ESI: Exact mass calcd for C$_8$H$_9$FNO$_2$ [M+H]$^+$: 170.1; found: 170.2.

General procedure A for synthesis of 105a-c, e. In a 100 mL round bottom flask, the carboxylic acid (a-c or e) (1 equiv.) was dissolved in CH$_2$Cl$_2$:DMF (1:1) (10 mL) and cooled to 0° C. 1-Bis(dimethylamino)methylene-1H-1,2,3-triazolo[4,5-b]pyridinium 3-oxid hexafluorophosphate (HATU) (1.5 equiv.) was added to the reaction mixture and stirred for 5 min. Then 104 (1.01 equiv.) was added followed by dropwise addition of N,N-diisopropylethylamine (0.1 mL, 0.89 mmol, 2 equiv.). The reaction was stirred and allowed to warm to room temperature. The reaction was concentrated under reduced pressure, diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford the titled compound.

Methyl 3-(4-((tert-butoxycarbonyl) amino) butanamido)-5-fluorobenzoate (105a). 105a (0.7688 g, 92% yield). $^1$H NMR (400 MHz, CDCl$_3$) δ 9.53 (s, 1H), 7.89 (d, J=2.2 Hz, 1H), 7.87 (d, J=2.3 Hz, 1H), 7.55-7.34 (m, 1H), 4.93 (s, 1H), 3.89 (s, 3H), 3.23 (d, J=7.3 Hz, 2H), 2.46-2.36 (m, 2H), 1.87 (tt, J=8.1, 5.5 Hz, 2H), 1.45 (s, 9H); $^{13}$C NMR (101 MHz, CDCl$_3$) δ 171.7, 165.9, 162.7 (d, J=245.3 Hz), 157.5, 140.2 (d, J=10.9 Hz), 132.1 (d, J=8.9 Hz), 116.1, 111.5 (d, J=4.0 Hz), 111.3, 80.1, 52.4, 39.2, 34.5, 28.3, 27.2; LRMS-ESI: Exact mass calcd for C$_{17}$H$_{23}$FN$_2$NaO$_5$ [M+Na]$^+$: 377.15; found: 377.10.

Methyl 3-(5-((tert-butoxycarbonyl) amino) pentanamido)-5-fluorobenzoate (105b). 105b (0.8605 g, quant.). $^1$H NMR (500 MHz, CDCl$_3$) δ 8.08 (s, 1H), 7.92 (dd, J=10.5, 2.7 Hz, 1H), 7.76 (s, 1H), 7.43 (ddd, J=8.6, 2.6, 1.4 Hz, 1H), 4.71 (s, 1H), 3.90 (s, 3H), 3.20 (q, J=6.6 Hz, 2H), 2.43 (dd, J=8.6, 6.7 Hz, 2H), 1.91-1.70 (m, 2H), 1.56 (p, J=6.8 Hz, 2H), 1.44 (s, 9H); $^{13}$C NMR (126 MHz, CDCl$_3$) δ 172.0, 165.8, 162.7 (d, J=245.3 Hz), 156.6, 151.8, 140.1 (d, J=11.2 Hz), 132.1 (d, J=9.1 Hz), 116.0, 111.6 (d, J=8.8 Hz), 111.4 (d, J=5 Hz), 79.5, 52.4, 39.2, 38.6, 36.7, 29.5, 28.4, 22.5; LRMS-ESI: Exact mass calcd for C$_{18}$H$_{25}$FN$_2$NaO$_5$ [M+Na]$^+$: 391.2; found: 391.2.

Methyl 3-(2-((tert-butoxycarbonyl) amino)-2-methylpropanamido)-5-fluorobenzoate (105c). 105c (0.1967 g, 45% yield). $^1$H NMR (400 MHz, CDCl$_3$) δ 9.30 (s, 1H), 7.84 (d, J=10.7 Hz, 1H), 7.75 (d, J=1.7 Hz, 1H), 7.43 (ddd, J=8.7, 2.5, 1.4 Hz, 1H), 4.94 (s, 1H), 3.91 (s, 3H), 1.57 (d, J=2.8 Hz, 6H), 1.44 (s, 9H); $^{13}$C NMR (101 MHz, CDCl$_3$) δ 173.0, 165.7, 162.8 (d, J=245.3 Hz), 155.5, 140.0 (d, J=11.4 Hz), 132.2 (d, J=10.1 Hz), 116.1, 111.7 (d, J=12.0 Hz), 111.4 (d, J=14.9 Hz), 81.3, 57.8, 52.4, 28.2, 25.6; LRMS-ESI: Exact mass calcd for C$_{17}$H$_{23}$FN$_2$NaO$_5$ [M+Na]$^+$: 377.15; found: 377.10. tert-Butyl 4-((3-fluoro-5-(methoxycarbonyl) phenyl) carbamoyl) piperidine-1-carboxylate (105e). 105e (0.9434 g, quant.). $^1$H NMR (500 MHz, CDCl$_3$) δ 8.13 (s, 1H), 7.88 (dt, J=10.6, 2.3 Hz, 1H), 7.74 (t, J=1.7 Hz, 1H), 7.47-7.39 (m, 1H), 4.16 (s, 2H), 3.89 (s, 3H), 3.11-2.97 (m, 2H), 2.78-2.72 (m, 1H), 2.44 (tt, J=11.5, 3.8 Hz, 1H), 2.23-2.14 (m, 1H), 1.99-1.84 (m, 3H), 1.74 (dtd, J=13.3, 11.8, 4.3 Hz, 2H), 1.46 (d, J=6.4 Hz, 9H); $^{13}$C NMR (126 MHz, CDCl$_3$) δ 173.3, 165.8 (d, J=14.4 Hz), 162.8 (d, J=246.0 Hz), 154.8, 151.94, 139.9 (d, J=10.9 Hz), 132.3 (d, J=9.4 Hz), 129.6, 121.1, 116.2, 111.9 (d, J=23.9 Hz), 111.9 (d, J=27.7 Hz), 80.0, 52.6, 44.3, 38.8, 28.6, 28.6; LRMS-ESI: Exact mass calcd for C$_{19}$H$_{25}$FN$_2$NaO$_5$ [M+Na]$^+$: 403.2; found: 403.2.

Methyl 3-(3-((tert-butoxycarbonyl) amino)-2,2-dimethylpropanamido)-5-fluorobenzoate (105d). In a 20 mL vial, 3-((tert-butoxycarbonyl) amino)-2,2-dimethylpropanoic acid (0.1 g, 0.46 mmol, 1 equiv.) was dissolved in CH$_2$Cl$_2$ (3 mL) and cooled to 0° C. under an argon atmosphere. 1-Chloro-N,N,2-trimethyl-1-propenylamine (Ghosez reagent) (0.14 mL, 1.04 mmol, 2.25 equiv.) was added dropwise to the reaction mixture. The reaction was stirred and allowed to warm to room temperature for 2 h. The reaction was concentrated under reduced pressure. 104 (0.086 g, 0.51 mmol, 1.1 equiv.) was added to the residue and dissolved in THF (5 mL) followed by dropwise addition of N,N-diisopropylethylamine (0.1 mL, 0.63 mmol, 2.1 equiv.). The reaction was heated at 50° C. under an argon atmosphere overnight. The reaction was concentrated under reduced pressure and dissolved in H$_2$O:THF (5:1, 5 mL). The pH was adjusted to pH=8 with sat. NaHCO$_3$ and Boc$_2$O (1 equiv.) was added and stirred for 2 h. The reaction was diluted with ethyl acetate and washed with brine. The organic layers were dried over Na$_2$SO$_4$, and concentrated under reduced pressure. The solid was purified by column chromatography (silica gel, 5-20% acetone in hexanes) to afford the titled compound (0.0639 g, 38% yield). $^1$H NMR (500 MHz, CDCl$_3$) δ 8.76 (s, 1H), 7.87 (m, 1H), 7.81 (dt, J=10.6, 2.3 Hz, 1H), 7.43-7.37 (m, 1H), 5.21 (d, J=7.2 Hz, 1H), 3.87 (s, 3H), 3.36 (d, J=7.0 Hz, 2H), 1.40 (s, 9H), 1.27 (s, 6H); $^{13}$C NMR (126 MHz, CDCl$_3$) δ 175.5, 165.8 (d, J=3.4 Hz), 162.7 (d, J=245.2 Hz), 157.2, 140.1 (d, J=11.2 Hz), 132.1 (d, J=9.0 Hz), 116.8 (d, J=2.7 Hz), 112.1 (d, J=26.8 Hz), 111.8 (d, J=23.8 Hz), 80.4, 52.5, 48.4, 45.1, 28.4, 24.3; LRMS-ESI: Exact mass calcd for C$_{18}$H$_{25}$FN$_2$NaO$_5$ [M+Na]$^+$: 391.2; found: 391.2.

General procedure B for synthesis of 106a-e. In a 100 mL round bottom flask, 105a-e (1 equiv.) was dissolved in a 1:5 MeOH:THF solution and was cooled in an ice bath. A 1M NaOH solution (1.5 equiv.) was added dropwise, and the reaction mixture was allowed to warm to room temperature. Water was added to the reaction mixture and pH=4 was obtained through the addition of 2 M HCl. The aqueous layer was extracted with ethyl acetate, washed with brine, dried over Na$_2$SO$_4$, and concentrated under reduced pressure. The solid was purified by column chromatography (silica gel, 2.5% methanol in dichloromethane) to afford the titled compound.

3-(4-((tert-Butoxycarbonyl) amino) butanamido)-5-fluorobenzoic acid (106a). 106a (0.1846 g, 96% yield). $^1$H NMR (400 MHz, DMSO-d$_6$) δ 13.22 (s, 1H), 10.26 (s, 1H), 7.92 (s, 1H), 7.80 (dt, J=11.2, 2.3 Hz, 1H), 7.29 (ddd, J=9.0, 2.6, 1.4 Hz, 1H), 6.81 (t, J=5.8 Hz, 1H), 2.94 (q, J=6.6 Hz, 2H), 2.30 (t, J=7.4 Hz, 2H), 1.67 (p, J=7.2 Hz, 2H), 1.35 (s, 9H); $^{13}$C NMR (101 MHz, DMSO-d$_6$) δ 172.0, 166.5, 162.3 (d, J=242.1 Hz), 156.0, 141.6 (d, J=10.9 Hz), 133.6 (d, J=8.9 Hz), 116.2, 110.3 (d, J=8.8 Hz), 110.0 (d, J=12.7 Hz), 77.9, 39.9, 34.3, 28.7, 25.7; LRMS-ESI: Exact mass calcd for C$_{16}$H$_{21}$FN$_2$NaO$_5$ [M+Na]$^+$: 363.13; found: 363.05.

3-(5-((tert-Butoxycarbonyl) amino) pentanamido)-5-fluorobenzoic acid (106b). 106b (0.4949 g, 79% yield). $^1$H NMR (500 MHz, DMSO-d$_6$) δ 13.25 (s, 1H), 10.27 (s, 1H), 7.94 (t, J=1.6 Hz, 1H), 7.83 (dt, J=11.2, 2.2 Hz, 1H), 7.31 (ddd, J=9.2, 2.6, 1.4 Hz, 1H), 6.80 (t, J=5.8 Hz, 1H), 2.93 (q, J=6.6 Hz, 2H), 2.55-2.20 (m, 3H), 1.57 (p, J=7.5 Hz, 2H), 1.45-1.38 (m, 2H), 1.37 (s, 9H); $^{13}$C NMR (126 MHz, DMSO-d$_6$) δ 171.8, 166.1 (d, J=3.3 Hz), 161.9 (d, J=242.1 Hz), 155.6, 141.2 (d, J=11.2 Hz), 133.2 (d, J=8.7 Hz), 115.8, 109.9 (d, J=14.2 Hz), 109.7 (d, J=17.6 Hz), 77.4, 39.8, 36.1, 29.1, 28.3, 22.3; LRMS-ESI: Exact mass calcd for $C_{17}H_{23}FN_2NaO_5$ [M+Na]$^+$: 377.1; found: 377.2.

3-(2-((tert-Butoxycarbonyl) amino)-2-methylpropanamido)-5-fluorobenzoic acid (106c). 106c (0.1635 g, 85% yield). $^1$H NMR (400 MHz, DMSO-d$_6$) δ 13.16 (s, 1H), 9.86 (s, 1H), 8.08 (s, 1H), 7.84 (d, J=11.1 Hz, 1H), 7.28 (ddd, J=8.9, 2.6, 1.3 Hz, 1H), 7.01 (s, 1H), 1.35 (s, 9H), 1.32 (s, 6H); $^{13}$C NMR (101 MHz, DMSO-d$_6$) δ 174.4, 166.6, 162.2 (d, J=241.4 Hz), 154.8, 141.9 (d, J=11.4 Hz), 133.3 (d, J=8.5 Hz), 117.1, 110.7 (d, J=25.3 Hz), 110.1 (d, J=23.3 Hz), 78.7, 56.9, 28.5, 25.3; LRMS-ESI: Exact mass calcd for $C_{16}H_{21}FN_2NaO_5$ [M+Na]$^+$: 363.13; found: 363.05.

3-(3-((tert-Butoxycarbonyl) amino)-2,2-dimethylpropanamido)-5-fluorobenzoic acid (106d). 106d (0.127 g, 51% yield). $^1$H NMR (500 MHz, (CD$_3$)$_2$CO) δ 9.25 (s, 1H), 8.07 (t, J=1.7 Hz, 1H), 7.99 (dt, J=11.2, 2.2 Hz, 1H), 7.38 (ddd, J=8.9, 2.6, 1.4 Hz, 1H), 6.21 (s, 1H), 3.38 (d, J=6.7 Hz, 2H), 1.38 (s, 9H), 1.30 (s, 6H); $^{13}$C NMR (126 MHz, (CD$_3$)$_2$CO) δ 176.3, 166.5, 163.3 (d, J=242.2 Hz), 157.5, 142.2 (d, J=11.1 Hz), 133.6 (d, J=10.1 Hz), 117.9, 111.9 (d, J=27.2 Hz), 111.3 (d, J=23.4 Hz), 79.2, 49.1, 45.7, 28.6, 23.8; LRMS-ESI: Exact mass calcd for $C_{17}H_{23}FN_2NaO_5$ [M+Na]$^+$: 377.2; found: 377.2.

3-(1-(tert-Butoxycarbonyl) piperidine-4-carboxamido)-5-fluorobenzoic acid (106e). 106e (0.7095 g, 79% yield). $^1$H NMR (500 MHz, DMSO-d$_6$) δ 12.99 (s, 1H), 10.33 (s, 1H), 7.97 (t, J=1.7 Hz, 1H), 7.83 (dt, J=11.1, 2.2 Hz, 1H), 7.32 (ddd, J=8.9, 2.5, 1.3 Hz, 1H), 3.99 (d, J=12.7 Hz, 2H), 3.83 (d, J=13.2 Hz, 1H), 2.80 (s, 1H), 1.78 (dt, J=13.2, 4.0 Hz, 3H), 1.54-1.47 (m, 2H), 1.39 (m, 9H); $^{13}$C NMR (126 MHz, DMSO-d$_6$) δ 175.7, 173.7, 161.9 (d, J=242.1 Hz), 153.9, 141.1 (d, J=11.3 Hz), 133.2 (d, J=8.8 Hz), 128.9, 109.9 (d, J=22.7 Hz), 109.8 (d, J=27.7 Hz), 78.7, 42.7, 40.1, 38.3, 28.1; LRMS-ESI: Exact mass calcd for $C_{18}H_{23}FN_2NaO_5$ [M+Na]$^+$: 389.2; found: 389.2.

General procedure C for synthesis of 107a-e. In a 100 mL round bottom flask, 106a-e (1 equiv.) was dissolved in CH$_2$Cl$_2$:DMF (1:1) (10 mL) and cooled to 0° C. 1-Bis(dimethylamino)methylene-1H-1,2,3-triazolo[4,5-b]pyridinium 3-oxid hexafluorophosphate (HATU) (1.5 equiv.) was added to the reaction mixture and stirred for 5 min. Then benzyl piperazine-1-carboxylate (1.01 equiv.) was added followed by dropwise addition of N,N-diisopropylethylamine (2 equiv.). The reaction was stirred and allowed to warm to room temperature. The reaction was concentrated under reduced pressure, diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford the titled compound.

Benzyl 4-(3-(4-((tert-butoxycarbonyl) amino) butanamido)-5-fluorobenzoyl) piperazine-1-carboxylate (107a). 107a (0.2653 g, 80% yield). $^1$H NMR (500 MHz, (CD$_3$)$_2$CO) δ 9.57 (s, 1H), 7.69 (dt, J=11.4, 2.2 Hz, 1H), 7.45 (t, J=1.6 Hz, 1H), 7.42-7.25 (m, 5H), 6.88 (ddd, J=8.6, 2.5, 1.3 Hz, 1H), 6.08 (t, J=6.1 Hz, 1H), 5.14 (s, 2H), 3.55 (s, 8H), 3.14 (q, J=6.5 Hz, 2H), 2.41 (t, J=7.2 Hz, 2H), 1.84 (p, J=7.0 Hz, 2H), 1.40 (s, 9H); $^{13}$C NMR (126 MHz, (CD$_3$)$_2$CO) δ 171.4, 168.1, 162.5 (d, J=243.4 Hz), 156.2, 154.7, 141.4 (d, J=11.4 Hz), 138.4 (d, J=8.5 Hz), 137.2, 128.4, 127.9, 127.8, 113.4, 108.3 (d, J=23.4 Hz), 106.9 (d, J=26.7 Hz), 77.8, 66.7, 43.7, 41.7, 39.6, 34.1, 27.8, 25.8; LRMS-ESI: Exact mass calcd for $C_{28}H_{35}FN_4NaO_6$ [M+Na]$^+$: 565.2; found: 565.3.

Benzyl 4-(3-(5-((tert-butoxycarbonyl) amino) pentanamido)-5-fluorobenzoyl) piperazine-1-carboxylate (107b). 107b (0.3120 g, 90% yield). $^1$H NMR (500 MHz, CDCl$_3$) δ 8.78 (s, 1H), 7.48 (d, J=10.4 Hz, 1H), 7.42-7.28 (m, 6H), 6.77 (ddd, J=8.1, 2.4, 1.3 Hz, 1H), 5.14 (s, 2H), 4.80 (t, J=6.3 Hz, 1H), 3.90-3.31 (m, 8H), 3.11 (q, J=6.7 Hz, 2H), 2.33 (t, J=7.5 Hz, 2H), 1.74-1.63 (m, 2H), 1.54-1.46 (m, 2H), 1.41 (s, 9H); $^{13}$C NMR (126 MHz, CDCl$_3$) δ 172.1, 169.2, 165.6, 162.8 (d, J=247.0 Hz), 162.7, 156.6, 155.2, 140.7 (d, J=10.9 Hz), 137.1 (d, J=8.3 Hz), 136.3, 128.7, 128.3, 128.1, 113.9, 109.1 (d, J=23.5 Hz), 108.5 (d, J=26.1 Hz), 79.5, 67.7, 47.5, 42.2, 39.6, 38.7, 36.7, 29.5, 28.5, 22.5; LRMS-ESI: Exact mass calcd for $C_{29}H_{37}FN_4NaO_6$ [M+Na]$^+$: 579.3; found: 579.3.

Benzyl 4-(3-(2-((tert-butoxycarbonyl) amino)-2-methylpropanamido)-5-fluorobenzoyl) piperazine-1-carboxylate (107c). 107c (0.0797 g, quantitative yield). $^1$H NMR (500 MHz, (CD$_3$)$_2$CO) δ 9.43 (s, 1H), 7.72 (d, J=11.4 Hz, 1H), 7.53 (s, 1H), 7.45-7.25 (m, 5H), 6.88 (dt, J=8.5, 1.7 Hz, 1H), 6.35 (s, 1H), 5.14 (s, 2H), 3.61 (d, J=67.6 Hz, 8H), 1.50 (s, 6H), 1.37 (s, 9H); $^{13}$C NMR (126 MHz, (CD$_3$)$_2$CO) δ 173.8, 168.1, 162.4 (d, J=243.3 Hz), 154.7, 141.5 (d, J=11.2 Hz), 138.2 (d, J=8.4 Hz), 137.2, 128.4, 127.8, 127.8, 114.0, 108.3 (d, J=23.8 Hz), 107.3 (d, J=26.6 Hz), 78.8, 66.7, 66.6, 66.6, 57.1, 47.0, 43.7, 41.7, 27.6, 24.6; LRMS-ESI: Exact mass calcd for $C_{28}H_{35}FN_4NaO_6$ [M+Na]$^+$: 565.2; found: 565.3.

Benzyl 4-(3-(3-((tert-butoxycarbonyl) amino)-2,2-dimethylpropanamido)-5-fluorobenzoyl) piperazine-1-carboxylate (107d). 107d (0.120 g, 60% yield). $^1$H NMR (500 MHz, CDCl$_3$) δ 8.71 (s, 1H), 7.44 (dd, J=10.5, 2.4 Hz, 1H), 7.40 (s, 1H), 7.28 (s, 6H), 6.81-6.67 (m, 1H), 5.08 (s, 2H), 3.74-3.32 (m, 8H), 3.28 (d, J=6.7 Hz, 2H), 1.34 (d, J=2.0 Hz, 9H), 1.23-1.14 (m, 6H); $^{13}$C NMR (126 MHz, CDCl$_3$) δ 175.3, 168.9, 162.6 (d, J=246.8 Hz), 157.1, 155.1, 140.4 (d, J=11.3 Hz), 137.1 (d, J=8.8 Hz), 136.3, 128.6, 128.2, 128.0, 114.3, 109.4 (d, J=22.7 Hz), 108.8 (d, J=26.3 Hz), 80.3, 67.6, 48.2, 47.4, 45.0, 43.8, 42.1, 28.4, 24.2; LRMS-ESI: Exact mass calcd for $C_{29}H_{37}FN_4NaO_6$ [M+Na]$^+$: 579.3; found: 579.3.

Benzyl 4-(3-(1-(tert-butoxycarbonyl) piperidine-4-carboxamido)-5-fluorobenzoyl) piperazine-1-carboxylate (107e). 107e (0.5625 g, 91% yield). $^1$H NMR (500 MHz, CDCl$_3$) δ 8.72 (s, 1H), 7.50 (d, J=10.6 Hz, 1H), 7.42-7.30 (m, 6H), 6.80 (ddd, J=8.0, 2.4, 1.3 Hz, 1H), 5.16 (s, 2H), 4.16 (s, 2H), 3.89-3.28 (m, 10H), 2.42 (tt, J=11.5, 3.8 Hz, 1H), 1.88-1.79 (m, 2H), 1.72 (dtd, J=13.3, 11.8, 4.3 Hz, 2H), 1.47 (s, 9H); $^{13}$C NMR (126 MHz, CDCl$_3$) δ 173.6, 169.1, 165.9, 162.7 (d, J=247.0 Hz), 162.7, 155.2, 154.8, 140.6 (d, J=10.8 Hz), 137.2 (d, J=8.4 Hz), 136.3, 128.7, 128.4, 128.2, 114.1, 109.3 (d, J=23.0 Hz), 108.7 (d, J=26.0 Hz), 79.9, 67.7, 47.5, 44.1, 43.6, 42.2, 38.7, 36.6, 28.5; LRMS-ESI: Exact mass calcd for $C_{30}H_{37}FN_4NaO_6$ [M+Na]$^+$: 591.3; found: 591.3.

General procedure D for synthesis of 108a-e. In a 100 mL round bottom flask, compounds 107a-e (1.01 equiv) was dissolved in MeOH (20 mL) and stirred. Then 10% wt. Palladium on activated carbon was added portionwise to the reaction mixture. The atmosphere was exchanged with H$_2$ gas three times, and the reaction was allowed to stir under H$_2$. The reaction mixture was filtered through celite, and the solvent removed under reduced pressure to yield the piperazine, which was used without further purification. In a 100 mL round bottom flask, compound 103a (1 equiv.) was dissolved in CH$_2$Cl$_2$:DMF (1:1) (10 mL) and cooled to 0° C. 1-Bis(dimethylamino)methylene-1H-1,2,3-triazolo[4,5-b]pyridinium3-oxid hexafluorophosphate (HATU) (1.5 equiv.) was added to the reaction mixture and stirred for 5 min. Then the deprotected piperazine residue dissolved in DMF (1.01 equiv.) was added followed by dropwise addition of N A-diisopropylethylamine (2 equiv.). The reaction was stirred and allowed to warm to room temperature. The reaction was concentrated under reduced pressure then diluted with ethyl acetate, extracted from 2 M HCl, and washed with brine. The organic layers were dried over $Na_2SO_4$, and concentrated under reduced pressure. The solid was purified by column chromatography (silica gel, 5-40% acetone in hexanes) to afford the titled compound.

tert-Butyl (S)-3-(4-(4-(3-(4-((tert-butoxycarbonyl) amino) butanamido)-5-fluorobenzoyl) piperazine-1-carbonyl)-2-cyclohexylphenoxy) pyrrolidine-1-carboxylate (108a). 108a (0.1448 g, 77% yield over two steps). $^1$H NMR (500 MHz, $(CD_3)_2CO$) δ 9.59 (s, 1H), 7.66 (dt, J=11.3, 2.2 Hz, 1H), 7.49 (s, 1H), 7.36-7.24 (m, 2H), 7.02 (d, J=8.2 Hz, 1H), 6.89 (ddd, J=8.5, 2.5, 1.2 Hz, 1H), 6.13 (t, J=6.3 Hz, 1H), 5.22-5.07 (m, 1H), 3.65-3.41 (m, 12H), 3.12 (dq, J=12.6, 6.5 Hz, 2H), 2.92-2.84 (m, 1H), 2.40 (t, J=7.2 Hz, 2H), 2.28-2.13 (m, 2H), 1.79 (ddd, J=34.1, 17.2, 10.5 Hz, 7H), 1.48-1.35 (m, 23H); $^{13}$C NMR (126 MHz, $(CD_3)_2CO$) δ 171.6, 170.3, 168.3 (d, J=2.7 Hz), 162.5 (d, J=243.5 Hz), 156.3, 155.5, 154.1, 154.0, 141.3 (d, J=11.3 Hz), 138.2 (d, J=8.5 Hz), 136.7, 128.5, 128.0, 126.4, 120.4, 113.6, 112.4, 112.3, 108.4 (d, J=23.2 Hz), 107.1 (d, J=26.7 Hz), 78.5, 77.9, 76.7, 75.6, 51.5, 51.0, 44.2, 43.9, 39.6, 37.5, 37.4, 34.0, 33.0, 32.6, 32.4, 31.4, 30.6, 27.8, 27.0, 26.9, 26.8, 26.1, 25.8; LRMS-ESI: Exact mass calcd for $C_{42}H_{59}FN_5O_8$ $[M+H^+]^+$: 780.4; found: 780.4.

tert-Butyl (S)-3-(4-(4-(3-(5-((tert-butoxycarbonyl) amino) pentanamido)-5-fluorobenzoyl) piperazine-1-carbonyl)-2-cyclohexylphenoxy) pyrrolidine-1-carboxylate (108b). 108b (0.2565 g, 77% yield over two steps). $^1$H NMR (500 MHz, $(CD_3)_2CO$) δ 9.47 (s, 1H), 7.66 (dt, J=11.3, 2.2 Hz, 1H), 7.50 (d, J=1.6 Hz, 1H), 7.36-7.27 (m, 2H), 7.03 (d, J=8.3 Hz, 1H), 6.88 (ddd, J=8.5, 2.5, 1.3 Hz, 1H), 6.01 (t, J=6.1 Hz, 1H), 5.28-5.05 (m, 1H), 3.98-3.36 (m, 12H), 3.08 (d, J=12.3 Hz, 4H), 2.95-2.79 (m, 1H), 2.38 (t, J=7.4 Hz, 2H), 2.27-2.14 (m, 2H), 1.89-1.63 (m, 7H), 1.52 (q, J=7.2 Hz, 1H), 1.45-1.35 (m, 21H); $^{13}$C NMR (126 MHz, $(CD_3)_2CO$) δ 172.6, 171.0, 169.1, 163.3 (d, J=243.5 Hz), 156.8, 156.3, 154.9, 154.8, 142.2 (d, J=11.4 Hz), 139.1 (d, J=8.5 Hz), 137.5, 128.8, 127.3, 114.3, 113.2 (d, J=10.5 Hz), 109.2 (d, J=23.3 Hz), 107.8 (d, J=26.5 Hz), 79.3, 78.4, 77.6, 76.5, 52.3, 51.8, 45.0, 44.7, 40.6, 38.3, 38.2, 37.2, 33.8, 33.4, 33.2, 32.2, 31.4, 30.3, 28.6, 27.7, 26.9, 23.2; LRMS-ESI: Exact mass calcd for $C_{43}H_{60}FN_5O_8$ $[M+Na]^+$: 816.4; found: 816.4.

tert-Butyl (S)-3-(4-(4-(3-(2-((tert-butoxycarbonyl) amino)-2-methylpropanamido)-5-fluorobenzoyl) piperazine-1-carbonyl)-2-cyclohexylphenoxy) pyrrolidine-1-carboxylate (108c). 108c (0.1382 g, 73% yield over two steps). $^1$H NMR (500 MHz, $(CD_3)_2CO$) δ 9.44 (s, 1H), 7.69 (s, 1H), 7.57 (s, 1H), 7.36-7.22 (m, 2H), 7.03 (d, J=8.3 Hz, 1H), 6.89 (ddd, J=8.5, 2.5, 1.3 Hz, 1H), 6.35 (s, 1H), 5.13 (s, 1H), 3.63-3.40 (m, 7H), 3.14-2.78 (m, 5H), 2.27-2.15 (m, 2H), 1.80-1.71 (m, 5H), 1.49 (s, 6H), 1.46-1.29 (m, 24H); $^{13}$C NMR (126 MHz, $(CD_3)_2CO$) δ 173.8, 170.0, 168.2, 162.5 (d, J=243.5 Hz), 155.4, 154.0, 153.9, 141.4 (d, J=11.3 Hz), 138.2 (d, J=8.8 Hz), 136.6 (d, J=11.3 Hz), 128.2, 126.4, 114.0, 112.3 (d, J=12.1 Hz), 108.4 (d, J=23.5 Hz), 107.3 (d, J=25.0 Hz), 78.8, 78.4, 76.7, 75.7, 57.1, 54.6, 51.4, 51.0, 44.2, 43.9, 37.5, 37.4, 32.9, 32.6, 32.4, 31.4, 30.6, 27.8, 27.6, 26.9, 26.1, 24.6; LRMS-ESI: Exact mass calcd for $C_{42}H_{58}FN_5O_8$ $[M+Na]^+$: 802.4; found: 802.4.

tert-Butyl (S)-3-(4-(4-(3-(3-((tert-butoxycarbonyl) amino)-2,2-dimethylpropanamido)-5-fluorobenzoyl) pipera-zine-1-carbonyl)-2-cyclohexylphenoxy) pyrrolidine-1-carboxylate (108d). 108d (0.040 g, 47% yield over two steps). $^1$H NMR (500 MHz, $(CD_3)_2CO$) δ 9.19 (s, 1H), 7.71 (dd, J=11.0, 2.4 Hz, 1H), 7.55 (s, 1H), 7.38-7.27 (m, 2H), 7.03 (d, J=8.3 Hz, 1H), 6.89 (ddd, J=8.5, 2.6, 1.3 Hz, 1H), 6.21 (d, J=8.8 Hz, 1H), 5.19-5.09 (m, 1H), 3.86-3.41 (m, 10H), 3.36 (d, J=6.7 Hz, 2H), 2.98-2.86 (m, 1H), 2.29-2.13 (m, 3H), 1.89-1.67 (m, 7H), 1.51-1.40 (m, 12H), 1.37 (d, J=3.2 Hz, 9H), 1.33-1.24 (m, 9H); $^{13}$C NMR (126 MHz, $(CD_3)_2CO$) δ 176.2, 170.8, 169.0, 163.2 (d, J=243.1 Hz), 157.5, 156.3, 154.9, 154.7, 142.2 (d, J=11.2 Hz), 139.0 (d, J=8.4 Hz), 137.5, 129.1, 127.3 (d, J=4.7 Hz), 115.4, 113.2 (d, J=12.7 Hz), 109.4 (d, J=23.2 Hz), 108.7 (d, J=26.6 Hz), 79.2, 77.6, 76.6, 52.3, 51.9, 49.1, 48.2, 45.7, 45.1, 44.8, 38.4, 38.3, 33.8, 33.5, 33.3, 32.3, 31.5, 28.7, 28.6, 27.8, 27.0, 23.8; LRMS-ESI: Exact mass calcd for $C_{43}H_{60}FN_5NaO_8$ $[M+Na]^+$: 816.4; found: 816.4.

tert-Butyl (S)-4-((3-(4-(4-((1-(tert-butoxycarbonyl) pyrrolidin-3-yl) oxy)-3-cyclohexylbenzoyl) piperazine-1-carbonyl)-5-fluorophenyl) carbamoyl) piperidine-1-carboxylate (108e). 108e (0.1601 g, 66% yield over two steps). $^1$H NMR (500 MHz, $CDCl_3$) δ 9.00 (s, 1H), 7.46 (d, J=15.0 Hz, 1H), 7.33 (d, J=17.7 Hz, 1H), 7.25-7.12 (m, 2H), 6.77 (t, J=9.1 Hz, 2H), 4.90 (d, J=17.5 Hz, 1H), 4.09 (s, 2H), 3.86-3.20 (m, 12H), 2.69 (d, J=52.8 Hz, 2H), 2.32 (td, J=11.5, 3.9 Hz, 1H), 2.27-1.98 (m, 7H), 1.85-1.52 (m, 9H), 1.43 (s, 9H), 1.42 (s, 9H); $^{13}$C NMR (126 MHz, $CDCl_3$) δ 173.7, 170.8, 169.1, 162.7 (d, J=247.2 Hz), 155.8, 154.7, 140.7, 137.0 (d, J=8.1 Hz), 135.5, 129.2, 127.5, 127.3, 127.2, 114.1, 109.2 (d, J=23.1 Hz), 108.6 (d, J=26.1 Hz), 79.8, 79.6, 76.1, 51.7, 51.2, 47.8, 44.3, 43.9, 43.1, 38.5, 34.7, 31.6, 28.5, 28.5, 25.7, 23.0, 22.7, 22.1; LRMS-ESI: Exact mass calcd for $C_{44}H_{60}FN_5NaO_8$ $[M+Na]^+$: 828.4; found: 828.4.

General procedure E for synthesis of 1-5. In a 20 mL vial, compound 108a-e (1 equiv.) was dissolved in $CH_2Cl_2$ (4 mL) and cooled to 0° C. Then, TFA (2 mL) was added dropwise to the reaction mixture. The reaction was stopped when TLC confirmed completion of the reaction and the solvent was concentrated under reduced pressure. The product was dissolved in DI water (10 mL) and the aqueous layer was washed with ethyl acetate (3×10 mL). The resulting aqueous solution was frozen and lyophilized to yield the titled compound.

(S)-4-Amino-N-(3-(4-(3-cyclohexyl-4-(pyrrolidin-3-yloxy) benzoyl) piperazine-1-carbonyl)-5-fluorophenyl) butanamide ditrifluoroacetate (1). 1 (0.0879 g, 88% yield). HPLC purity 95%; $^1$H NMR (500 MHz, $D_2O$) δ 7.45 (s, 1H), 7.36-7.26 (m, 2H), 7.19 (s, 1H), 6.99 (s, 1H), 6.85 (s, 1H), 5.20 (s, 1H), 3.90-3.21 (m, 14H), 3.05 (s, 2H), 2.84 (s, 1H), 2.52 (s, 2H), 2.29 (s, 2H), 1.99 (s, 2H), 1.66 (s, 6H), 1.48-0.95 (m, 6H); $^{13}$C NMR (126 MHz, $D_2O$) δ 173.2, 172.9, 172.3, 170.2, 162.7 (q, J=35.2 Hz), 162.3 (d, J=245.7 Hz), 155.0, 139.7, 137.2, 136.3 (d, J=8.8 Hz), 126.9, 126.4, 116.4 (q, J=292.3 Hz), 114.6, 112.5, 109.5, 75.7, 50.5, 44.3, 38.8, 36.5, 33.1, 32.8, 32.7, 30.6, 29.6, 26.4, 25.8, 22.5; HRMS-ESI: Exact mass calcd for $C_{32}H_{42}FN_5NaO_4$ $[M+Na]^+$: 602.3119; found: 602.3115.

(S)-5-Amino-N-(3-(4-(3-cyclohexyl-4-(pyrrolidin-3-yloxy) benzoyl) piperazine-1-carbonyl)-5-fluorophenyl) pentanamide ditrifluoroacetate (2). 2 (0.0752 g, 87% yield). HPLC purity 99%; $^1$H NMR (500 MHz, $D_2O$) δ 7.55-7.37 (m, 1H), 7.37-7.22 (m, 2H), 7.14 (s, 1H), 7.04-6.89 (m, 1H), 6.77 (s, 1H), 5.16 (s, 1H), 4.04-3.13 (m, 13H), 2.99 (t, J=6.9 Hz, 2H), 2.89-2.69 (m, 1H), 2.56-1.99 (m, 5H), 1.64 (d, J=38.2 Hz, 10H), 1.39-0.85 (m, 6H); $^{13}$C NMR (126 MHz, $D_2O$) δ 174.3, 172.0, 169.9, 162.6 (q, J=35.3 Hz), 162.2 (d, J=247.0 Hz), 155.1, 140.0 (d, J=12.6 Hz), 136.9, 136.3 (d, J=8.8 Hz), 126.9, 126.5, 125.8, 116.4 (q, J=292.3 Hz), 114.4, 112.5, 109.17, 75.6, 50.5, 47.3, 44.3, 42.2 39.01, 36.5, 35.8, 32.8, 32.1, 30.6, 26.4, 26.3, 25.9, 21.9; HRMS-ESI: Exact mass calcd for $C_{33}H_{44}FN_5NaO_4$ [M+Na]$^+$: 616.3275; found: 616.3275.

(S)-2-Amino-N-(3-(4-(3-cyclohexyl-4-(pyrrolidin-3-yloxy) benzoyl) piperazine-1-carbonyl)-5-fluorophenyl)-2-methylpropanamide ditrifluoroacetate (3). 3 (0.096 g, 93% yield). HPLC purity 97%; $^1$H NMR (500 MHz, D$_2$O) δ 7.49 (s, 1H), 7.34 (dd, J=37.1, 15.1 Hz, 3H), 7.05 (s, 2H), 5.26 (d, J=16.7 Hz, 1H), 4.00-3.37 (m, 13H), 2.90 (s, 1H), 2.34 (s, 2H), 1.91-1.56 (m, 12H), 1.50-1.11 (m, 5H); $^{13}$C NMR (126 MHz, D$_2$O) δ 172.6, 171.5, 170.3, 162.8 (q, J=35.4 Hz), 162.3 (d, J=245.7 Hz), 155.0, 138.6 (d, J=10.1 Hz), 137.5, 136.3 (d, J=8.4 Hz), 126.9, 126.2, 116.3 (q, J=292.3 Hz) 116.1, 112.6, 111.3 (d, J=23.9 Hz), 111.0 (d, J=23.9 Hz), 75.8, 57.7, 50.6, 47.6, 46.9, 44.3, 42.5, 41.9, 36.6, 32.8, 32.7, 30.5, 26.4, 25.8, 22.9; HRMS-ESI: Exact mass calcd for $C_{32}H_{42}FN_5NaO_4$ [M+Na]$^+$: 602.3119; found: 602.3113.

(S)-3-Amino-N-(3-(4-(3-cyclohexyl-4-(pyrrolidin-3-yloxy) benzoyl) piperazine-1-carbonyl)-5-fluorophenyl)-2,2-dimethylpropanamide ditrifluoroacetate (4). 4 (0.0226 g, 83% yield). HPLC 99%; $^1$H NMR (500 MHz, D$_2$O) δ 7.63-7.26 (m, 4H), 7.19-6.99 (m, 2H), 5.30 (d, J=15.8 Hz, 1H), 4.02-3.37 (m, 12H), 3.22 (s, 2H), 2.95 (s, 1H), 2.55-2.17 (m, 2H), 1.90-1.63 (m, 5H), 1.50-1.37 (m, 10H); $^{13}$C NMR (126 MHz, D$_2$O) δ 177.0, 172.8, 170.6, 163.0 (q, J=35.4 Hz), 162.3 (d, J=245.7 Hz), 154.9, 138.8 (d, J=10.9 Hz), 137.7, 136.2 (d, J=9.2 Hz), 127.0, 126.4, 126.0, 116.7, 116.3 (q, J=293.6 Hz) 112.6, 111.8 (d, J=26.2 Hz), 111.0 (d, J=21.4 Hz), 75.9, 50.6, 47.6, 47.2, 46.9, 44.3, 42.6, 42.0, 41.1, 36.4, 32.8, 32.7, 30.48, 26.5, 25.8, 22.4; HRMS-ESI: Exact mass calcd for $C_{33}H_{44}FN_5NaO_4$ [M+Na]$^+$: 616.3275; found: 616.3264.

(S)—N-(3-(4-(3-cyclohexyl-4-(pyrrolidin-3-yloxy) benzoyl) piperazine-1-carbonyl)-5-fluorophenyl) piperidine-4-carboxamide ditrifluoroacetate (5). 5 (0.0671 g, 88% yield). HPLC purity 95%; $^1$H NMR (500 MHz, D$_2$O) δ 7.46 (s, 1H), 7.41-7.17 (m, 3H), 7.13-6.89 (m, 2H), 5.32-5.19 (m, 1H), 3.92-3.33 (m, 16H), 3.11 (s, 2H), 2.84 (d, J 10=56.4 Hz, 2H), 2.47-2.25 (m, 2H), 2.13 (s, 2H), 2.03-1.84 (m, 3H), 1.83-1.61 (m, 6H), 1.45-1.06 (m, 6H); $^{13}$C NMR (126 MHz, D$_2$O) δ 174.8, 172.5, 170.4, 162.8 (q, J=35.4 Hz), 162.4 (d, J=250.7 Hz), 155.0, 139.4, 137.5, 136.2 (d, J=9.1 Hz), 126.9, 126.2, 116.3 (d, J=291.8 Hz), 114.9 (d, J=21.4 Hz), 112.6, 110.1 (d, J=21.4 Hz), 75.8, 50.6, 47.6, 47.1, 44.3, 43.0, 42.5, 41.9, 40.4, 36.4, 32.8, 32.7, 30.5, 26.4, 25.8, 24.9; HRMS-ESI: Exact mass calcd for $C_{34}H_{44}FN_5NaO_4$ [M+Na]$^+$: 628.3275; found: 628.3270.

The synthetic route for 6-10 is shown in Scheme 2. For this synthetic route the common reaction procedures for each derivative have been reported as general procedures A-F. The amide of compounds 12a-e was methylated with methyl iodide, general procedure D, to produce 14a-e in good yield. Compounds 14a-e underwent Cbz deprotection through hydrogenation followed by amide bond coupling, general procedure E, with 8 to produce 15a-e, respectively. The Boc deprotection of 15a-e with TFA, general procedure F, produced the final products 6-10.

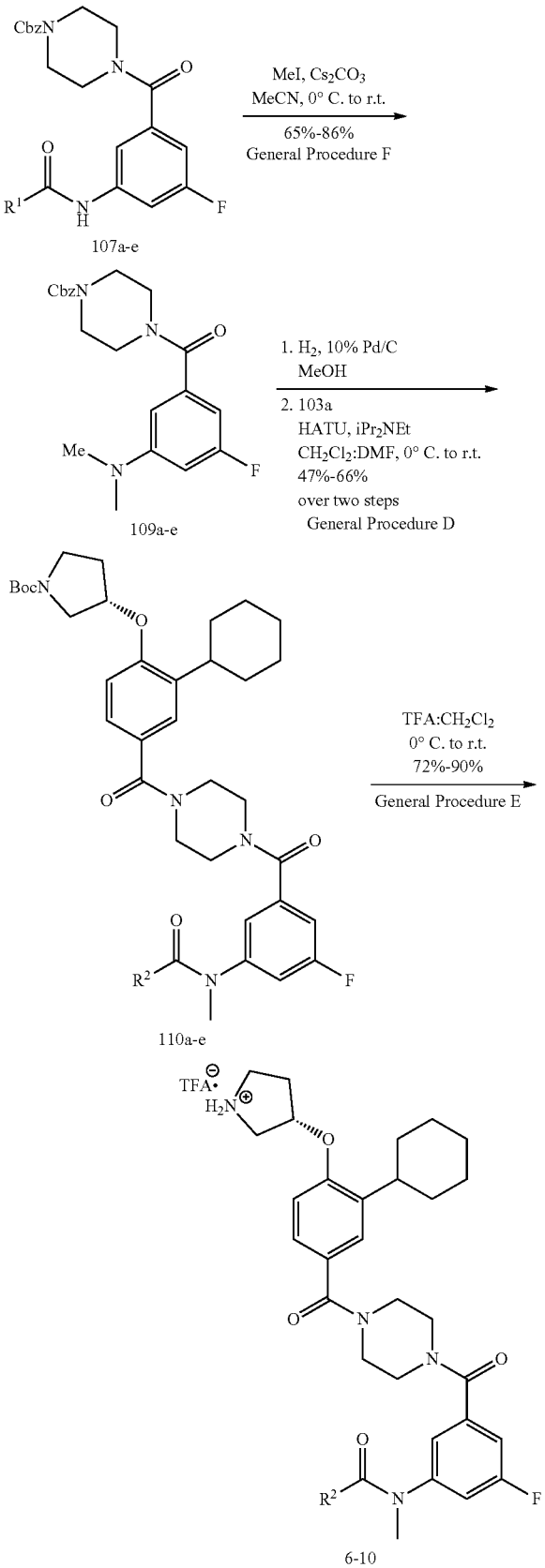

Scheme 2: synthetic route for compounds 6-10.

-continued

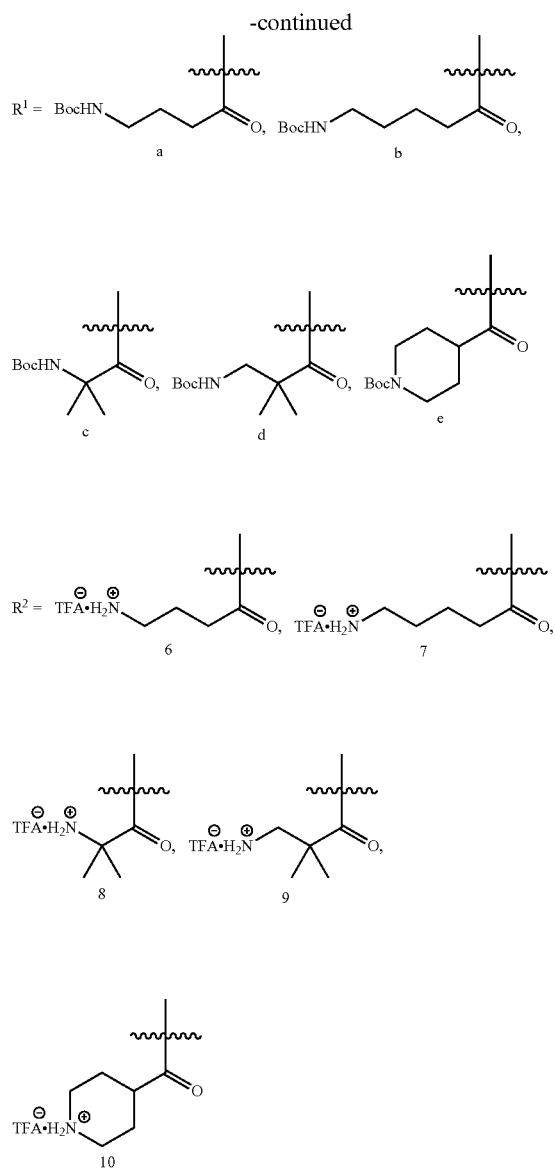

General procedure F for synthesis of 109a-e. In a 20 mL vial, 107a-e (1 equiv.) was dissolved in acetonitrile (5 mL) and cooled to 0° C. Cesium carbonate (3 equiv.) was added to the reaction mixture followed by dropwise addition of methyl iodide (1.5 equiv.). The reaction was stirred and allowed to warm to room temperature. The reaction was diluted with ethyl acetate, extracted from 2 M HCl, and washed with brine. The organic layers were dried over $Na_2SO_4$, and concentrated under reduced pressure. The solid was purified by column chromatography (silica gel, 5-40% acetone in hexanes) to afford the titled compound.

Benzyl 4-(3-(4-((tert-butoxycarbonyl) amino)-N-methylbutanamido)-5-fluorobenzoyl) piperazine-1-carboxylate (109a). 109a (0.1148 g, 75% yield). $^1$H NMR (500 MHz, CDCl$_3$) δ 7.43-7.19 (m, 5H), 7.13-6.88 (m, 3H), 5.11 (s, 2H), 4.79 (t, J=6.2 Hz, 1H), 3.87-3.29 (m, 9H), 3.22 (s, 3H), 3.05 (d, J=10.8 Hz, 2H), 2.14 (m, 3H), 1.84-1.57 (m, 2H), 1.35 (s, 9H); $^{13}$C NMR (126 MHz, CDCl$_3$) δ 172.1, 167.9, 162.7 (d, J=251.3 Hz), 156.0, 155.0, 145.8, 138.4, 136.2, 128.5, 128.2, 128.0, 121.8, 116.1, 113.6, 78.9, 67.5, 47.4, 43.6, 42.1, 39.9, 37.4, 31.6, 28.4, 25.5; LRMS-ESI: Exact mass calcd for $C_{29}H_{37}FN_4NaO_6$ [M+Na]$^+$: 579.3; found: 579.3.

Benzyl 4-(3-(5-((tert-butoxycarbonyl) amino)-N-methylpentanamido)-5-fluorobenzoyl) piperazine-1-carboxylate (109b). 109b (0.220 g, 86% yield). $^1$H NMR (500 MHz, CDCl$_3$) δ 7.37-7.30 (m, 5H), 7.13-7.04 (m, 2H), 7.00 (dd, J=8.8, 2.4 Hz, 1H), 5.14 (s, 2H), 4.71-4.58 (m, 1H), 3.88-3.34 (m, 8H), 3.26 (s, 3H), 3.04 (d, J=7.3 Hz, 2H), 2.28-2.07 (m, 2H), 1.72-1.53 (m, 2H), 1.43-1.40 (m, 11H); $^{13}$C NMR (126 MHz, CDCl$_3$) δ 172.4, 168.1, 162.8 (d, J=251.8 Hz), 156.1, 155.1, 146.1, 138.5, 136.3, 128.67, 128.4, 128.2, 121.9, 116.2, 113.7, 79.1, 67.7, 47.5, 43.9, 42.3, 40.2, 37.5, 33.8, 29.6, 28.5, 22.4; LRMS-ESI: Exact mass calcd for $C_{30}H_{39}FN_4NaO_6$ [M+Na]$^+$: 593.3; found: 593.3.

Benzyl 4-(3-(2-((tert-butoxycarbonyl) amino)-N,2-dimethylpropanamido)-5-fluorobenzoyl) piperazine-1-carboxylate (109c). 109c (0.0613 g, 75% yield). $^1$H NMR (500 MHz, CDCl$_3$) δ 7.58-7.24 (m, 5H), 7.05 (dd, J=20.3, 5.2 Hz, 3H), 5.14 (s, 2H), 4.58 (s, 1H), 3.92-3.37 (m, 8H), 3.31 (s, 3H), 1.47 (s, 6H), 1.43-1.40 (m, 9H); $^{13}$C NMR (126 MHz, CDCl$_3$) δ 173.2, 168.3, 162.5 (d, J=249.5 Hz), 155.0, 154.0, 147.1, 137.5, 136.2, 128.6, 128.2, 128.0, 122.1, 116.2 (d, J=22.8 Hz), 113.2 (d, J=20.2 Hz), 79.9, 67.6, 57.3, 47.4, 43.9, 42.1, 40.4, 28.3, 27.1; LRMS-ESI: Exact mass calcd for $C_{29}H_{37}FN_4NaO_6$ [M+Na]$^+$: 579.3; found: 579.3.

Benzyl 4-(3-(3-((tert-butoxycarbonyl) amino)-N,2,2-trimethylpropanamido)-5-fluorobenzoyl) piperazine-1-carboxylate (109d). 109d (0.046 g, 75% yield). $^1$H NMR (500 MHz, CDCl$_3$) δ 7.33-7.23 (m, 5H), 7.10-6.92 (m, 3H), 5.17 (t, J=6.6 Hz, 1H), 5.08 (s, 2H), 3.81-3.31 (m, 9H), 3.18 (s, 3H), 3.14 (d, J=6.5 Hz, 2H), 1.35 (d, J=2.8 Hz, 9H), 1.19 (s, 6H); $^{13}$C NMR (126 MHz, CDCl$_3$) δ 176.5, 168.1, 163.6 (d, J=252.0 Hz), 156.5, 155.1, 146.7 (d, J=9.5 Hz), 138.2 (d, J=7.6 Hz), 136.3, 128.7, 128.4, 128.2, 123.3, 117.5 (d, J=21.7 Hz), 113.9 (d, J=22.7 Hz), 79.1, 67.7, 51.4, 47.5, 45.5, 43.9, 42.2, 40.9, 28.5, 24.2; LRMS-ESI: Exact mass calcd for $C_{30}H_{39}FN_4NaO_6$ [M+Na]$^+$: 593.3; found: 593.3.

Benzyl 4-(3-(1-(tert-butoxycarbonyl)-N-methylpiperidine-4-carboxamido)-5-fluorobenzoyl) piperazine-1-carboxylate (109e). 109e (0.1985 g, 65% yield). $^1$H NMR (500 MHz, CDCl$_3$) δ 7.34 (m, 5H), 7.10 (d, J=7.6 Hz, 1H), 7.05 (t, J=1.6 Hz, 1H), 7.00 (dt, J=8.9, 2.2 Hz, 1H), 5.14 (s, 2H), 4.31-3.31 (m, 12H), 3.25 (s, 3H), 1.85 (d, J=5.3 Hz, 1H), 1.72 (qd, J=12.6, 12.2, 4.4 Hz, 2H), 1.55 (d, J=8.9 Hz, 2H), 1.42 (s, 9H); $^{13}$C NMR (126 MHz, CDCl$_3$) δ 174.4, 168.0, 162.8 (d, J=252.4 Hz), 155.1, 154.6, 146.0 (d, J=8.8 Hz), 138.7, 136.3, 128.7, 128.4, 128.2, 121.9, 116.1, 113.9, 79.7, 67.7, 47.5, 43.6, 39.6, 38.7, 37.8, 28.5; LRMS-ESI: Exact mass calcd for $C_{31}H_{39}FN_4NaO_6$ [M+Na]$^+$: 605.3; found: 605.3.

General procedure D for synthesis of 110a-e. In a 100 mL round bottom flask, compounds 109a-e (1.01 equiv) was dissolved in MeOH (20 mL) and stirred. Then 10% wt. Palladium on activated carbon was added portionwise to the reaction mixture. The atmosphere was exchanged with $H_2$ gas three times, and the reaction was allowed to stir under $H_2$. The reaction mixture was filtered through celite, and the solvent removed under reduced pressure to yield the piperazine, which was used without further purification. In a 100 mL round bottom flask, 103a (1 equiv.) was dissolved in $CH_2Cl_2$:DMF (1:1) (10 mL) and cooled to 0° C. 1-Bis (dimethylamino)methylene-1H-1,2,3-triazolo[4,5-b]pyridinium3-oxid hexafluorophosphate (HATU) (1.5 equiv.) was added to the reaction mixture and stirred for 5 min. Then the deprotected piperazine residue dissolved in DMF (1.01 equiv.) was added followed by dropwise addition of N,N-diisopropylethylamine (2 equiv.). The reaction was stirred and allowed to warm to room temperature. The reaction was concentrated under reduced pressure then diluted with ethyl acetate, extracted from 2 M HCl, and washed with brine. The organic layers were dried over $Na_2SO_4$, and concentrated under reduced pressure. The solid was purified by column chromatography (silica gel, 5-40% acetone in hexanes) to afford the titled compound.

tert-Butyl (S)-3-(4-(4-(3-(4-((tert-butoxycarbonyl) amino)-N-methylbutanamido)-5-fluorobenzoyl) piperazine-1-carbonyl)-2-cyclohexylphenoxy) pyrrolidine-1-carboxylate (110a). 110a (0.0855 g, 57% yield over two steps). $^1$H NMR (500 MHz, $(CD_3)_2CO$) δ 7.33-7.26 (m, 4H), 7.20 (d, J=8.4 Hz, 1H), 7.02 (d, J=8.3 Hz, 1H), 5.94 (d, J=6.2 Hz, 1H), 5.14 (q, J=3.8, 3.3 Hz, 1H), 3.81-3.39 (m, 11H), 3.25 (s, 3H), 3.01 (q, J=6.5 Hz, 2H), 2.92-2.86 (m, 1H), 2.31-2.14 (m, 4H), 1.90-1.65 (m, 8H), 1.42 (d, J=12.2 Hz, 9H), 1.35 (s, 9H); $^{13}$C NMR (126 MHz, $(CD_3)_2CO$) δ 172.3, 170.8, 168.3, 163.5 (d, J=247.9 Hz), 156.7, 156.3, 154.9, 154.7, 147.0 (d, J=10.0 Hz), 137.4, 129.0, 127.3, 122.9, 116.4, 113.8, 113.1 (d, J=10.8 Hz), 79.2, 78.4, 77.6, 76.5, 52.3, 51.8, 45.0, 44.7, 40.5, 38.3, 38.3, 37.3, 33.8, 33.4, 33.2, 32.1, 28.6, 27.8, 27.7, 26.9, 26.5; LRMS-ESI: Exact mass calcd for $C_{43}H_{60}FN_5NaO_8$ [M+Na]$^+$: 816.4; found: 816.4.

tert-Butyl (S)-3-(4-(4-(3-(5-((tert-butoxycarbonyl) amino)-N-methylpentanamido)-5-fluorobenzoyl) piperazine-1-carbonyl)-2-cyclohexylphenoxy) pyrrolidine-1-carboxylate (110b). 110b (0.0999 g, 47% yield over two steps). $^1$H NMR (500 MHz, CDCl$_3$) δ 7.26-7.14 (m, 2H), 7.07 (d, J=9.5 Hz, 2H), 6.99 (d, J=8.9 Hz, 1H), 6.77 (d, J=8.3 Hz, 1H), 4.92 (td, J=4.3, 2.1 Hz, 1H), 4.68 (d, J=11.5 Hz, 1H), 4.01-3.32 (m, 13H), 3.25 (s, 3H), 3.11-2.89 (m, 2H), 2.82 (s, 1H), 2.27-1.97 (m, 5H), 1.76 (m, 5H), 1.59 (q, J=8.2, 7.8 Hz, 2H), 1.47-1.30 (m, 24H); $^{13}$C NMR (126 MHz, CDCl$_3$) δ 172.4, 171.0, 168.0, 162.7 (d, J=249.9 Hz), 156.0, 155.6, 154.5 (d, J=23.5 Hz), 146.0, 137.4, 127.0, 126.6, 126.2, 121.8, 116.2, 113.5, 111.9, 79.5, 79.0, 76.5, 75.4, 51.5, 51.0, 44.2, 43.9, 40.0, 37.4, 33.6, 33.1, 32.8, 32.6, 31.6, 31.5, 30.9, 29.4, 28.4, 28.4, 26.9, 26.3, 22.2; LRMS-ESI: Exact mass calcd for $C_{44}H_{62}FN_5NaO_8$ [M+Na]$^+$: 830.4; found: 830.5.

tert-Butyl (S)-3-(4-(4-(3-(2-((tert-butoxycarbonyl) amino)-N,2-dimethylpropanamido)-5-fluorobenzoyl) piperazine-1-carbonyl)-2-cyclohexylphenoxy) pyrrolidine-1-carboxylate (110c). 110c (0.0530 g, 61% yield over two steps). $^1$H NMR (500 MHz, $(CD_3)_2CO$) δ 7.25-7.15 (m, 2H), 7.12-7.08 (m, 1H), 7.06-6.98 (m, 2H), 6.91 (d, J=8.3 Hz, 1H), 6.07 (s, 1H), 5.02 (t, J=4.3 Hz, 1H), 3.51-3.27 (m, 7H), 3.21 (s, 3H), 2.86 (s, 3H), 2.82-2.69 (m, 1H), 2.15-1.97 (m, 3H), 1.66 (td, J=29.5, 24.9, 11.1 Hz, 5H), 1.39-1.23 (m, 28H), 1.15 (dt, J=12.5, 5.1 Hz, 2H); $^{13}$C NMR (126 MHz, $(CD_3)_2CO$) δ 174.0, 170.9, 168.6, 163.3 (d, J=245.7 Hz), 156.3, 155.2, 154.9, 154.8, 148.4 (d, J=10.1 Hz), 139.2, 137.5, 133.0, 132.7, 132.6, 129.5, 129.5, 129.0, 127.3, 123.2, 116.5 (d, J=21.6 Hz), 113.5 (d, J=22.7 Hz), 113.2, 79.3, 77.6, 76.5, 57.7, 55.4, 52.3, 51.8, 45.1, 44.7, 40.4, 38.3, 33.8, 33.4, 33.2, 32.2, 32.0, 31.4, 28.6, 28.6, 27.7, 27.1, 26.9; LRMS-ESI: Exact mass calcd for $C_{43}H_{60}FN_5NaO_8$ [M+Na]$^+$: 816.4; found: 816.4.

tert-butyl (S)-3-(4-(4-(3-(3-((tert-butoxycarbonyl) amino)-N,2,2-trimethylpropanamido)-5-fluorobenzoyl) piperazine-1-carbonyl)-2-cyclohexylphenoxy) pyrrolidine-1-carboxylate (110d). 110d (0.042 g, 66% yield over two steps). $^1$H NMR (500 MHz, $(CD_3)_2CO$) δ 7.42-7.34 (m, 2H), 7.34-7.20 (m, 3H), 7.03 (dd, J=8.3, 2.0 Hz, 1H), 5.78 (s, 1H), 5.14 (s, 1H), 3.82-3.41 (m, 10H), 3.22 (s, 3H), 3.16 (d, J=6.5 Hz, 2H), 2.89 (t, J=10.8 Hz, 1H), 2.29-2.14 (m, 3H), 1.92-1.65 (m, 5H), 1.52-1.33 (m, 18H), 1.03 (s, 6H); $^{13}$C NMR (126 MHz, $(CD_3)_2CO$) δ 176.0, 170.8, 168.3, 163.4 (d, J=248.2 Hz), 156.9, 156.3, 154.9, 148.0 (d, J=10.1 Hz), 140.1 (d, J=10.1 Hz), 137.5, 129.2, 127.3, 127.3, 124.5, 118.0 (d, J=22.0 Hz), 114.3 (d, J=22.7 Hz), 113.2, 79.2, 78.7, 77.6, 76.6, 52.3, 51.9, 51.4, 46.1, 45.1, 44.8, 41.1, 38.4, 33.8, 33.5, 33.3, 32.3, 31.5, 28.7, 28.6, 27.8, 27.0, 24.9; LRMS-ESI: Exact mass calcd for $C_{44}H_{62}FN_5NaO_8$ [M+Na]$^+$: 830.4; found: 830.4.

tert-butyl (S)-4-((3-(4-(4-((1-(tert-butoxycarbonyl) pyrrolidin-3-yl) oxy)-3-cyclohexylbenzoyl) piperazine-1-carbonyl)-5-fluorophenyl) (methyl) carbamoyl) piperidine-1-carboxylate (110e). 110e (0.1445 g, 52% yield over two steps). $^1$H NMR (500 MHz, CDCl$_3$) δ 7.26 (s, 1H), 7.25-7.18 (m, 1H), 7.12 (d, J=7.7 Hz, 1H), 7.07 (t, J=1.6 Hz, 1H), 7.01 (dt, J=8.9, 2.2 Hz, 1H), 6.79 (d, J=8.3 Hz, 1H), 4.95 (dt, J=4.2, 2.4 Hz, 1H), 4.07 (s, 2H), 3.77-3.39 (m, 12H), 3.27 (s, 3H), 2.86 (d, J=11.8 Hz, 1H), 2.63-2.06 (m, 2H), 1.94-1.50 (m, 11H), 1.45 (s, 9H), 1.43 (s, 9H), 1.41-1.17 (m, 7H); $^{13}$C NMR (126 MHz, CDCl$_3$) δ 174.5, 171.2, 168.1, 162.9 (d, J=254.5 Hz), 154.7, 146.1, 137.6, 127.1, 126.8, 126.3, 121.9, 116.3, 114.2, 112.0, 79.7, 75.6, 51.7, 51.1, 44.4, 44.0, 42.7, 39.6, 37.9, 37.5, 33.3, 33.3, 33.0, 32.8, 31.9, 31.7, 31.1, 28.6, 28.5, 26.4; LRMS-ESI: Exact mass calcd for $C_{45}H_{62}FN_5NaO_8$ [M+Na]$^+$: 842.4; found: 842.4.

General procedure E for synthesis of 6-10. In a 20 mL vial, compound 110a-e (1 equiv.) was dissolved in CH$_2$Cl$_2$ (4 mL) and cooled to 0° C. Then, TFA (2 mL) was added dropwise to the reaction mixture. The reaction was stopped when TLC confirmed completion of the reaction and the solvent was concentrated under reduced pressure. The product was dissolved in DI water (10 mL) and the aqueous layer was washed with ethyl acetate (3×10 mL). The resulting aqueous solution was frozen and lyophilized to yield the titled compound.

(S)-4-amino-N-(3-(4-(3-cyclohexyl-4-(pyrrolidin-3-yloxy) benzoyl) piperazine-1-carbonyl)-5-fluorophenyl)-N-methylbutanamide ditrifluoroacetate (6). 6 (0.0795 g, 90% yield). HPLC 97% purity; $^1$H NMR (500 MHz, D$_2$O) δ 7.33-7.04 (m, 5H), 7.01 (s, 1H), 5.21 (s, 1H), 3.89-2.93 (m, 17H), 2.73 (m, 3H), 2.20 (s, 4H), 1.98-1.40 (m, 8H), 1.36-0.92 (m, 6H); $^{13}$C NMR (126 MHz, D$_2$O) δ 173.8, 172.3, 169.6, 162.7 (d, J=252.0 Hz), 162.5 (q, J=35.3 Hz), 155.0, 144.9, 137.4, 137.2, 126.9, 126.4, 126.0, 121.6, 116.8 (d, J=21.4 Hz), 116.3 (q, J=292.3 Hz) 114.1 (d, J=20.2 Hz), 112.5, 75.6, 50.5, 47.4, 47.1, 44.3, 42.5, 41.9, 38.8, 37.1, 36.5, 32.8, 32.7, 30.9, 30.6, 26.4, 25.9, 22.5; HRMS-ESI: Exact mass calcd for $C_{33}H_{45}FN_5NaO_4$ [M+Na]$^+$: 594.3456; found: 594.3455.

(S)-5-amino-N-(3-(4-(3-cyclohexyl-4-(pyrrolidin-3-yloxy) benzoyl) piperazine-1-carbonyl)-5-fluorophenyl)-N-methylpentanamide ditrifluoroacetate (7). 7 (0.0908 g, 88% yield). HPLC purity 96%; $^1$H NMR (500 MHz, D$_2$O) δ 7.31-7.25 (m, 5H), 7.05 (s, 1H), 5.27 (s, 1H), 3.84 (s, 2H), 3.77-3.32 (m, 11H), 3.25-3.20 (m, 2H), 2.92 (s, 3H), 2.34 (s, 3H), 1.74 (s, 6H), 1.57 (s, 3H), 1.47-1.24 (m, 4H), 1.18 (s, 1H); $^{13}$C NMR (126 MHz, D$_2$O) δ 175.1, 172.5, 169.8, 162.7 (q, J=35.3 Hz), 162.7 (d, J=252.0 Hz), 155.0, 145.0 (d, J=8.8 Hz), 137.5, 127.0, 126.2, 121.6, 116.7 (d, J=20.2 Hz), 116.3 (q, J=292.3 Hz), 114.2 (d, J=22.7 Hz), 112.5, 75.8, 50.6, 47.6, 47.1, 44.3, 42.5, 41.9, 39.1, 37.1, 36.5, 33.1, 32.8, 32.7, 30.5, 26.5, 26.4, 26.2, 25.8, 21.8; HRMS-ESI: Exact mass calcd for $C_{34}H_{46}FN_5NaO_4$ [M+Na]$^+$: 630.3432; found: 630.3426.

(S)-2-amino-N-(3-(4-(3-cyclohexyl-4-(pyrrolidin-3-yloxy) benzoyl) piperazine-1-carbonyl)-5-fluorophenyl)-N,2-dimethylpropanamide ditrifluoroacetate (8). 8 (0.1092 g, 88% yield). HPLC purity 98%; $^1$H NMR (500 MHz, D$_2$O) δ 7.44-7.35 (m, 5H), 7.07 (d, J=8.8 Hz, 1H), 5.30 (s, 1H), 4.02-3.48 (m, 12H), 3.34 (d, J=19.1 Hz, 4H), 2.94 (d, J=11.8 Hz, 1H), 2.36 (s, 3H), 1.79 (t, J=24.4 Hz, 6H), 1.65-1.04 (m, 12H); $^{13}$C NMR (126 MHz, D$_2$O) δ 172.7, 171.3, 169.7, 162.9 (q, J=35.3 Hz), 162.6 (d, J=250.7 Hz), 155.0, 144.3 (d, J=12.6 Hz), 137.7, 137.4 (d, J=10.1 Hz), 127.0, 126.4, 126.1, 122.6, 117.8 (d, J=21.4 Hz), 116.3 (q, J=292.3 Hz), 114.9 (d, J=22.7 Hz), 112.6, 75.8, 59.2, 50.6, 47.6, 47.1, 44.4, 42.5, 42.0, 40.6, 36.5, 32.8, 32.7, 30.5, 26.5, 25.8, 23.8; HRMS-ESI: Exact mass calcd for C$_{33}$H$_{44}$FN$_5$NaO$_4$ [M+Na]$^+$: 616.3275; found: 616.3275.

(S)-3-amino-N-(3-(4-(3-cyclohexyl-4-(pyrrolidin-3-yloxy) benzoyl) piperazine-1-carbonyl)-5-fluorophenyl)-N,2,2-trimethylpropanamide ditrifluoroacetate (9). 9 (0.019 g, 72% yield). HPLC purity 99%; $^1$H NMR (500 MHz, D$_2$O) δ 7.48-7.37 (m, 5H), 7.11-7.09 (m, 1H), 5.33 (s, 1H), 3.95-3.42 (m, 12H), 3.33 (d, J=17.3 Hz, 3H), 3.13 (s, 2H), 2.97 (s, 1H), 2.39 (s, 2H), 1.83-1.70 (m, 5H), 1.50-1.10 (m, 12H); $^{13}$C NMR (126 MHz, D$_2$O) δ 176.5, 172.8, 169.9, 162.9 (q, J=35.3 Hz), 162.6 (d, J=250.7 Hz), 155.0, 145.3 (d, J=8.8 Hz), 137.7, 137.2 (d, J=8.6 Hz), 127.0, 126.4, 126.1, 122.6, 117.7 (d, J=22.7 Hz), 116.4 (d, J=292.3 Hz), 114.3 (d, J=22.7 Hz), 112.7, 75.9, 50.7, 49.9, 47.7, 47.2, 46.9, 44.4, 42.6, 42.3, 42.0, 40.7, 36.5, 32.8, 32.8, 30.5, 26.5, 25.8, 23.1, 22.4; HRMS-ESI: Exact mass calcd for C$_{34}$H$_{46}$FN$_5$NaO$_4$ [M+Na]$^+$: 630.3432; found: 630.3422.

(S)—N-(3-(4-(3-cyclohexyl-4-(pyrrolidin-3-yloxy) benzoyl) piperazine-1-carbonyl)-5-fluorophenyl)-N-methylpiperidine-4-carboxamide ditrifluoroacetate (10). 10 (0.090 g, 77% yield). HPLC purity 98%; $^1$H NMR (500 MHz, D$_2$O) δ 7.48-7.11 (m, 5H), 7.07 (d, J=8.9 Hz, 1H), 5.30 (s, 1H), 3.96-3.32 (m, 16H), 3.32-3.05 (m, 3H), 2.99-2.51 (m, 4H), 2.48-2.11 (m, 3H), 1.84 (m, 9H), 1.38 (m, 5H); $^{13}$C NMR (126 MHz, D$_2$O) δ 175.3, 172.8, 169.8, 162.8 (q, J=35.6 Hz), 162.8 (d, J=244.4 Hz), 155.0, 144.4 (d, J=10.1 Hz), 137.7, 137.6 (d, J=10.1 Hz), 127.0, 126.4, 126.1, 121.5, 116.8 (d, J=22.7 Hz), 116.3 (q, J=292.3 Hz), 114.5 (d, J=23.9 Hz), 112.6, 75.8, 50.6, 47.7, 47.1, 44.3, 42.7, 37.5, 36.7, 36.4, 32.8, 32.7, 30.5, 26.4, 25.8, 24.8; HRMS-ESI: Exact mass calcd for C$_{35}$H$_{46}$FN$_5$NaO$_4$ [M+Na]$^+$: 642.3432; found: 642.3439.

The synthesis of 11 is shown in Scheme 3. The deprotection of the Cbz protecting group of 107d by catalytic hydrogenation offered the free amine that was then allowed to couple with 103b by the amide coupling reaction to afford 111. The removal of the Boc protecting group by TFA offered final product 11.

Scheme 3: The synthesis of compound 11.

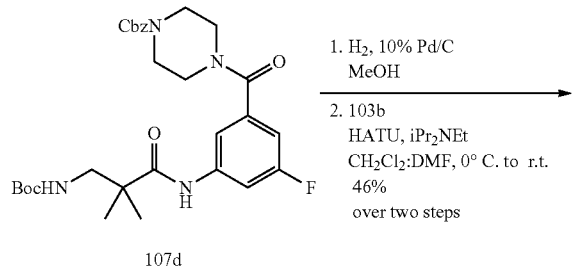

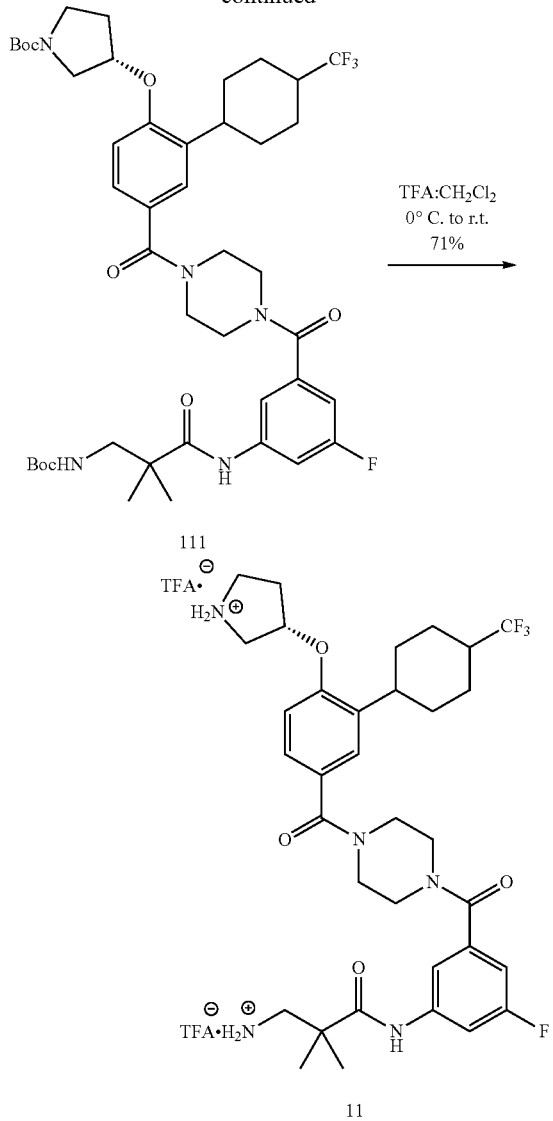

tert-Butyl (S)-3-(4-(4-(3-(3-((tert-butoxycarbonyl) amino)-2,2-dimethylpropanamido)-5-fluorobenzoyl) piperazine-1-carbonyl)-2-(4-(trifluoromethyl) cyclohexyl) phenoxy) pyrrolidine-1-carboxylate (111). In a 100 mL round bottom flask, compounds 107d (0.203 mmol) was dissolved in MeOH (20 mL) and stirred. Then 10% wt. Palladium on activated carbon was added portionwise to the reaction mixture. The atmosphere was exchanged with H$_2$ gas three times, and the reaction was allowed to stir under H$_2$. The reaction mixture was filtered through celite, and the solvent removed under reduced pressure to yield the piperazine, which was used without further purification. In a 100 mL round bottom flask, 103b (1 equiv.) was dissolved in CH$_2$Cl$_2$:DMF (1:1) (10 mL) and cooled to 0° C. 1-[Bis (dimethylamino) methylene-1H-1,2,3-triazolo[4,5-b]pyridinium3-oxid hexafluorophosphate (HATU) (1.5 equiv.) was added to the reaction mixture and stirred for 5 min. Then the deprotected piperazine residue dissolved in DMF (1.01 equiv.) was added followed by dropwise addition of N,N-diisopropylethylamine (2 equiv.). The reaction was stirred and allowed to warm to room temperature. The reaction was concentrated under reduced pressure then diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford 111 (0.138 g, 46% yield over two steps). LRMS-ESI: Exact mass calcd for C$_{42}$H$_{58}$FN$_5$NaO$_8$ [M+Na]$^+$: 884.4; found: 884.4.

(S)-3-amino-N-(3-fluoro-5-(4-(4-(pyrrolidin-3-yloxy)-3-(4-(trifluoromethyl) cyclohexyl) benzoyl) piperazine-1-carbonyl) phenyl)-2,2-dimethylpropanamide ditrifluoroacetate (11). In a 20 mL vial, compound 111 (0.082 mmol) was dissolved in CH$_2$Cl$_2$ (4 mL) and cooled to 0° C. Then, TFA (2 mL) was added dropwise to the reaction mixture. The reaction was stopped when TLC confirmed completion of the reaction and the solvent was concentrated under reduced pressure. The product was dissolved in DI water (10 mL) and the aqueous layer was washed with ethyl acetate (3×10 mL). The resulting aqueous solution was frozen and lyophilized to yield the titled compound 11 (0.06 g, 71% yield). HPLC 99%; HRMS-ESI: Exact mass calcd for C$_{34}$H$_{43}$FN$_5$NaO$_4$ [M+Na]$^+$: 684.3149; found: 684.3111.

The synthetic route for 12-15 is shown in Scheme 4. Thionyl chloride-mediated esterification of 3-amino-5-fluorobenzoic acid produced methyl ester 112. Compound 112 was acylated with acetyl chloride to generate 113, and the methyl ester was hydrolyzed to yield 114. The amide coupling reaction between 103a and 1-Cbz-piperazine or (S)-1-Cbz-3-alkyl-piperazine generated 115a-d, which then underwent deprotection of the Cbz protecting group by catalytic hydrogenation afforded 116a-d. The amide bond coupling reaction of 116a-d with 114 produced 117a-d, which underwent Boc deprotection with trifluoroacetic acid (TFA) to yield final product 12-15, respectively.

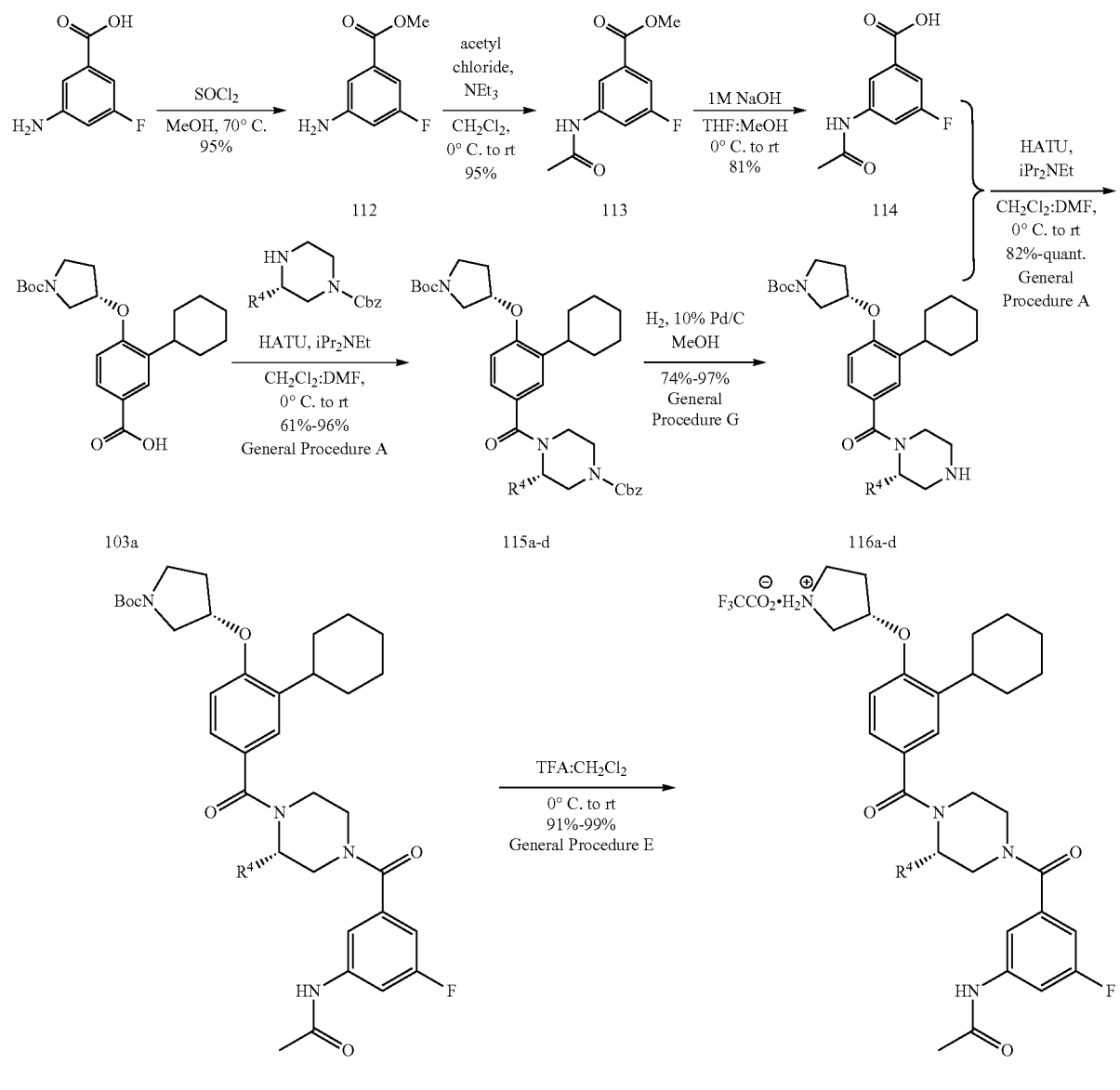

Scheme 4: The synthetic route for compounds 12-15.

a, 12:R⁴ = H
b, 13:⁴ = CH₃
c, 14:R⁴ = CH₂CH₃
d, 15:R⁴ = 

Methyl 3-amino-5-fluorobenzoate (112). In a 100 mL round bottom flask, 3-amino-5-fluorobenzoic acid (0.054 g, 0.16 mmol, 1 equiv.) was dissolved in methanol (26 mL) and cooled to 0° C. Thionyl chloride (SOCl₂) (0.045 g, 0.24 mmol, 1.5 equiv.) was added dropwise and the reaction was refluxed at 70° C. overnight. The reaction was allowed to cool to room temperature and concentrated under reduced pressure. The reaction was dissolved with ethyl acetate and sat. NaHCO₃ and washed with sat. NaHCO₃ and brine. The organic layers were dried over Na₂SO₄, and concentrated under reduced pressure. The light brown crystals were collected and dried. Compound 112 was used without further purification (2.065 g, 95% yield). ¹H NMR (400 MHz, CDCl₃) δ 7.12 (dd, J=2.2, 1.4 Hz, 1H), 7.06 (ddd, J=9.1, 2.4, 1.4 Hz, 1H), 6.53 (dt, J=10.2, 2.3 Hz, 1H), 3.91 (d, J=2.1 Hz, 2H), 3.87 (s, 3H); ¹³C NMR (101 MHz, CDCl₃) δ 166.4, 163.6 (d, J=244.3 Hz), 148.3 (d, J=10.8 Hz), 132.7 (d, J=9.7 Hz), 111.9, 106.2 (d, J=24.2 Hz), 106.1 (d, J=25.3 Hz), 52.4; LRMS-ESI: Exact mass calcd for C₈H₉FNO₂ [M+H⁺]⁺: 170.1; found: 170.2.

Methyl 3-acetamido-5-fluorobenzoate (113). In a 100 mL round bottom flask, 112 (1 g, 5.91 mmol, 1 equiv.) was dissolved in CH₂Cl₂ (30 mL) and cooled to 0° C. Triethylamine (0.9 mL, 6.50 mmol, 1.1 equiv.) was added dropwise to the reaction mixture followed by dropwise addition of acetyl chloride (0.5 mL, 6.50 mmol, 1.1 equiv.). The reaction was stirred and allowed to warm to room temperature. The reaction was diluted with CH₂Cl₂, extracted from 2 M HCl, and washed with brine. The organic layers were dried over Na₂SO₄, and concentrated under reduced pressure. The solid was purified by column chromatography (silica gel, 5-40% acetone in hexanes) to afford the titled compound (1.1803 g, 95% yield). ¹H NMR (500 MHz, DMSO-d₆) δ 10.35 (s, 1H), 7.94 (t, J=1.7 Hz, 1H), 7.82 (dt, J=11.2, 2.2 Hz, 1H), 7.32 (ddd, J=8.9, 2.6, 1.4 Hz, 1H), 3.85 (s, 3H), 2.07 (s, 3H); ¹³C NMR (126 MHz, DMSO-d₆) δ 169.0, 165.0 (d, J=3.6 Hz), 161.9 (d, J=242.5 Hz), 141.3 (d, J=11.2 Hz), 131.8 (d, J=9.2 Hz), 115.4 (d, J=2.5 Hz), 109.9 (d, J=26.6 Hz), 109.7 (d, J=23.5 Hz), 52.5, 24.0; LRMS-ESI: Exact mass calcd for C₁₀H₁₀FNNaO₃ [M+Na]⁺: 234.1; found: 234.1.

3-Acetamido-5-fluorobenzoic acid (114). In a 100 mL round bottom flask, 113 (0.99 g, 4.70 mmol, 1 equiv.) was dissolved in a 1:5 MeOH:THF solution and was cooled in an ice bath. A 1 M NaOH solution (8 equiv.) was added dropwise and the reaction mixture was allowed to warm to room temperature. Water was added to the reaction mixture and pH 4 was obtained through the addition of 2 M HCl. The aqueous layer was extracted with ethyl acetate, washed with brine, dried over Na₂SO₄, and concentrated under reduced pressure. The solid was purified by column chromatography (silica gel, 2.5% methanol in dichloromethane) to afford the titled compound (0.7551 g, 81% yield). ¹H NMR (500 MHz, DMSO-d₆) δ 13.21 (s, 1H), 10.32 (s, 1H), 7.92 (t, J=1.7 Hz, 1H), 7.81 (dt, J=11.1, 2.2 Hz, 1H), 7.31 (ddd, J=9.0, 2.6, 1.4 Hz, 1H), 2.07 (s, 3H); ¹³C NMR (126 MHz, DMSO-d₆) 169.4, 166.5 (d, J=3.6 Hz), 162.3 (d, J=242.2 Hz), 141.6 (d, J=11.1 Hz), 133.6 (d, J=8.8 Hz), 116.1, 109.9 (d, J=23.9 Hz), 109.7 (d, J=27.7 Hz), 24.5; LRMS-ESI: Exact mass calcd for C₉H₈FNNaO₃ [M+Na]⁺: 220.0; found: 220.1.

General procedure A for synthesis of 115a-d. In a 100 mL round bottom flask, the carboxylic acid (103a) (1 equiv.) was dissolved in CH₂Cl₂:DMF (1:1) (10 mL) and cooled to 0° C. 1-Bis(dimethylamino)methylene-1H-1,2,3-triazolo[4,5-b] pyridinium 3-oxid hexafluorophosphate (HATU) (1.5 equiv.) was added to the reaction mixture and stirred for 5 min. Then 1-Cbz-piperazine or (S)-1-Cbz-3-alkyl-piperazine (1.01 equiv.) was added followed by dropwise addition of N,N-diisopropylethylamine (0.1 mL, 0.89 mmol, 2 equiv.). The reaction was stirred and allowed to warm to room temperature. The reaction was concentrated under reduced pressure, diluted with ethyl acetate, extracted from 2 M HCl, and washed with brine. The organic layers were dried over Na₂SO₄, and concentrated under reduced pressure. The solid was purified by column chromatography (silica gel, hexanes:EtOAc=3:1) to afford the titled compound.

Benzyl (S)-4-(6-((1-(tert-butoxycarbonyl) pyrrolidin-3-yl) oxy)-4'-fluoro-[1,1'-biphenyl]-3-carbonyl) piperazine-1-carboxylate (115a). 115a (0.930 g, 93% yield). ¹H NMR (500 MHz, CDCl₃): δ ppm 7.41-7.29 (m, 9H), 7.08-7.04 (m, 2H), 6.94 (d, 1H, J=6.9 Hz), 5.14 (s, 2H), 4.90-4.88 (m, 1H), 3.65-3.20 (m, 12H), 2.09-2.03 (m, 2H), 1.43 (s, 9H). ¹³C NMR (125 MHz, CDCl₃): <5 ppm 173.10, 171.02, 170.10, 162.08 (d, J=245.6 Hz), 155.10, 155.02, 154.99, 154.45, 154.27, 136.19, 133.11, 133.01, 131.11, 130.89, 130.86, 130.22, 128.43, 128.20 (d, J=4.8 Hz), 128.08, 127.89, 114.93 (d, J=20.9 Hz), 114.80 (d, J=20.9 Hz), 113.74, 113.46, 79.53, 79.46, 77.14, 76.26, 67.38, 60.26, 51.34, 50.85, 44.05, 43.64, 31.41, 30.64, 28.36, 20.92, 20.57, 14.08.

Benzyl (S)-4-(4-(((5)-1-(tert-butoxycarbonyl) pyrrolidin-3-yl) oxy)-3-cyclohexylbenzoyl)-3-methylpiperazine-1-carboxylate (115b). 115b (0.2977 g, 96% yield). ¹H NMR (500 MHz, Chloroform-d) δ 7.34-7.19 (m, 5H), 7.12 (d, J=14.8 Hz, 2H), 6.71 (d, J=8.3 Hz, 1H), 5.17-4.99 (m, 2H), 4.90-4.81 (m, 1H), 4.23-3.70 (m, 3H), 3.64-3.35 (m, 3H), 2.87-2.74 (m, 1H), 2.21-1.94 (m, 3H), 1.82-1.54 (m, 4H), 1.38 (d, J=5.5 Hz, 9H), 1.36-1.05 (m, 13H); ¹³C NMR (126 MHz, Chloroform-d) δ 170.94, 155.65, 155.39, 155.28, 154.60, 154.43, 137.39, 137.27, 136.44, 128.52, 128.16, 127.89, 126.00, 125.59, 112.01, 111.92, 79.50, 79.44, 76.50, 75.39, 67.40, 51.51, 51.07, 48.37, 48.08, 44.27, 43.90, 38.58, 37.37, 37.31, 33.07, 32.88, 32.71, 31.68, 31.56, 30.99, 28.47, 26.99, 26.29, 22.63, 21.97, 15.51; LRMS-ESI: Exact mass calcd for C₃₅H₄₇FN₃NaO₆ [M+Na]⁺: 628.3; found: 628.4.

Benzyl (S)-4-(4-(((S)-1-(tert-butoxycarbonyl) pyrrolidin-3-yl) oxy)-3-cyclohexylbenzoyl)-3-ethylpiperazine-1-carboxylate (115c). 115c (0.2600 g, 82%). ¹H NMR (500 MHz, Chloroform-d) δ 7.40-7.23 (m, 5H), 7.16 (d, J=26.5 Hz, 2H), 6.77 (t, J=1.1 Hz, 1H), 5.23-5.04 (m, 2H), 4.98-4.85 (m, 1H), 4.08 (d, J=29.6 Hz, 2H), 3.77-3.41 (m, 4H), 3.15-2.89 (m, 1H), 2.89-2.79 (m, 1H), 2.41-2.03 (m, 3H), 1.92-1.52

(m, 6H), 1.44 (d, J=6.2 Hz, 9H), 1.40-1.11 (m, 4H), 1.06-0.66 (m, 3H); $^{13}$C NMR (126 MHz, Chloroform-d) δ 171.24, 155.56, 155.29, 155.20, 154.59, 154.42, 137.34, 137.27, 136.41, 128.50, 128.12, 127.93, 126.05, 125.75, 125.58, 112.08, 111.85, 79.48, 79.42, 76.49, 75.36, 67.39, 51.49, 51.05, 46.16, 44.26, 43.90, 38.57, 37.36, 37.28, 33.12, 32.80, 32.62, 31.67, 30.97, 28.46, 27.01, 26.95, 26.28, 21.97, 10.43; LRMS-ESI: Exact mass calcd for $C_{36}H_{50}N_3NaO_6$ [M+Na]$^+$: 642.4; found: 642.4.

Benzyl (S)-4-(4-(((S)-1-(tert-butoxycarbonyl)pyrrolidin-3-yl)oxy)-3-cyclohexylbenzoyl)-3-isopropylpiperazine-1-carboxylate (115d). 115d (0.1980 g, 61% yield). $^1$H NMR (500 MHz, Chloroform-d) δ 7.32-7.21 (m, 5H), 7.18-7.01 (m, 2H), 6.70 (t, J=8.4 Hz, 1H), 5.14-4.98 (m, 2H), 4.86 (d, J=4.4 Hz, 1H), 4.51-3.77 (m, 3H), 3.65-3.31 (m, 4H), 3.27-2.62 (m, 4H), 2.21-1.91 (m, 2H), 1.80-1.60 (m, 5H), 1.38 (d, J=7.0 Hz, 9H), 1.33-1.07 (m, 6H), 0.97-0.61 (m, 6H); $^{13}$C NMR (126 MHz, Chloroform-d) δ 172.03, 170.87, 155.43, 155.19, 154.60, 154.43, 137.38, 136.36, 128.51, 128.10, 128.09, 126.37, 126.10, 125.81, 125.49, 112.05, 111.79, 79.49, 79.45, 76.49, 75.40, 67.45, 54.86, 51.48, 51.09, 44.82, 44.27, 43.91, 43.35, 37.36, 33.08, 32.80, 32.66, 31.69, 31.01, 28.48, 27.02, 26.97, 26.28, 25.54, 20.00, 18.79; LRMS-ESI: Exact mass calcd for $C_{37}H_{52}N_3O_6$ [M+H$^+$]$^+$: 634.4; found: 634.4.

General procedure G for synthesis of 116a-d. To a solution of 115a-d (0.15 mmol) in MeOH (20 mL) under argon was added 10% Pd on activated carbon (0.012 g). The argon was evacuated and exchanged with H$_2$ gas three times and the reaction was allowed to stir under H$_2$ for 3 h. The reaction mixture was filtered through celite, and the solvent removed under reduced pressure to yield the titled product.

tert-Butyl (S)-3-(2-cyclohexyl-4-(piperazine-1-carbonyl) phenoxy) pyrrolidine-1-carboxylate (116a). 116a (0.699 g, 97% yield) as off-white solid. $^1$H NMR (300 MHz, CDCl$_3$): δ ppm 7.38-7.30 (m, 4H), 7.01 (t, 2H, J=8.4 Hz), 6.90 (d, 1H, J=8.1 Hz), 4.86-4.83 (m, 1H), 3.61-3.17 (m, 8H), 2.85-2.79 (m, 4H), 2.02-1.98 (m, 2H), 1.37 (s, 9H). $^{13}$C NMR (125 MHz, CDCl$_3$): δ ppm 169.77, 161.78 (d, J=247.3 Hz), 154.64, 154.54, 154.32, 154.17, 132.98 (d, J=9.3 Hz), 130.80, 130.70, 130.65, 129.90, 129.86, 128.46, 127.59, 114.64 (d, J=21.7 Hz), 114.53 (d, J=21.3 Hz), 113.61, 113.33, 79.37, 79.30, 76.89, 76.09, 51.16, 50.66, 49.69, 45.72, 43.81, 43.42, 31.12, 30.39, 28.11.

tert-Butyl (S)-3-(2-cyclohexyl-4-((S)-2-methylpiperazine-1-carbonyl) phenoxy) pyrrolidine-1-carboxylate (116b). 116b (0.1672 g, 76% yield) as off-white solid. $^1$H NMR (500 MHz, Chloroform-d) δ 7.25-7.05 (m, 2H), 6.74 (d, J=8.3 Hz, 1H), 4.89 (tt, J=4.1, 1.8 Hz, 1H), 4.32 (s, 1H), 3.68-3.36 (m, 3H), 3.22-3.04 (m, 1H), 2.98-2.62 (m, 5H), 2.36-1.99 (m, 4H), 1.83-1.62 (m, 5H), 1.41 (d, J=4.8 Hz, 9H), 1.36-1.14 (m, 7H); $^{13}$C NMR (126 MHz, Chloroform-d) δ 170.83, 155.08, 154.97, 154.59, 154.44, 137.25, 137.13, 128.74, 125.90, 125.41, 111.98, 111.88, 79.47, 79.41, 76.46, 75.35, 51.50, 51.07, 50.41, 46.29, 44.26, 43.89, 37.36, 37.30, 33.06, 32.87, 32.71, 31.68, 30.99, 28.46, 27.00, 26.29, 15.50; LRMS-ESI: Exact mass calcd for $C_{27}H_{42}N_3O_4$ [M+H$^+$]$^+$: 472.3; found: 472.3.

tert-Butyl (S)-3-(2-cyclohexyl-4-((S)-2-ethylpiperazine-1-carbonyl) phenoxy) pyrrolidine-1-carboxylate (116c). 116c (0.1515 g, 74% yield) as off-white solid. $^1$H NMR (500 MHz, Chloroform-d) δ 7.13 (d, J=24.2 Hz, 2H), 6.73 (t, J=7.0 Hz, 1H), 4.89 (tt, J=4.2, 1.8 Hz, 1H), 3.70-3.37 (m, 4H), 3.06 (s, 1H), 2.94-2.75 (m, 4H), 2.70 (d, J=12.6 Hz, 1H), 2.26-1.96 (m, 4H), 1.86 (dt, J=14.8, 7.6 Hz, 1H), 1.80-1.56 (m, 6H), 1.41 (d, J=5.5 Hz, 9H), 1.36-1.07 (m, 6H), 0.97-0.64 (m, 3H); $^{13}$C NMR (126 MHz, Chloroform-d) δ 171.12, 154.99, 154.93, 154.59, 154.43, 137.21, 128.92, 126.06, 125.59, 125.38, 112.03, 111.77, 79.43, 79.43, 76.48, 75.35, 51.48, 51.07, 48.16, 46.30, 44.26, 43.89, 37.38, 37.30, 33.10, 32.79, 32.65, 31.68, 31.00, 28.46, 27.00, 26.29, 22.00, 10.62; LRMS-ESI: Exact mass calcd for $C_{28}H_{44}N_3O_4$ [M+H$^+$]$^+$: 486.3; found: 486.4.

tert-Butyl (S)-3-(2-cyclohexyl-4-((S)-2-isopropylpiperazine-1-carbonyl) phenoxy) pyrrolidine-1-carboxylate (116d). 116d (0.1233 g, 79% yield) as off-white solid. $^1$H NMR (500 MHz, Chloroform-d) δ 7.25-7.11 (m, 2H), 6.76 (t, J=8.6 Hz, 1H), 4.93 (d, J=4.2 Hz, 1H), 4.33 (s, 1H), 3.76-3.41 (m, 5H), 3.32-2.55 (m, 6H), 2.41 (dp, J=10.6, 6.6 Hz, 1H), 2.26-2.03 (m, 3H), 1.92-1.66 (m, 7H), 1.45 (d, J=6.5 Hz, 9H), 1.41-1.18 (m, 6H), 1.12-0.70 (m, 6H); $^{13}$C NMR (126 MHz, Chloroform-d) δ 170.75, 154.94, 154.63, 154.48, 137.27, 129.03, 126.41, 126.12, 125.71, 125.34, 112.03, 111.70, 79.48, 76.50, 75.41, 55.08, 51.50, 51.14, 46.74, 44.83, 44.29, 43.93, 37.43, 33.12, 32.82, 32.72, 31.73, 31.06, 28.50, 27.02, 26.32, 25.39, 20.01, 19.14; LRMS-ESI: Exact mass calcd for $C_{29}H_{46}N_3O_4$ [M+H$^+$]$^+$: 500.4; found: 500.4.

General procedure A for synthesis of 117a-d. In a 100 mL round bottom flask, 114 (0.025 g, 1.27 mmol, 1 equiv.) was dissolved in CH$_2$Cl$_2$:DMF (1:1) (10 mL) and cooled to 0° C. 1-Bis(dimethylamino)methylene-1H-1,2,3-triazolo[4,5-b]pyridinium 3-oxid hexafluorophosphate (HATU) (0.072 g, 0.19 mmol, 1.5 equiv.) was added to the reaction mixture and stirred for 5 min. Then 116a-d (0.059 g, 0.13 mmol, 1.01 equiv.) was added followed by dropwise addition of N,N-diisopropylethylamine (0.05 mL, 0.25 mmol, 2 equiv.). The reaction was stirred and allowed to warm to room temperature. The reaction was concentrated under reduced pressure then diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford the titled compound.

tert-Butyl (S)-3-(4-(4-(3-acetamido-5-fluorobenzoyl) piperazine-1-carbonyl)-2-cyclohexylphenoxy) pyrrolidine-1-carboxylate (117a). 117a (0.0685 g, 85% yield). $^1$H NMR (500 MHz, (CD$_3$)$_2$CO) δ 9.54 (s, 1H), 7.65 (d, J=11.2 Hz, 1H), 7.45 (d, J=3.5 Hz, 1H), 7.32 (d, J=2.7 Hz, 1H), 7.29 (dd, J=8.3, 2.2 Hz, 1H), 7.02 (d, J=8.3 Hz, 1H), 6.88 (ddd, J=8.5, 2.5, 1.3 Hz, 1H), 5.13 (dt, J=7.1, 3.6 Hz, 1H), 3.88-3.37 (m, 12H), 2.98-2.84 (m, 1H), 2.27-2.14 (m, 2H), 2.07 (s, 3H), 1.89-1.67 (m, 6H), 1.49-1.22 (m, 13H); $^{13}$C NMR (126 MHz, (CD$_3$)$_2$CO) δ 170.0, 168.6, 168.1 (d, J=2.8 Hz), 162.5 (d, J=243.6 Hz), 155.4, 154.0, 153.9, 141.4 (d, J=11.4 Hz), 138.4, 138.3, 136.7 (d, J=12.4 Hz), 128.2, 128.1, 126.4, 126.4, 113.4, 112.3 (d, J=13.6 Hz), 108.3 (d, J=23.3 Hz), 106.8 (d, J=26.6 Hz), 78.4, 76.7, 75.7, 51.4, 51.0, 44.2, 43.9, 37.5, 37.4, 32.9, 32.6, 32.4, 31.4, 30.6, 27.8, 26.9, 26.2, 23.4; LRMS-ESI: Exact mass calcd for $C_{35}H_{45}FN_4NaO_6$ [M+Na]$^+$: 659.3; found: 659.4.

tert-Butyl (S)-3-(4-((S)-4-(3-acetamido-5-fluorobenzoyl)-2-methylpiperazine-1-carbonyl)-2-cyclohexylphenoxy)pyrrolidine-1-carboxylate (117b). 117b (0.0887 g, quantitative yield). $^1$H NMR (500 MHz, Acetone-d$_6$) δ 9.48 (s, 1H), 7.65 (d, J=11.1 Hz, 1H), 7.46 (s, 1H), 7.28 (s, 2H), 7.26 (d, J=2.1 Hz, 1H), 7.09-6.96 (m, 1H), 6.88 (s, 1H), 5.18-5.09 (m, 1H), 3.67-3.02 (m, 8H), 2.95-2.85 (m, 1H), 2.31-2.12 (m, 2H), 2.09 (d, J=1.1 Hz, 7H), 1.88-1.66 (m, 7H), 1.42 (d, J=13.5 Hz, 13H), 1.30-1.19 (m, 5H); $^{13}$C NMR (126 MHz, Acetone-d$_6$) δ 170.25, 168.80, 162.51 (d, J=243.5 Hz), 155.34, 154.11, 153.96, 141.35 (d, J=11.3 Hz), 138.33, 138.26, 136.72 (d, J=10.1 Hz), 128.59, 126.02, 125.97, 113.31, 112.47, 112.36, 108.36 (d, J=23.3 Hz), 106.83 (d, J=26.8 Hz), 78.45, 76.73, 75.66, 51.44, 50.97, 44.21, 43.89, 37.50, 37.41, 32.90, 32.60, 32.41, 31.38, 30.56, 29.74, 27.77, 26.90, 26.07, 23.41, 14.84; LRMS-ESI: Exact mass calcd for $C_{36}H_{47}FN_4NaO_6$ [M+Na]$^+$: 673.3; found: 673.4.

tert-Butyl (S)-3-(4-((S)-4-(3-acetamido-5-fluorobenzoyl)-2-ethylpiperazine-1-carbonyl)-2-cyclohexylphenoxy)pyrrolidine-1-carboxylate (117c). 117c (0.0895 g, quantitative yield). $^1$H NMR (500 MHz, Acetone-d$_6$) δ 9.50 (s, 1H), 7.64 (dt, J=11.3, 2.2 Hz, 1H), 7.45 (s, 1H), 7.26 (d, J=7.3 Hz, 2H), 7.06-6.96 (m, 1H), 6.87 (d, J=7.7 Hz, 1H), 5.13 (d, J=4.7 Hz, 1H), 4.51 (d, J=40.7 Hz, 1H), 3.82-3.26 (m, 5H), 3.02-2.74 (m, 1H), 2.33-2.12 (m, 2H), 2.08 (d, J=2.6 Hz, 5H), 1.86-1.66 (m, 7H), 1.42 (d, J=14.4 Hz, 11H), 1.31-1.19 (m, 1H), 0.80 (m, 3H); $^{13}$C NMR (126 MHz, Acetone-d$_6$) δ 170.70, 168.84, 162.50 (d, J=243.7 Hz), 155.28, 154.14, 153.98, 141.36 (d, J=11.4 Hz), 138.26, 138.19, 136.77 (d, J=12.2 Hz), 128.60, 128.44, 126.09, 126.02, 113.31, 112.44 (d, J=18.9 Hz), 108.34 (d, J=23.1 Hz), 106.85 (d, J=26.4 Hz), 78.49, 76.74, 75.66, 51.43, 50.98, 44.22, 43.91, 37.50, 37.41, 32.96, 32.54, 32.36, 31.38, 30.56, 29.76, 27.78, 26.90, 26.07, 23.44, 21.93, 9.97; LRMS-ESI: Exact mass calcd for $C_{37}H_{49}FN_4NaO_6$ [M+Na]$^+$: 687.4; found: 687.4.

tert-Butyl (S)-3-(4-((S)-4-(3-acetamido-5-fluorobenzoyl)-2-isopropylpiperazine-1-carbonyl)-2-cyclohexylphenoxy)pyrrolidine-1-carboxylate (117d). 117d (0.0705 g, 82% yield). $^1$H NMR (500 MHz, Acetone-d$_6$) δ 9.39 (s, 1H), 7.66 (d, J=11.1 Hz, 1H), 7.45 (s, 1H), 7.34-7.19 (m, 2H), 7.03 (d, J=9.4 Hz, 1H), 6.88 (d, J=8.3 Hz, 1H), 5.14 (s, 1H), 4.79 (s, 1H), 4.48 (s, 1H), 3.76-3.19 (m, 5H), 3.03-2.74 (m, 2H), 2.09 (d, J=5.1 Hz, 10H), 2.08-2.06 (m, 2H), 1.88-1.61 (m, 7H), 1.54-1.30 (m, 15H), 1.20-0.60 (m, 5H); $^{13}$C NMR (126 MHz, Acetone-d$_6$) δ 168.96, 162.48 (d, J=244.2 Hz), 155.23, 154.19, 154.03, 141.19 (d, J=12.6 Hz), 138.17, 138.12, 136.71 (d, J=12.6 Hz), 128.56, 126.18, 113.34, 112.25 (d, J=18.9 Hz), 108.47, 106.85, 78.56, 76.53, 75.78, 51.44, 50.93, 44.22, 43.88, 37.47, 37.26, 33.09, 31.32, 30.53, 27.83, 27.66, 26.84, 26.04, 23.39, 19.72, 18.39; LRMS-ESI: Exact mass calcd for $C_{38}H_{51}FN_4NaO_6$ [M+Na]$^+$: 701.4; found: 701.4.

General procedure E for synthesis of 12-15. In a 20 mL vial, 117a-d (1 equiv.) was dissolved in CH$_2$Cl$_2$ (4 mL) and cooled to 0° C. Then, TFA (2 mL) was added dropwise to the reaction mixture. The reaction was stopped when TLC confirmed completion of the reaction and the solvent was concentrated under reduced pressure. The product was dissolved in DI water (10 mL) and the aqueous layer was washed with ethyl acetate (3×10 mL). The resulting aqueous solution was frozen and lyophilized to yield the titled compound.

(S)—N-(3-(4-(3-Cyclohexyl-4-(pyrrolidin-3-yloxy) benzoyl) piperazine-1-carbonyl)-5-fluorophenyl) acetamide trifluoroacetate (12). 12 (0.0435 g, 91% yield). HPLC purity 99%; $^1$H NMR (500 MHz, CD$_3$OD) δ 7.59-7.50 (m, 1H), 7.48-7.44 (m, 1H), 7.35 (d, J=2.1 Hz, 1H), 7.31 (dd, J=8.4, 2.2 Hz, 1H), 7.02 (d, J=8.4 Hz, 1H), 6.93 (ddd, J=8.2, 2.5, 1.4 Hz, 1H), 5.26 (q, J=4.3, 3.8 Hz, 1H), 3.91-3.40 (m, 11H), 3.05-2.92 (m, 1H), 2.41-2.30 (m, 2H), 2.13 (s, 3H), 1.95-1.70 (m, 6H), 1.58-1.25 (m, 6H); $^{13}$C NMR (126 MHz, CD$_3$OD) δ 172.9, 171.9, 170.9, 164.1 (d, J=245.1 Hz), 156.5, 142.3 (d, J=11.3 Hz), 138.6 (d, J=8.6 Hz), 138.5, 129.1, 127.8, 127.4, 114.9, 113.2, 110.1 (d, J=23.6 Hz), 109.1 (d, J=26.3 Hz), 77.0, 51.9, 45.6, 38.1, 34.3, 34.2, 32.2, 28.00, 27.97, 27.3, 24.0. HRMS-ESI: Exact mass calcd for $C_{30}H_{37}FN_4NaO_4$ [M+Na]$^+$: 559.2697; found: 559.2692.

N-(3-((S)-4-(3-Cyclohexyl-4-(((S)-pyrrolidin-3-yl) oxy)benzoyl)-3-methylpiperazine-1-carbonyl)-5-fluorophenyl)acetamide trifluoroacetate (13). 13 (0.0728 g, 80% yield). HPLC purity 99%; $^1$H NMR (500 MHz, Methanol-d$_4$) δ 7.55 (dd, J=11.3, 2.4 Hz, 1H), 7.46 (s, 1H), 7.31 (d, J=2.1 Hz, 1H), 7.28 (dd, J=8.3, 2.2 Hz, 1H), 7.02 (d, J=8.4 Hz, 1H), 6.92 (s, 1H), 5.36-5.21 (m, 1H), 4.51-4.41 (m, 2H), 3.81-3.37 (m, 6H), 3.24-3.04 (m, 1H), 2.99 (tt, J=11.4, 3.2 Hz, 1H), 2.44-2.30 (m, 2H), 2.13 (s, 3H), 1.93-1.69 (m, 6H), 1.58-1.11 (m, 9H); $^{13}$C NMR (126 MHz, Methanol-d$_4$) δ 172.97, 171.93, 171.50, 164.07 (d, J=245.2 Hz), 160.24 (q, J=39.5 Hz), 156.35, 142.31 (d, J=10.9 Hz), 138.57 (d, J=12.6 Hz), 138.52, 129.59, 127.28, 126.98, 114.83, 113.27, 110.03 (d, J=23.2 Hz), 109.07 (d, J=26.1 Hz), 77.01, 51.98, 47.30, 45.66, 43.35, 38.06, 34.34, 34.22, 32.14, 27.99, 27.97, 27.30, 23.95, 15.75. HRMS-ESI: Exact mass calcd for $C_{31}H_{39}FN_4NaO_4$ [M+Na]$^+$: 573.2853; found: 573.2848.

N-(3-((S)-4-(3-Cyclohexyl-4-(((S)-pyrrolidin-3-yl) oxy)benzoyl)-3-ethylpiperazine-1-carbonyl)-5-fluorophenyl) acetamide trifluoroacetate (14). 14 (0.0386 g, 78% yield). HPLC purity 99%; $^1$H NMR (500 MHz, Methanol-d$_4$) δ 7.54 (d, J=10.7 Hz, 1H), 7.46 (s, 1H), 7.34-7.22 (m, 2H), 7.02 (d, J=8.6 Hz, 1H), 6.92 (d, J=7.4 Hz, 1H), 5.25 (s, 1H), 4.57 (s, 2H), 3.78-3.39 (m, 7H), 3.15 (dd, J=12.5, 7.5 Hz, 1H), 3.00 (d, J=11.7 Hz, 1H), 2.35 (td, J=7.0, 6.3, 3.1 Hz, 2H), 2.14 (s, 3H), 1.88-1.76 (m, 6H), 1.56-1.23 (m, 6H), 1.14-0.55 (m, 3H); $^{13}$C NMR (126 MHz, Methanol-d$_4$) δ 173.29, 171.92, 171.66, 164.09 (d, J=245.4 Hz), 161.87 (q, J=36.5 Hz), 156.31, 142.37, 138.54, 129.70, 127.40, 127.08, 114.81, 113.26, 110.01 (d, J=23.5 Hz), 109.04 (d, J=26.5 Hz), 77.04, 51.95, 45.63, 38.08, 34.31, 32.17, 27.99, 27.31, 23.94, 23.22, 10.91. HRMS-ESI: Exact mass calcd for $C_{32}H_{41}FN_4NaO_4$ [M+Na]$^+$: 587.3010; found: 587.3003.

N-(3-((S)-4-(3-Cyclohexyl-4-(((S)-pyrrolidin-3-yl) oxy)benzoyl)-3-isopropylpiperazine-1-carbonyl)-5-fluorophenyl) acetamide trifluoroacetate (15). 15 (0.023 g, quantitative yield). HPLC purity 99%; $^1$H NMR (500 MHz, Methanol-d$_4$) δ 7.50 (d, J=34.2 Hz, 2H), 7.27 (d, J=15.3 Hz, 2H), 7.02 (s, 1H), 6.92 (d, J=7.9 Hz, 1H), 5.26 (s, 1H), 4.70-4.16 (m, 1H), 3.92-3.36 (m, 7H), 2.99 (s, 3H), 2.36 (s, 2H), 2.14 (s, 3H), 1.93-1.70 (m, 5H), 1.58-1.14 (m, 7H), 1.09-0.32 (m, 6H); $^{13}$C NMR (126 MHz, Methanol-d$_4$) δ 173.06, 171.92, 164.09 (d, J=245.1 Hz), 161.96 (q, J=36.5 Hz), 156.28, 142.34, 138.56, 129.67, 127.34, 127.01, 117.68 (q, J=291.1 Hz), 114.84, 113.24, 110.02 (d, J=24.1 Hz), 109.03 (d, J=26.0 Hz), 77.05, 57.26, 51.97, 45.64, 44.92, 44.28, 38.09, 34.31, 32.18, 28.00, 27.31, 23.94, 20.59, 20.24, 19.34. HRMS-ESI: Exact mass calcd for $C_{33}H_{43}FN_4NaO_4$ [M+Na]$^+$: 601.3166; found: 601.3158.

The synthesis of 16 is shown in Scheme 5. The Cbz protection of (S)-4-Boc-2-isobutyl piperazine using benzyl chloroformate resulted in 118, which underwent Boc deprotection by TFA and then the amide coupling reaction with 114 afforded 119. The deprotection of the Cbz protecting group by catalytic hydrogenation generated 120. The amide coupling of 120 with 103a gave 121. The deprotection of the Boc protecting group of 121 offered final product 16.

Scheme 5: The synthesis of compound 16.

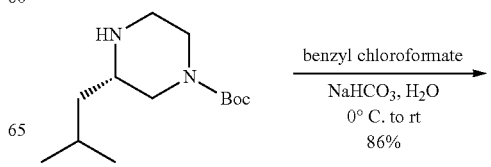

benzyl chloroformate
NaHCO$_3$, H$_2$O
0° C. to rt
86%

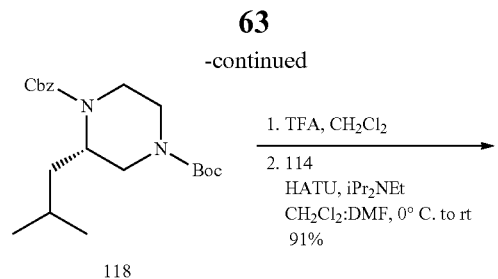

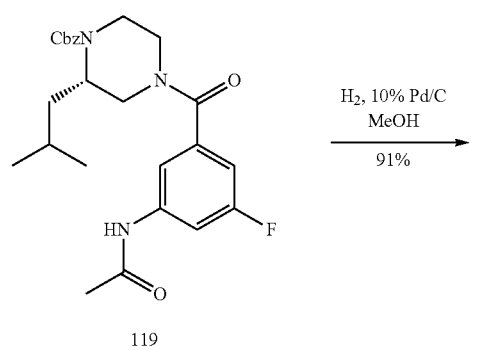

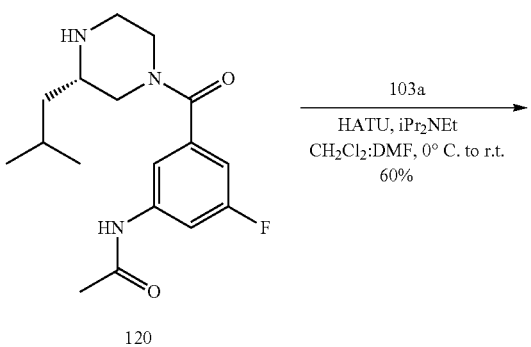

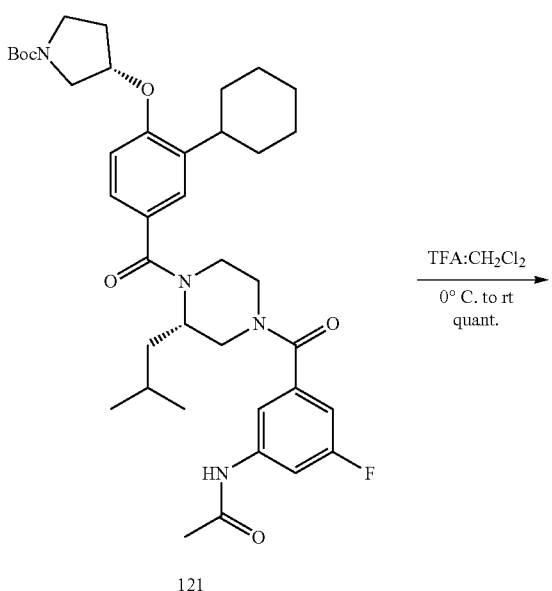

1-Benzyl 4-(tert-butyl) (S)-2-isobutylpiperazine-1,4-dicarboxylate (118). (S)-4-Boc-2-isobutyl piperazine (0.6602 g, 2.724 mmol) was mixed with $NaHCO_3$ (0.6933 g, 8.172 mmol) in 5 mL $H_2O$ and 10 mL acetone at 0° C. To this stirred mixture was added dropwise benzyl chloroformate (0.8 mL, 5.448 mmol). The solution was stirred at 0° C. for 30 min then at room temperature for 5 h. The solvent was evaporated in vacuo and the residue was participated between EtOAc (20 mL) and $H_2O$ (20 mL). The aqueous layer was further extracted with EtOAc (20 mL) twice. The combined organic layer was washed with brine, and the solvent evaporated in vacuo. The residue was subjected to column chromatography to offer the titled compound (0.8779 g, 86% yield). $^1$H NMR (500 MHz, Chloroform-d) δ 7.56-7.29 (m, 5H), 5.29-5.01 (m, 2H), 4.49-4.04 (m, 2H), 3.96 (d, J=28.7 Hz, 2H), 3.19-2.59 (m, 3H), 1.48 (s, 12H), 0.91 (s, 6H); $^{13}$C NMR (126 MHz, Chloroform-d) δ 155.20, 154.91, 136.54, 128.49, 128.09, 128.02, 79.97, 67.31, 49.70, 46.62, 45.70, 44.03, 42.83, 38.84, 37.88, 28.38, 24.76, 22.92, 22.45; LRMS-ESI: Exact mass calcd for $C_{21}H_{32}N_2NaO_4$ [M+Na]$^+$: 399.2; found: 399.3.

Benzyl (S)-4-(3-acetamido-5-fluorobenzoyl)-2-isobutylpiperazine-1-carboxylate (119). In a 25 mL vial, 118 (0.5 g, 1.33 mmol) was dissolved in $CH_2Cl_2$ (5 mL) and cooled to 0° C. Then, TFA (5 mL) was added dropwise to the reaction mixture. The reaction was stopped when TLC confirmed completion of the reaction and the solvent was concentrated under reduced pressure to yield the desired trifluoroacetate (quantitative yield), which was used without further purification.

In a 100 mL round bottom flask, the above trifluoroacetate (0.1292 g, 0.256 mmol) was dissolved in $CH_2Cl_2$:DMF (1:1) (10 mL) and cooled to 0° C. 1-[Bis(dimethylamino)methylene]-1H-1,2,3-triazolo[4,5-b]pyridinium 3-oxid hexafluorophosphate (HATU) (0.1446 g, 0.380 mmol) was added to the reaction mixture and stirred for 5 min. Then, 114 (0.05 g, 0.254 mmol) was added followed by dropwise addition of N,N-diisopropylethylamine (0.2 mL, 1.27 mmol). The reaction was stirred and allowed to warm to room temperature. The reaction was concentrated under reduced pressure, diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford the titled compound (0.1054 g, 91% yield). $^1$H NMR (500 MHz, Chloroform-d) δ 9.13-8.98 (m, 1H), 7.58-7.45 (m, 1H), 7.34 (d, J=6.0 Hz, 5H), 7.29-7.18 (m, 1H), 6.74 (d, J=7.8 Hz, 1H), 5.17-5.10 (m, 2H), 4.77-3.90 (m, 3H), 3.80-3.43 (m, 1H), 3.36-2.90 (m, 3H), 2.09 (s, 3H), 1.56-1.39 (m, 2H), 1.30-1.09 (m, 1H), 1.01-0.70 (m, 7H); $^{13}$C NMR (126 MHz, Chloroform-d) δ 170.06, 169.76, 169.40, 162.53 (d, J=247.2 Hz), 155.08, 140.70 (d, J=11.0 Hz), 136.73 (d, J=8.2 Hz), 136.16, 128.56, 128.28, 128.07, 113.72, 108.73, 108.52, 67.65, 50.13, 49.63, 47.44, 45.03, 42.15, 39.11, 37.97, 24.77, 24.55, 24.22, 22.65; LRMS-ESI: Exact mass calcd for C$_{25}$H$_{30}$FN$_3$NaO$_4$ [M+Na]$^+$: 478.2; found: 478.2.

(S)—N-(3-Fluoro-5-(3-isobutylpiperazine-1-carbonyl) phenyl) acetamide (120). In a 100 mL round bottom flask, compounds 119 (0.605 g, 1.33 mmol) was dissolved in MeOH (20 mL) and stirred. Then 10% wt. Palladium on activated carbon (0.011 g) was added portion wise to the reaction mixture. The atmosphere was exchanged with H$_2$ gas three times, and the reaction was allowed to stir under H$_2$. The reaction mixture was filtered through celite, and the solvent removed under reduced pressure to yield the residue, that was purified by column chromatography (CH$_2$Cl$_2$/MeOH=100/20) to afford the product (0.0673 g, 91% yield over two steps). $^1$H NMR (500 MHz, Chloroform-d) δ 9.23-9.06 (m, 1H), 7.58 (dd, J=37.3, 10.8 Hz, 1H), 7.12 (d, J=18.5 Hz, 1H), 6.69 (d, J=7.4 Hz, 1H), 4.48 (d, J=12.5 Hz, 1H), 3.55 (dd, J=27.9, 12.8 Hz, 1H), 3.20-2.14 (m, 7H), 2.06 (s, 3H), 1.41-1.19 (m, 2H), 1.17-1.04 (m, 1H), 0.99-0.71 (m, 6H); $^{13}$C NMR (126 MHz, Chloroform-d) δ 169.40, 169.08, 162.55 (d, J=246.8 Hz), 140.80 (d, J=13.1 Hz), 137.22, 113.84, 108.70 (d, J=11.3 Hz), 108.53, 53.97, 53.75, 53.11, 48.60, 48.41, 46.18, 45.49, 43.15, 42.99, 42.50, 24.31, 23.21, 22.95, 22.42; LRMS-ESI: Exact mass calcd for C$_{17}$H$_{25}$FN$_3$O$_2$ [M+H$^+$]$^+$: 322.2; found: 322.2.

tert-Butyl (S)-3-(4-((S)-4-(3-acetamido-5-fluorobenzoyl)-2-isobutylpiperazine-1-carbonyl)-2-cyclohexylphenoxy) pyrrolidine-1-carboxylate (121). In a 100 mL round bottom flask, 103a (0.040 g, 0.103 mmol) was dissolved in CH$_2$Cl$_2$:DMF (1:1) (10 mL) and cooled to 0° C. 1-Bis(dimethylamino)methylene-1H-1,2,3-triazolo[4,5-b]pyridinium3-oxid hexafluorophosphate (HATU) (0.058 g, 0.154 mmol) was added to the reaction mixture and stirred for 5 min. Then 120 (0.033 g, 0.104 mmol) was dissolved in DMF (1.01 equiv.) was added followed by dropwise addition of N,N-diisopropylethylamine (2 equiv.). The reaction was stirred and allowed to warm to room temperature. The reaction was concentrated under reduced pressure then diluted with ethyl acetate, extracted from 2 M HCl, and washed with brine. The organic layers were dried over Na$_2$SO$_4$, and concentrated under reduced pressure. The solid was purified by column chromatography (silica gel, 5-40% acetone in hexanes) to afford the titled compound (0.0424 g, 60% yield). $^1$H NMR (500 MHz, Methanol-d$_4$) δ 7.64-7.51 (m, 1H), 7.46 (s, 1H), 7.25 (d, J=11.6 Hz, 2H), 7.02 (d, J=8.4 Hz, 1H), 6.98-6.81 (m, 1H), 5.11 (s, 1H), 4.56 (d, J=12.1 Hz, 1H), 3.92-3.34 (m, 7H), 3.18-3.00 (m, 1H), 2.93-2.81 (m, 1H), 2.27-2.16 (m, 2H), 2.13 (s, 3H), 1.92-1.69 (m, 5H), 1.45 (d, J=16.4 Hz, 9H), 1.40-1.26 (m, 2H), 1.16-0.45 (m, 6H); $^{13}$C NMR (126 MHz, Methanol-d$_4$) δ 171.83, 171.34, 164.06 (d, J=246.5 Hz), 156.91, 156.50, 156.39, 142.39, 138.67 (d, J=24.3 Hz), 129.01, 127.45, 127.05, 114.71, 113.70, 109.97 (d, J=24.0 Hz), 109.00 (d, J=26.2 Hz), 81.04, 77.88, 77.01, 52.62, 52.15, 45.51, 45.15, 39.03, 38.96, 34.32, 33.72, 33.64, 32.37, 31.67, 28.76, 28.27, 28.22, 28.14, 27.37, 26.20, 23.95, 23.03; LRMS-ESI: Exact mass calcd for C$_{39}$H$_{53}$FN$_4$NaO$_6$ [M+Na]$^+$: 715.4; found: 715.3.

N-(3-((S)-4-(3-Cyclohexyl-4-(((S)-pyrrolidin-3-yl) oxy) benzoyl)-3-isobutylpiperazine-1-carbonyl)-5-fluorophenyl) acetamide trifluoroacetate (16). In a 20 mL vial, compound 121 (0.042 g, 0.061 mmol) was dissolved in CH$_2$Cl$_2$ (4 mL) and cooled to 0° C. Then, TFA (2 mL) was added dropwise to the reaction mixture. The reaction was stopped when TLC confirmed completion of the reaction and the solvent was concentrated under reduced pressure. The product was dissolved in DI water (10 mL) and the aqueous layer was washed with ethyl acetate (3×10 mL). The resulting aqueous solution was frozen and lyophilized to yield the titled compound (0.0439 g, quantitative yield). HPLC purity 99%; $^1$H NMR (500 MHz, Methanol-d$_4$) δ 7.58-7.51 (m, 1H), 7.48 (s, 1H), 7.31 (s, 1H), 7.27 (d, J=8.4 Hz, 1H), 7.02 (d, J=8.4 Hz, 1H), 6.90 (d, J=7.1 Hz, 1H), 5.25 (s, 1H), 4.75-3.90 (m, 1H), 3.85-3.38 (m, 7H), 3.19-2.99 (m, 3H), 2.48-2.26 (m, 2H), 2.14 (s, 3H), 1.96-1.67 (m, 5H), 1.63-1.20 (m, 8H), 1.18-0.37 (m, 7H); $^{13}$C NMR (126 MHz, Methanol-d$_4$) δ 173.55, 171.90, 171.61, 164.08 (d, J=242.9 Hz), 161.46 (q, J=38.1 Hz), 156.34, 142.38, 138.59, 129.65, 127.52, 127.08, 117.40 (q, J=289.7 Hz), 114.78, 113.23, 109.99 (d, J=24.0 Hz), 109.04 (d, J=26.4 Hz), 77.06, 51.95, 45.61, 38.12, 34.30, 32.15, 27.99, 27.31, 26.06, 23.94, 23.07.

Bioassays

Protein expression and purification. Wild-type full-length β-catenin were cloned into a pET-28b vector carrying a C-terminal 6×histidine (Novagen), and transformed into *Escherichia coli* BL21 DE3 (Novagen). Cells were cultured in LB medium with 30 μg/mL kanamycin until the OD$_{600}$ was approximately 0.8, and then protein expression was induced with 400 μM of IPTG at 20° C. overnight. Cells were lysed by sonication. The proteins were purified by Ni-NTA affinity chromatography (30210, Qiagen) and dialyzed against a buffer containing 20 mM of Tris (pH 8.5), 100 mM NaCl, 10% glycerol, and 3 mM DTT. The purity of β-eaten in was greater than 95% as determined by SDS-PAGE gel analysis. Native non-denaturing gel electrophoresis was performed to confirm the homogeneity of the purified proteins. Thermal-shift assay was performed on an iCycler iQ Real Time Detection System (Bio-Rad) to monitor protein stability and detect protein aggregation. Protein unfolding was evaluated through measuring the S15 fluorescence changes of fluorescent dye Sypro Orange when interacting with wild-type or mutant β-catenin proteins. A temperature increment of 17 min was applied. CD spectra were measured on a J-815 spectropolarimeter (Jasco). All spectra were recorded at room temperature, and the baseline control containing all of the substances except protein. Sample were prepared at a concentration around 1-5 μM in a buffer of 10 mM potassium phosphate and 100 mM potassium fluoride at pH 7.0 to ensure that the transmission of light through the sample was not restricted. All proteins were stable and no aggregation was observed under storage or assay conditions. Proteins were aliquoted and stored at −80° C.

BCL9 peptide synthesis and purification. Human BCL9 (residues 350-375), and A-terminally biotinylated human BCL9 (residues 350-375) were synthesized. All synthesized peptides were purified by HPLC with purity >95%. The structures were validated by LC/MS. The sequences are as follows (Ahx, 6-aminohexanoic acid).

| Peptide | Sequence |
|---|---|
| BCL9 26-mer | H-$^{350}$GLSQEQLEHRERSLQTLRDIQRMLFP$^{375}$-NH$_2$ |
| Biotinylated BCL9 26-mer | Biotin-Ahx-$^{350}$GLSQEQLEHRERSLQTLRDIQRMLFP$^{375}$-NH$_2$ |
| E-cadherin 54-mer | H$^{824}$APPYDSLLVFDYEGSGSEAASLSSLNSSESDKDQDYDYLNEWGNRFKKLADMYG$^{877}$-NH$_2$ |
| Biotinylated E-cadherin 54-mer | Biotin$^{824}$APPYDSLLVFDYEGSGSEAASLSSLNSSESDKDQDYDYLNEWGNRFKKLADMYG$^{877}$-NH$_2$ |

AlphaScreen competitive inhibition assays. For the competitive inhibition assays of the β-catenin/BCL9 PPI, the negative control (equivalent to 0% inhibition) refers to 5.0 nM of biotinylated BCL9, 40 nM of His$_6$-tagged β-catenin, and 10 μg/mL of donor and acceptor beads in a final volume of 25 μL assay buffer, but no tested inhibitor present. The positive control (equivalent to 100% inhibition) refers to 5.0 nM of biotinylated BCL9 and μg/mL of donor and acceptor beads in a final volume of 25 μL assay buffer.

For the β-catenin/BCL9 assay, 5 nM of biotinylated BCL9 and 40 nM of His$_6$-tagged β-catenin were incubated in assay buffer at 4° C. for 30 min. Different concentrations of the tested inhibitor were added and incubated in 20 μL assay buffer at 4° C. for another 1 h. All of the above assay plates were covered and gently mixed on an orbital shaker. The donor and acceptor beads were then added to the plates to a final concentration of 10 μg/mL in 25 μL assay buffer. The mixture was incubated for 1 h at 4° C. before detection. The IC$_{50}$ value was determined by nonlinear least-square analysis of GraphPad Prism 5.0. The K$_i$ values were derived from the IC$_{50}$ values using a method reported by Nikolovska-Coleska et al (Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. Anal. Biochem. 2004, 332, 261-273.). The assays were conducted under the conditions required by Nikolovska-Coleska et al.'s equation for determining the K$_i$ values. All of the experiments were performed in triplicate. The results were expressed as mean±standard deviation.

| | Ki (μM ± SD) | | | |
|---|---|---|---|---|
| Compound | experiment 1 | experiment 2 | experiment 3 | experiment 4 |
| 1 | 310 ± 48 | 310 ± 23 | | |
| 2 | 230 ± 33 | 220 ± 26 | | |
| 3 | 310 ± 32 | 550 ± 46 | | |
| 4 | 780 ± 59 | 310 ± 43 | | |
| 5 | 157 ± 17 | 160 ± 22 | | |
| 6 | 840 ± 64 | 380 ± 44 | | |
| 7 | 730 ± 73 | 240 ± 33 | | |
| 8 | 32 ± 4.0 | 71 ± 8.7 | | |
| 9 | >90 | >90 | | |
| 10 | 420 ± 50 | 76 ± 8.3 | | |
| 11 | 170 ± 23 | 150 ± 18 | | |
| 12 | | | 61 ± 7.5 | 37 ± 3.6 |
| 13 | | | 330 ± 34 | 100 ± 18 |
| 14 | | | 790 ± 58 | 780 ± 130 |
| 15 | | | 280 ± 27 | 290 ± 61 |
| 16 | | | 330 ± 43 | 200 ± 20 |

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound having a structure according to Formula I-A:

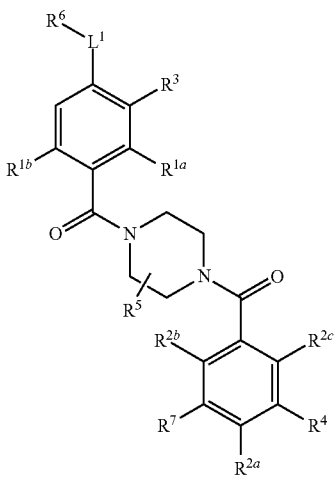

Formula I-A wherein $L^1$ is O, S, or NH;
wherein each of $R^{1a}$ and $R^{1b}$ is independently hydrogen, halogen, $C_1$-$C_3$ alkyl, $C_1$-$C_3$ monohaloalkyl, or $C_1$-$C_3$ polyhaloalkyl;
wherein each of $R^{2a}$, $R^{2b}$, and $R^{2c}$ is independently hydrogen, halogen, $C_1$-$C_3$ alkyl, $C_1$-$C_3$ haloalkyl, or $C_1$-$C_3$ polyhaloalkyl;
wherein $R^3$ is $Cy^3$ or $Ar^1$; wherein $Cy^3$ is a $C_3$-$C_8$ cycloalkyl or a $C_2$-$C_7$ heterocycloalkyl and Ar is selected from aryl and heteroaryl, wherein $Cy^3$ and $Ar^1$, when present, are substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$;
wherein $R^4$ is hydrogen, halogen, $C_1$-$C_3$ alkyl, $C_1$-$C_3$ haloalkyl, or $C_1$-$C_3$ polyhaloalkyl;
wherein each occurrence of $R^5$ is independently selected from hydrogen, $C_1$-$C_3$ alkyl;
wherein $R^6$ is $C_1$-$C_6$ aminoalkyl, $C_1$-$C_6$ hydroxyalkyl, or $Cy^1$; and wherein $Cy^1$ is an amino $C_3$-$C_8$ cycloalkyl, a hydroxy $C_3$-$C_8$ cycloalkyl, or a $C_2$-$C_7$ heterocycloalkyl comprising at least one oxygen or nitrogen atom; and wherein $Cy^1$ is substituted with 0, 1, 2, or 3 groups independently selected from halogen, $C_1$-$C_4$ alkyl, $C_1$-$C_4$ monohaloalkyl, and $C_1$-$C_4$ polyhaloalkyl;
wherein $R^7$ is $C_1$-$C_6$ alkyl-(C=O)—$NR^{12}$—, wherein said $C_1$-$C_6$ alkyl group is unsubstituted;
wherein $R^{12}$ is selected from hydrogen or $C_1$-$C_3$ alkyl;
or a pharmaceutically acceptable salt.

2. The compound of claim 1, wherein $L^1$ is O.

3. The compound of claim 1, wherein each of $R^{1a}$, $R^{1b}$, $R^{2a}$, $R^{2b}$, and $R^{2c}$ is hydrogen.

4. The compound of claim 1, wherein $R^3$ is cyclohexyl substituted with 0, 1, 2, or 3 groups independently selected from halogen, —CN, $C_1$-$C_3$ alkyl, $C_1$-$C_3$ monohaloalkyl, $C_1$-$C_3$ polyhaloalkyl, cyclopropyl, and —$CO_2H$.

5. The compound of claim 1, wherein $R^4$ is a halogen.

6. The compound of claim 1, wherein each occurrence of $R^5$ is selected from hydrogen, methyl, ethyl, propyl, or isopropyl.

7. The compound of claim 1, wherein Re is a $C_3$-$C_7$ heterocycloalkyl comprising at least one nitrogen atom.

8. The compound of claim 1, wherein $R^7$ is $CH_3$—(C=O)—$NR^{12}$—, $CH_3CH_2$—(C=O)—$NR^{12}$—, $CH_3CH_2CH_2$—(C=O)—$NR^{12}$—, or $CH_3CH_2CH_2CH_2$—(C=O)—$NR^{12}$—.

9. The compound of claim 2, wherein each of $R^{12}$ is hydrogen or methyl.

10. The compound of claim 1, having a structure represented by a formula below or a pharmaceutically acceptable salt thereof:

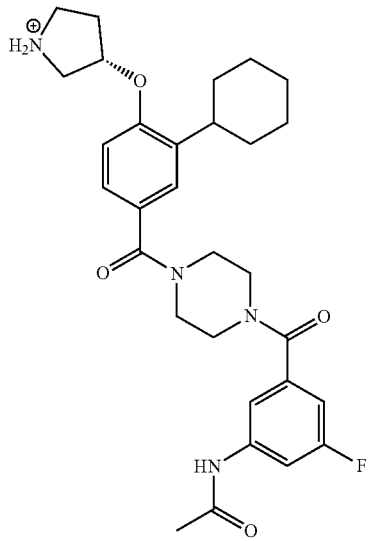

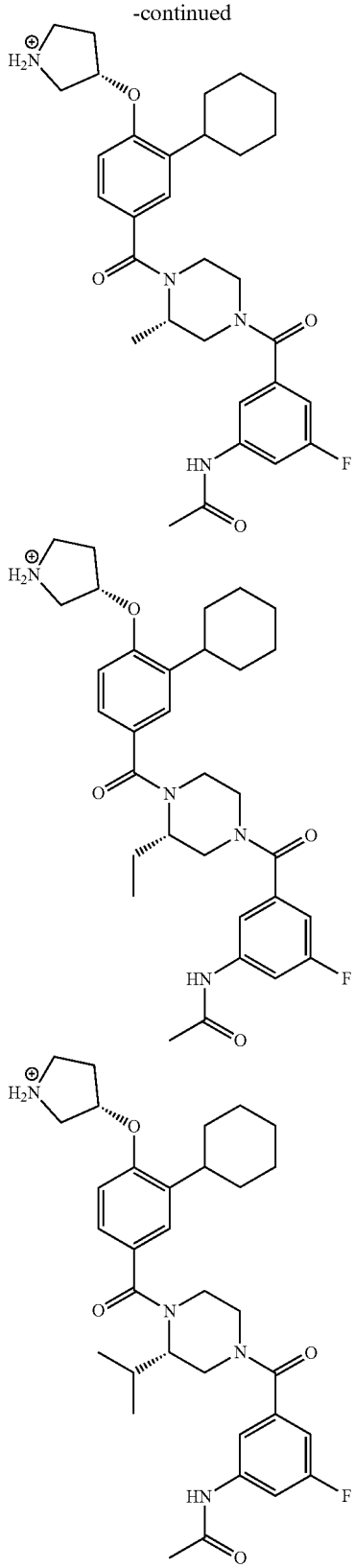

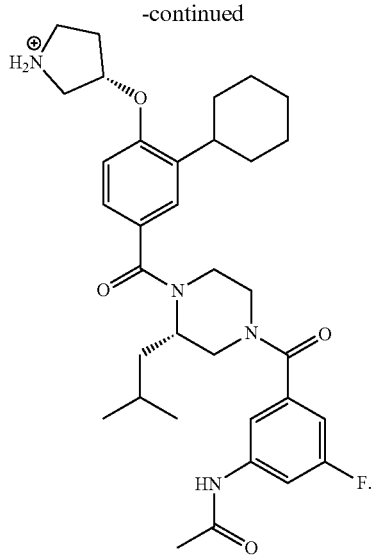

11. A pharmaceutical composition comprising a therapeutically effective amount of a compound of claim 1, or a pharmaceutically acceptable salt, ester, or prodrug thereof, and a pharmaceutically acceptable carrier.

12. A method for the treatment of a disorder of uncontrolled cellular proliferation associated with a β-catenin/BCL9 dysfunction in a mammal comprising the step of administering to the mammal an effective amount of a compound of claim 1, or a pharmaceutically acceptable salt, ester, or prodrug thereof.

13. The method of claim 12, wherein the mammal has been diagnosed with a need for treatment of the disorder prior to the administering step.

14. The method of claim 12, wherein the mammal is human; and wherein the human has been identified to have a 1q21 chromosomal abnormality.

15. The method of claim 12, further comprising the step of identifying a mammal in need of treatment of the disorder.

16. The method of claim 12, wherein the disorder is cancer.

17. A method for inhibiting protein-protein interactions of β-catenin and BCL9 in at least one cell, comprising the step of contacting the at least one cell with an effective amount of a compound of claim 1, or a pharmaceutically acceptable salt, ester, or prodrug thereof.

18. The method of claim 17, wherein the cell is in human.

* * * * *

SEQUENCE LISTING

<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: SYNTHETIC CONSTRUCT

<400> SEQUENCE: 1

Gly Leu Ser Gln Glu Gln Leu Glu His Arg Glu Arg Ser Leu Gln Thr
1               5                   10                  15

Leu Arg Asp Ile Gln Arg Met Leu Phe Pro
            20                  25

<210> SEQ ID NO 2
<211> LENGTH: 54
<212> TYPE: PRT
<213> ORGANISM: Artificial Sequence
<220> FEATURE:
<223> OTHER INFORMATION: SYNTHETIC CONSTRUCT

<400> SEQUENCE: 2

Ala Pro Pro Tyr Asp Ser Leu Leu Val Phe Asp Tyr Glu Gly Ser Gly
1               5                   10                  15

| | | | | | | | | | | | | |
|---|---|---|---|---|---|---|---|---|---|---|---|---|
| Ser | Glu | Ala | Ala | Ser | Leu | Ser | Ser | Leu | Asn | Ser | Ser | Glu | Ser | Asp | Lys |
| | | | 20 | | | | 25 | | | | 30 | |
| Asp | Gln | Asp | Tyr | Asp | Tyr | Leu | Asn | Glu | Trp | Gly | Asn | Arg | Phe | Lys | Lys |
| | | 35 | | | | | 40 | | | | | 45 | |
| Leu | Ala | Asp | Met | Tyr | Gly |
| | 50 |